US009956743B2

(12) United States Patent
Jin et al.

(10) Patent No.: US 9,956,743 B2
(45) Date of Patent: May 1, 2018

(54) SUPERHYDROPHOBIC AND SUPEROLEOPHOBIC NANOSURFACES

(75) Inventors: Sungho Jin, San Diego, CA (US); Chulmin Choi, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 1338 days.

(21) Appl. No.: 13/996,477

(22) PCT Filed: Dec. 20, 2011

(86) PCT No.: PCT/US2011/001995
§ 371 (c)(1),
(2), (4) Date: Sep. 19, 2013

(87) PCT Pub. No.: WO2012/087352
PCT Pub. Date: Jun. 28, 2012

(65) Prior Publication Data
US 2014/0011013 A1    Jan. 9, 2014

Related U.S. Application Data

(60) Provisional application No. 61/425,205, filed on Dec. 20, 2010, provisional application No. 61/508,591, filed on Jul. 15, 2011.

(51) Int. Cl.
B32B 7/02         (2006.01)
G03F 7/00         (2006.01)
(Continued)

(52) U.S. Cl.
CPC ............. B32B 7/02 (2013.01); B05D 5/00 (2013.01); B05D 5/08 (2013.01); B05D 5/083 (2013.01);
(Continued)

(58) Field of Classification Search
CPC ... B32B 7/02; G03F 7/0002; H01L 31/02366; H01L 31/0236; H01L 21/3065;
(Continued)

(56) References Cited

U.S. PATENT DOCUMENTS 6,764,745 B1 * 7/2004 Karasawa ................ B32B 3/30
                                                            428/141
7,258,731 B2   8/2007 D'Urso et al.
(Continued)

FOREIGN PATENT DOCUMENTS

WO    2002049980 A1    6/2002
WO    2007128965 A1    1/2007
(Continued)

OTHER PUBLICATIONS

Blossey, R., "Self-Cleaning Surfaces—Virtual Realities," Nature Materials, 2(5):301-306, May 2003.
(Continued)

Primary Examiner — Anita K Alanko
(74) Attorney, Agent, or Firm — Perkins Coie LLP

(57) ABSTRACT

Devices, systems and techniques are described for producing and implementing articles and materials having nanoscale and microscale structures that exhibit superhydrophobic, superoleophobic or omniphobic surface properties and other enhanced properties. In one aspect, a surface nanostructure can be formed by adding a silicon-containing buffer layer such as silicon, silicon oxide or silicon nitride layer, followed by metal film deposition and heating to convert the metal film into balled-up, discrete islands to form an etch mask. The buffer layer can be etched using the etch mask to create an array of pillar structures underneath the etch mask, in which the pillar structures have a shape that includes cylinders, negatively tapered rods, or cones and are vertically aligned. In another aspect, a method of fabricating
(Continued)

microscale or nanoscale polymer or metal structures on a substrate is made by photolithography and/or nano imprinting lithography.

11 Claims, 33 Drawing Sheets

(51) Int. Cl.

| | | |
|---|---|---|
| H01L 31/0236 | (2006.01) | |
| B05D 5/00 | (2006.01) | |
| B05D 5/08 | (2006.01) | |
| B81C 1/00 | (2006.01) | |
| B82Y 40/00 | (2011.01) | |
| H01L 21/308 | (2006.01) | |
| H01L 21/3065 | (2006.01) | |
| B82B 3/00 | (2006.01) | |
| A01N 25/34 | (2006.01) | |

(52) U.S. Cl.
CPC ........ *G03F 7/0002* (2013.01); *H01L 31/0236* (2013.01); *H01L 31/02366* (2013.01); *A01N 25/34* (2013.01); *B81B 2203/0361* (2013.01); *B81B 2207/11* (2013.01); *B81C 1/00111* (2013.01); *B81C 1/00206* (2013.01); *B81C 1/00404* (2013.01); *B81C 1/00428* (2013.01); *B81C 1/00531* (2013.01); *B82B 3/0038* (2013.01); *B82Y 40/00* (2013.01); *H01L 21/3065* (2013.01); *H01L 21/3086* (2013.01); *Y02E 10/50* (2013.01); *Y10T 428/24994* (2015.04); *Y10T 428/249924* (2015.04)

(58) Field of Classification Search
CPC ......... H01L 21/3086; B05D 5/00; B05D 5/08; B05D 5/083; B81C 1/00531; B81C 1/00428; B81C 1/00111; B81C 1/00404; B81C 1/00206; B82Y 40/00; B81B 2207/11; B81B 2203/0361; B82B 3/0038; A01N 25/34; Y10T 428/24
See application file for complete search history.

(56) References Cited

U.S. PATENT DOCUMENTS

| | | | |
|---|---|---|---|
| 7,531,120 B2 | 5/2009 | Van Rijn et al. | |
| 7,851,045 B2* | 12/2010 | Gandon | B32B 17/10761 |
| | | | 428/141 |
| 8,241,508 B2* | 8/2012 | D'Urso | B01L 3/0244 |
| | | | 216/11 |
| 9,108,880 B2* | 8/2015 | Jin | B81C 1/00206 |
| 2002/0138049 A1* | 9/2002 | Allen | A61B 5/14514 |
| | | | 604/272 |
| 2002/0142150 A1* | 10/2002 | Baumann | B08B 17/06 |
| | | | 428/328 |
| 2004/0063100 A1* | 4/2004 | Wang | B81B 1/008 |
| | | | 435/6.11 |
| 2005/0181195 A1 | 8/2005 | Dubrow | |
| 2006/0024504 A1 | 2/2006 | Nelson et al. | |
| 2006/0024508 A1 | 2/2006 | D'Urso et al. | |
| 2006/0029808 A1* | 2/2006 | Zhai | B05D 5/04 |
| | | | 428/412 |
| 2006/0128239 A1 | 6/2006 | Nun et al. | |
| 2007/0026193 A1 | 2/2007 | Luzinov et al. | |
| 2007/0148815 A1 | 6/2007 | Chao et al. | |
| 2007/0184247 A1 | 8/2007 | Simpson et al. | |
| 2007/0231542 A1 | 10/2007 | Deng et al. | |
| 2008/0199657 A1 | 8/2008 | Capron et al. | |
| 2008/0199659 A1* | 8/2008 | Zhao | C03C 17/28 |
| | | | 428/161 |
| 2009/0011222 A1* | 1/2009 | Xiu | C23C 18/00 |
| | | | 428/323 |
| 2009/0324308 A1 | 12/2009 | Law et al. | |
| 2010/0038342 A1 | 2/2010 | Lim et al. | |
| 2010/0055397 A1 | 3/2010 | Kurihara et al. | |
| 2010/0206367 A1 | 8/2010 | Jeong et al. | |
| 2010/0285275 A1* | 11/2010 | Baca | C03C 3/083 |
| | | | 428/141 |
| 2011/0229667 A1 | 9/2011 | Jin et al. | |

FOREIGN PATENT DOCUMENTS

| | | |
|---|---|---|
| WO | 2007054649 A1 | 5/2007 |
| WO | 2007102960 A1 | 9/2007 |
| WO | 2007126432 A1 | 11/2007 |
| WO | 2010022107 A2 | 2/2010 |
| WO | 2012087352 A2 | 6/2012 |

OTHER PUBLICATIONS

Cassie, A.B.D., et al., "Wettability of Porous Surfaces," Transactions of the Faraday Society, 40:546-551, Jan. 1944.
Choi, C., et al., "Strongly Superhydrophobic Silicon Nanowires by Supercritical CO2 Drying," Electronic Materials Letters, 6(2):59-64, Jun. 2010.
Coulson, S.R., et al., "Super-Repellent Composite Fluoropolymer Surfaces," The Journal of Physical Chemistry B, 104(37):8836-8840, Aug. 2000.
Gapin, A.I., et al., "CoPt patterned media in anodized aluminum oxide templates," Journal of Applied Physics, 99(8):08G902(1-3), Apr. 2006.
Kim, J.-Y., et al., "Optically Transparent Glass with Vertically Aligned Surface Al2O3 Nanowires Having Superhydrophobic Characteristics," NANO: Brief Reports and Reviews, 5(2):89-95, Apr. 2010.
Parkin, I.P., et al., "Self-Cleaning Coatings," Journal of Materials Chemistry, 15(17):1689-1695, Dec. 2004.
Shimoda, T., et al., "Solution-Processed Silicon Films and Transistors," Nature, 440(7085):783-786, Apr. 2006.
International Search Report and Written Opinion of International Application No. PCT/US2009/054235, dated Apr. 8, 2010 (13 pages).
International Search Report and Written Opinion of International Application No. PCT/US2011/001995, dated Nov. 29, 2012 (10 pages).

* cited by examiner

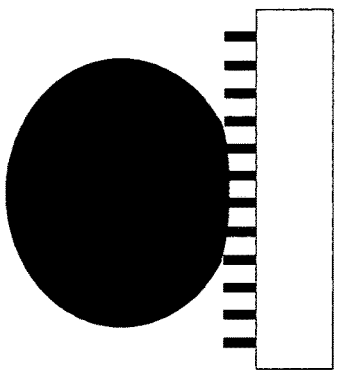
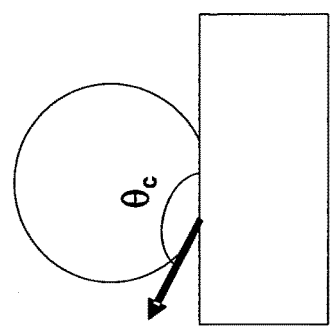
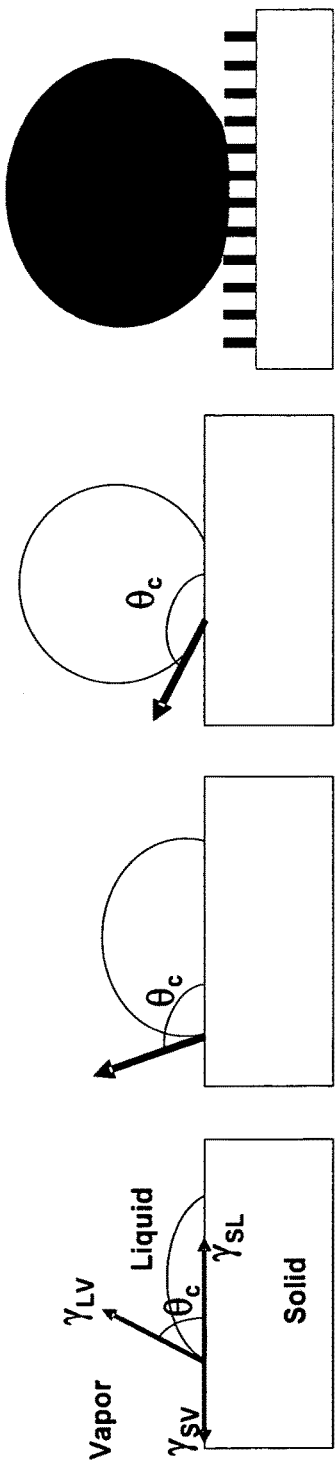
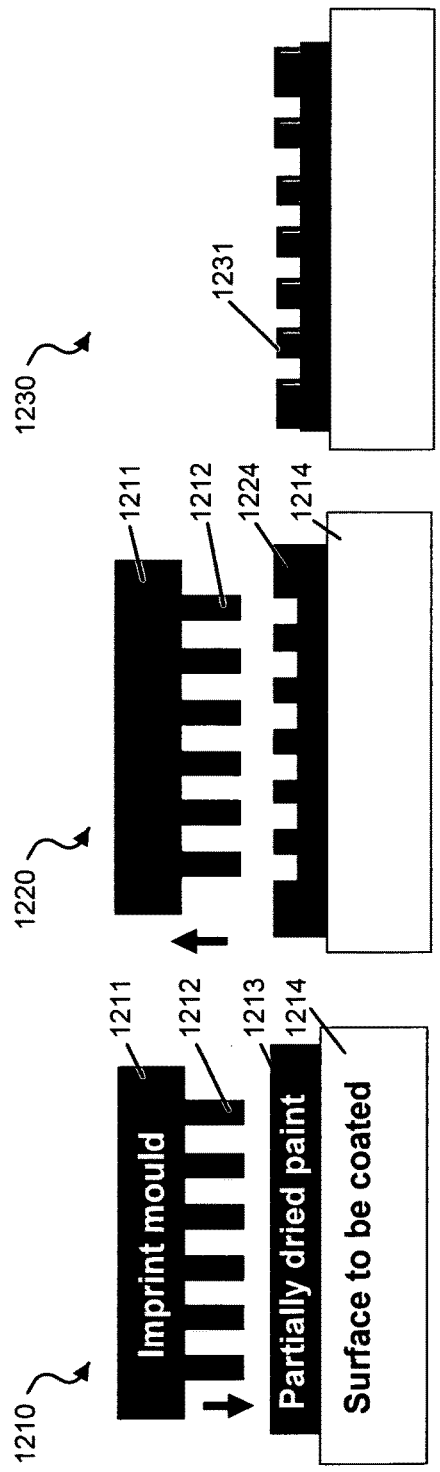

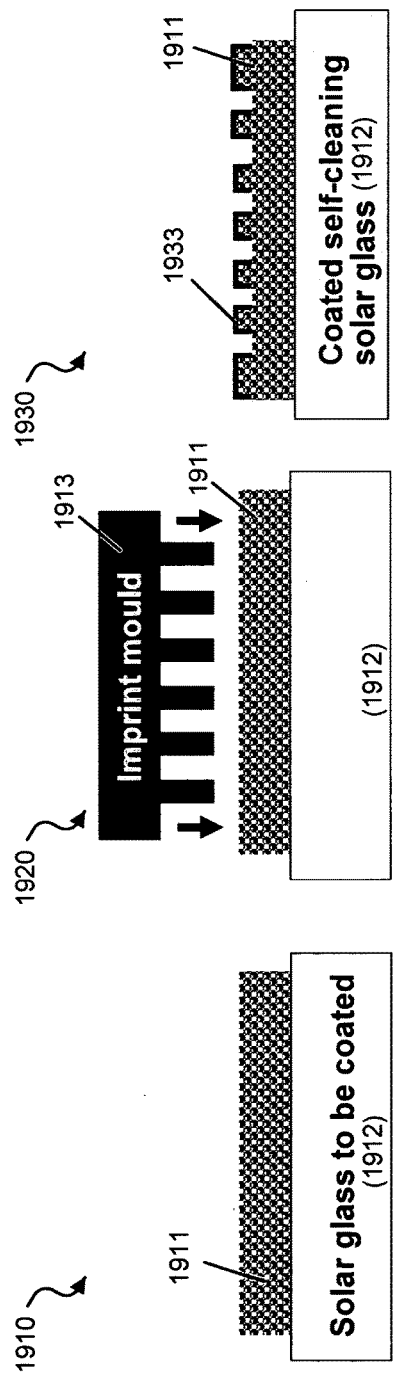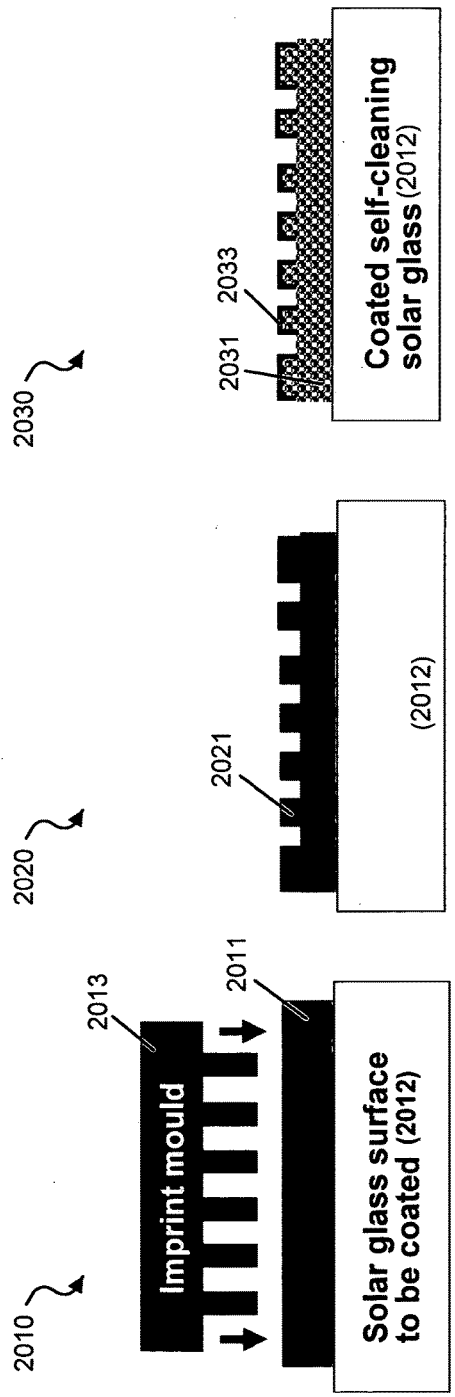

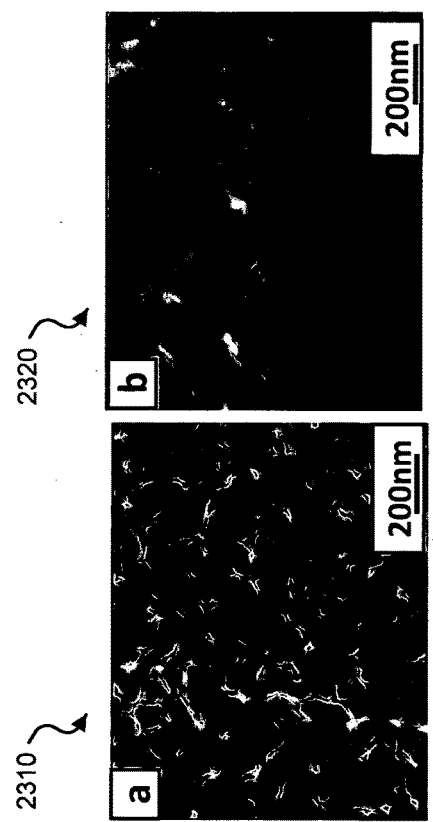
FIG. 23A  FIG. 23B  FIG. 23C
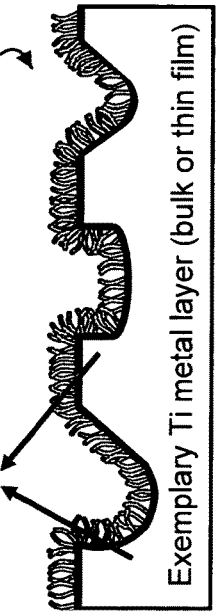
FIG. 24
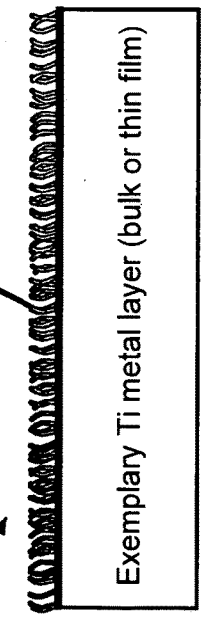

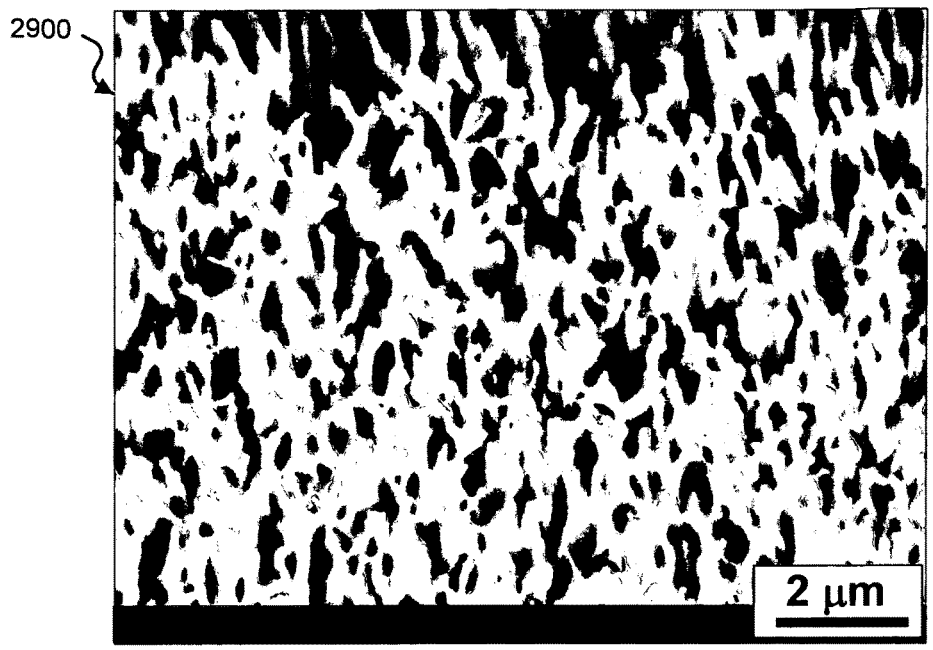
FIG. 29
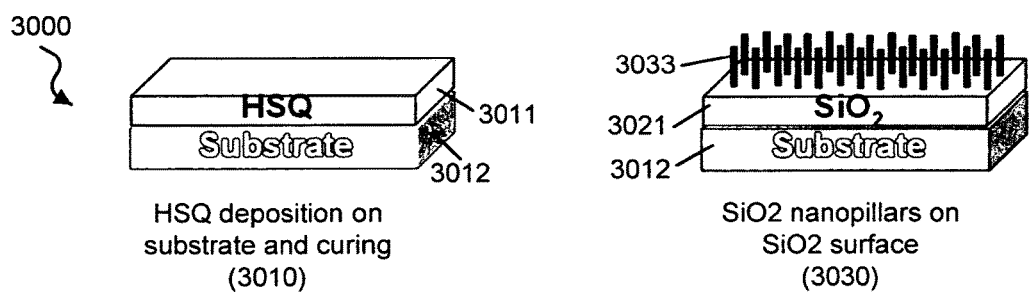
HSQ deposition on substrate and curing (3010)
SiO2 nanopillars on SiO2 surface (3030)
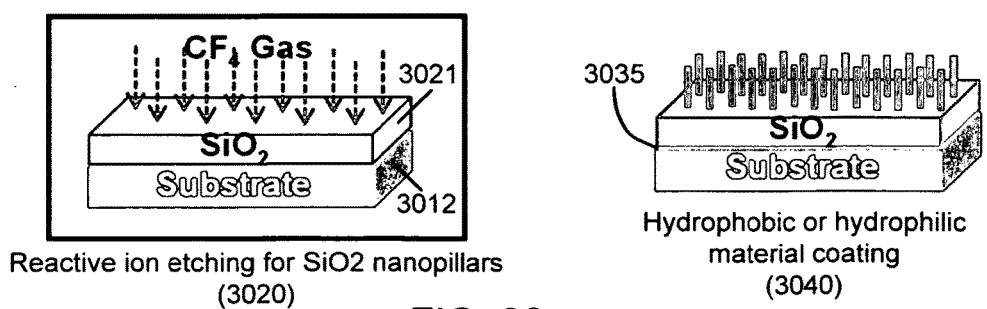
Reactive ion etching for SiO2 nanopillars (3020)
Hydrophobic or hydrophilic material coating (3040)
FIG. 30

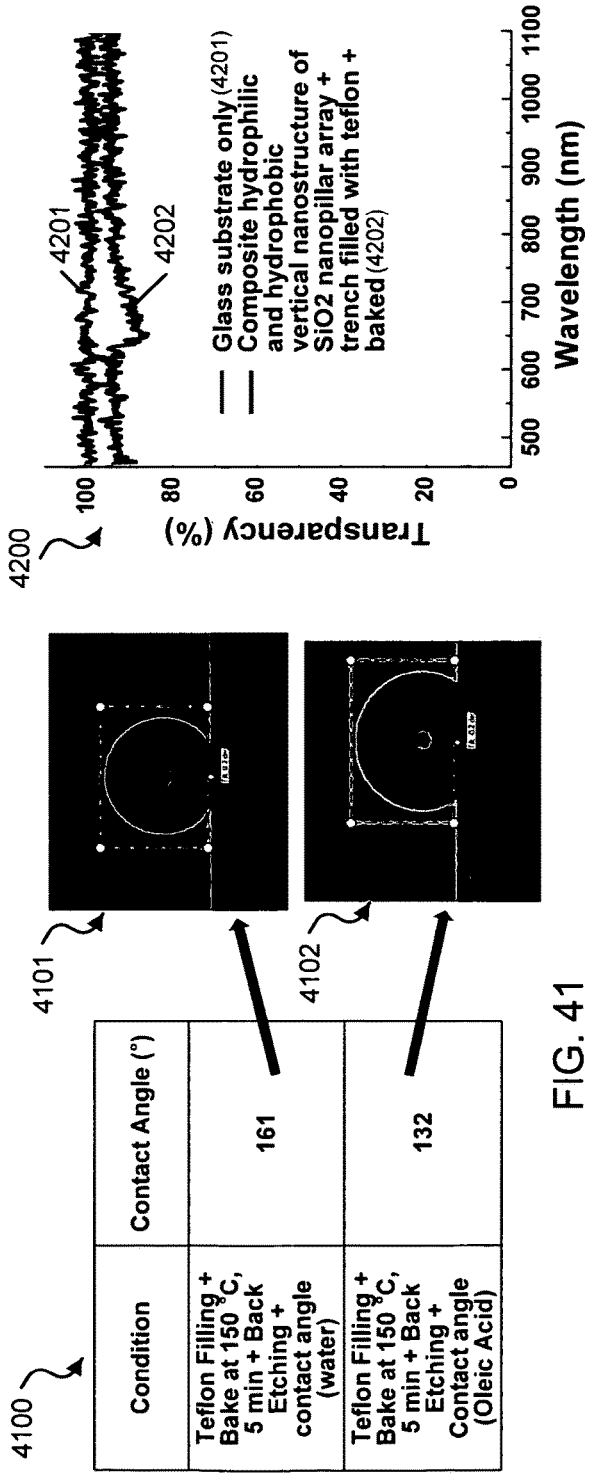
FIG. 41
FIG. 42
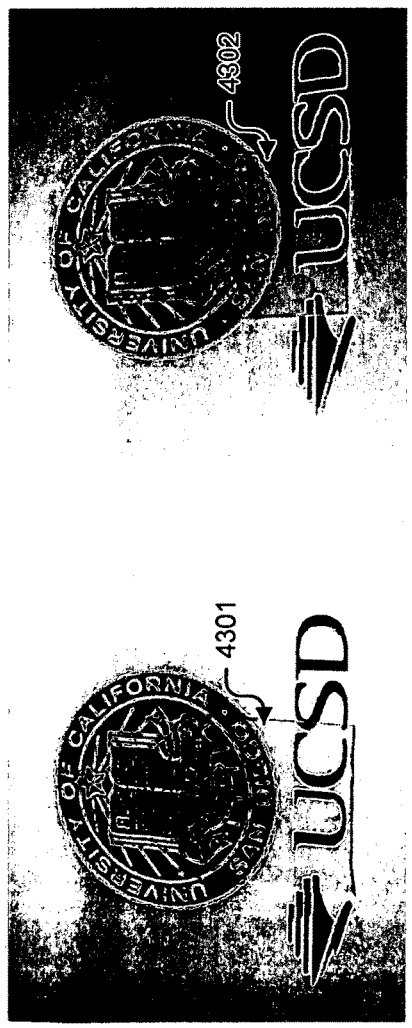
FIG. 43

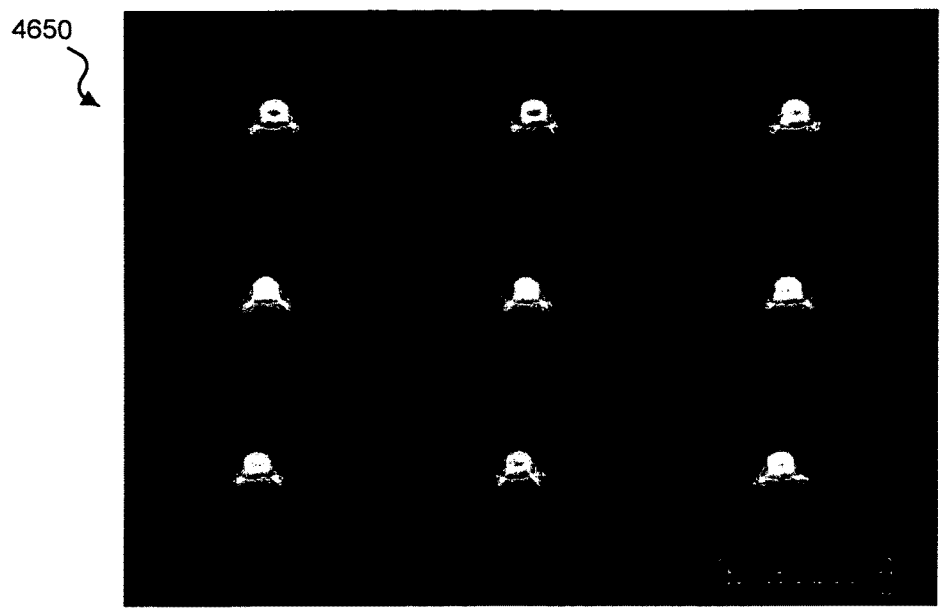
FIG. 46B
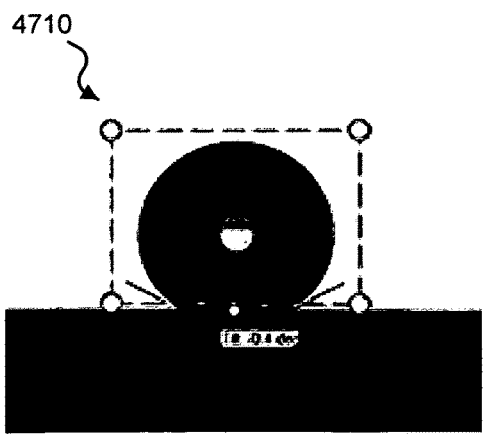
**Water Drop
Contact Angle : 153°**
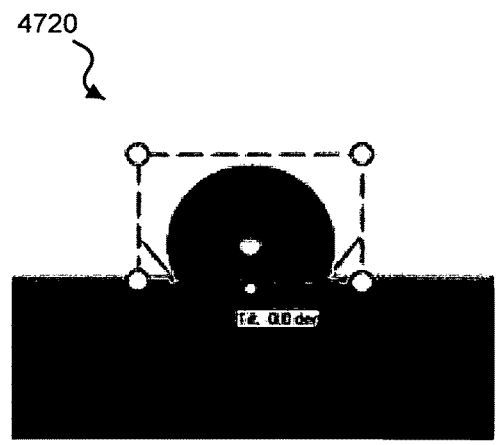
**Oil (Glycerol) drop
Contact Angle : 137°**
FIG. 47

SUPERHYDROPHOBIC AND SUPEROLEOPHOBIC NANOSURFACES

CROSS-REFERENCE TO RELATED APPLICATIONS

This application is a 35 USC § 371 National Stage application of International Application No. PCT/US2011/001995 filed Dec. 20, 2011, which further claims the benefit of priority to U.S. Provisional Patent Application No. 61/425,205, entitled "ANTI-FINGERPRINT COATINGS FOR DISPLAY SURFACES" and filed Dec. 20, 2010, and U.S. Provisional Patent Application No. 61/508,591, entitled "SUPERHYDROPHOBIC AND SUPEROLEOPHOBIC NANO SURFACE DEVICES, METHODS, AND USES" and filed Jul. 15, 2011. The disclosure of each of the prior applications is considered part of and is incorporated by reference in the disclosure of this application.

BACKGROUND

This application relates to devices and techniques that use nanotechnologies.

Hydrophobicity is a property of matter that relates to the repulsion of molecules from a mass of water. For example, when a water droplet comes in contact with a surface of a substance or sample, the droplet can form a spherical-like shape, which can be characterized by the degree of contact, e.g., the contact angle. A surface of a solid material is generally considered to be hydrophobic surface if the water contact angle is greater than 90°. Surfaces with water contact angles greater than ~130° are generally considered superhydrophobic. Superhydrophobic surfaces have very high water repellency, and water drops tend to roll off the surface at small inclination, which can take with them surface dirt and contaminants. Development and exploitation of superhydrophobic surfaces may provide useful benefits in a variety of applications.

SUMMARY

Devices, systems and techniques are described for producing and implementing articles and materials having nanoscale and microscale structures that exhibit superhydrophobic or superomniphobic surface properties and other enhanced properties.

In one aspect of the disclosed technology, a method of fabricating a material with a pillar array surface includes depositing a buffer layer on a substrate, in which the buffer layer material is a silicon-containing material, adding a film layer over the buffer layer, annealing the film layer to form balled-up structures that are distributed in an array of balled-up islands over the buffer layer to produce an etch mask, and etching the buffer layer using the etch mask to create an array of pillar structures underneath the etch mask, in which the pillar structures have a shape that includes cylinders, negatively tapered rods, or cones and are vertically aligned.

In another aspect, a device includes an enhanced nanostructure surface having an array of silicon-containing nanopillars on a substrate with enhanced superhydrophobic, superoleophobic or superomniphobic surface characteristics, in which the nanopillars are configured to have a diameter and a height in a range of 10 nm to 10 μm.

In another aspect, a method of fabricating a superhydrophobic coating on a surface includes depositing at least one layer of paint on the surface, utilizing a nano imprinting process that includes imprinting a stamp having arrangement of nano pillar tips on the surface when the paint is partially dry and releasing the stamp that imprints a nanostructure imprint in the shape of the nano pillar tips on the surface, and depositing a thin layer of a coating material over the surface.

In another aspect, a method of fabricating a superomniphobic coating on a surface of a solar cell panel includes depositing a uniform layer of a paste or slurry on the surface of the solar cell panel, in which the paste or slurry comprises nanoparticles mixed with a precursor, a binder, and a solvent; utilizing a nano imprinting process that includes imprinting a stamp into the uniform layer when the paste or slurry is partially dry, in which the stamp includes an array of nano pillar structures that have nano pillar tips, and releasing the stamp, whereby a nanostructure imprint having a shape of the array of nano pillar tips is imprinted into the uniform layer; curing or drying the uniform layer; and depositing a thin layer of a coating material over the surface.

In another aspect, a device includes an enhanced nanostructure surface that includes titania nanotubes on a substrate with enhanced superhydrophobic or superomniphobic surface characteristics, in which the enhanced nanostructure surface forms at least a 170° contact angle of a water droplet.

In another aspect, a device having an enhanced superhydrophobic and superomniphobic surface, includes a substrate, an adhesion layer on the substrate, a deposition material on the adhesion layer; and a layer of nanowire structures grown on the deposition material.

In another aspect, a method for fabricating a nanostructure surface with impregnated and trapped liquid to render a surface superhydrophobic, superoleophobic or superhydrophilic includes coating a liquid on a surface with an arrangement of nano pores, applying a pressure that impregnates and traps the liquid into the nano pores, and releasing the pressure.

In another aspect, a method for fabricating a nanostructure surface with impregnated and trapped liquid to render a surface superhydrophobic, superoleophobic or superhydrophilic includes coating a liquid on a surface with an arrangement of nano pillars or nanowire trenches, applying a pressure that impregnates and traps the liquid into the nano pillars or the nano trenches, and releasing the pressure.

In another aspect, a device comprising an enhanced superhydrophobic, superoleophobic, or superhydrophilic surface includes a substrate, an array of nano pillars vertically aligned on the substrate, in which a trench is formed in between each nano pillar of the array of nano pillars, and capsules comprising a fluorine-containing liquid, in which the capsules are trapped between the nanopores and/or nano pillars.

In another aspect, a display screen includes an enhanced nanostructure surface having an array of Si-containing nanopillars on a substrate with enhanced superhydrophobic, superoleophobic or superomniphobic surface characteristics, in which the enhanced nanostructure surface is optically transparent and exhibits wear resistant and anti-fingerprint surface properties.

In another aspect, a method of fabricating an anti-fingerprint surface coating structure includes depositing a transparent buffer layer of a buffer layer material on a transparent substrate material, in which the transparent buffer layer material is a silicon-containing material, adding a mask layer of a mask layer material over the transparent buffer layer, in which the adding includes patterning the mask layer material to form a patterned mask, and etching the transparent buffer layer using the patterned mask to create an array of pillar structures of the transparent buffer layer material underneath the patterned mask, in which the pillar structures have a shape that includes at least one of a substantially straight cylinder, negatively tapered rod, or cone and are aligned substantially vertical.

In another aspect, an anti-fingerprint surface structure includes an array of nano-sized pillars within a plurality of grids of crisscrossed grid lines of a line spacing and a line width on a transparent substrate, in which the pillars have a shape that includes at least one of a cylinder, negatively tapered rod, or cone and are vertically aligned to render the anti-fingerprint surface structure with superhydrophobic, superoleophobic, or superomniphobic surface properties.

The subject matter described in this patent document potentially can provide one or more of the following advantages. The disclosed technology can implemented to produce articles and materials with engineered nanostructures or microstructures on a substrate surface to enhance superhydrophobic or superomniphobic surface properties. The exemplary articles and materials can have enhanced light transmission and absorption characteristics, e.g., when the substrate itself is an optically transparent material. Implementing methods of the disclosed technology can convert a substrate to an enhanced self-cleaning and optically enhanced material. For example, enhanced optical properties and minimized dirt can advantageously be utilized for enhanced energy efficiency in photovoltaic solar cells, dye sensitized solar cells, thermoelectric energy conversion devices, sunlight focusing lens devices, waveguides, and other optical devices. The exemplary articles and materials can have enhanced photocatalytic characteristics. For example, the exemplary articles and materials can be configured as a solar induced photocatalytic surface that can use UV or visible light exposure to create superoxide and other radical type active components capable of decomposing toxic chemicals or anti-bacterial effect for water treatment or environmental clean-up. The exemplary articles and materials can have enhanced anti-corrosive properties and be coated on the surfaces of vehicles, buildings, etc. to prevent corrosion. The exemplary articles and materials can be used to provide superhydrophobic coatings on boats, water sports vehicles, and other water contact systems to increase thrust and reduce energy consumption. The exemplary articles and materials can have enhanced mechanical strength and hardness to maintain superhydrophobic, superoleophobic, and/or superomniphobic properties even after mechanical rubbing and erosion. For example, the exemplary articles and materials can cover touch-screen displays to provide a wear-resistant surface for various electronic, photonic and consumer devices. The exemplary articles and materials can be formed from compliant materials to exhibit a curved surface. The exemplary articles and materials can have anti-fingerprinting and superoleophobic properties. For example, the exemplary articles and materials can cover touch-screen displays to provide a self-cleaning surface for various electronic, photonic and consumer devices.

BRIEF DESCRIPTION OF THE DRAWINGS

FIGS. 11A-11C show exemplary illustrations of water drop contact angles on hydrophilic, hydrophobic, and superhydrophobic surfaces.

FIG. 11D shows exemplary illustration of surface protruding nanostructures to induce superhydrophobic characteristics.

FIG. 12 shows an exemplary process to produce a nano-patterned superhydrophobic surface.

FIG. 19 shows an exemplary method for fabricating self-cleaning solar glass surface nanostructures.

FIG. 20 shows another exemplary method to fabricate a superhydrophobic, self-cleaning solar glass surfaces.

FIGS. 23A and 23B show exemplary SEM images of vertically aligned $TiO_2$ nanotube arrays.

FIG. 23C shows an exemplary transmission electron microscope (TEM) image of vertically aligned $TiO_2$ nanotube arrays.

FIG. 24 shows an exemplary schematic of a flat surface and a micro-rough surface modified to exhibit superhydrophobic or omniphobic properties.

FIG. 29 shows an exemplary SEM image of adherent ZnO nanowire array.

FIG. 30 shows an exemplary process to produce a SiO$_2$ nanowire layered surface.

FIG. 41 shows an exemplary table and images of water and oil contact angle measurements on a superomniphobic surface.

FIG. 42 shows an exemplary plot of transparency vs. wavelengths of a superomniphobic composite material and a glass substrate.

FIG. 43 shows an exemplary photograph of a superomniphobic composite material and a glass substrate.

FIG. 46B shows an SEM image of an exemplary material with an omniphobic coating.

FIG. 47 shows exemplary images and contact angle measurement data for anti-fingerprint materials.

Like reference symbols and designations in the various drawings indicate like elements.

DETAILED DESCRIPTION

Figure 1:
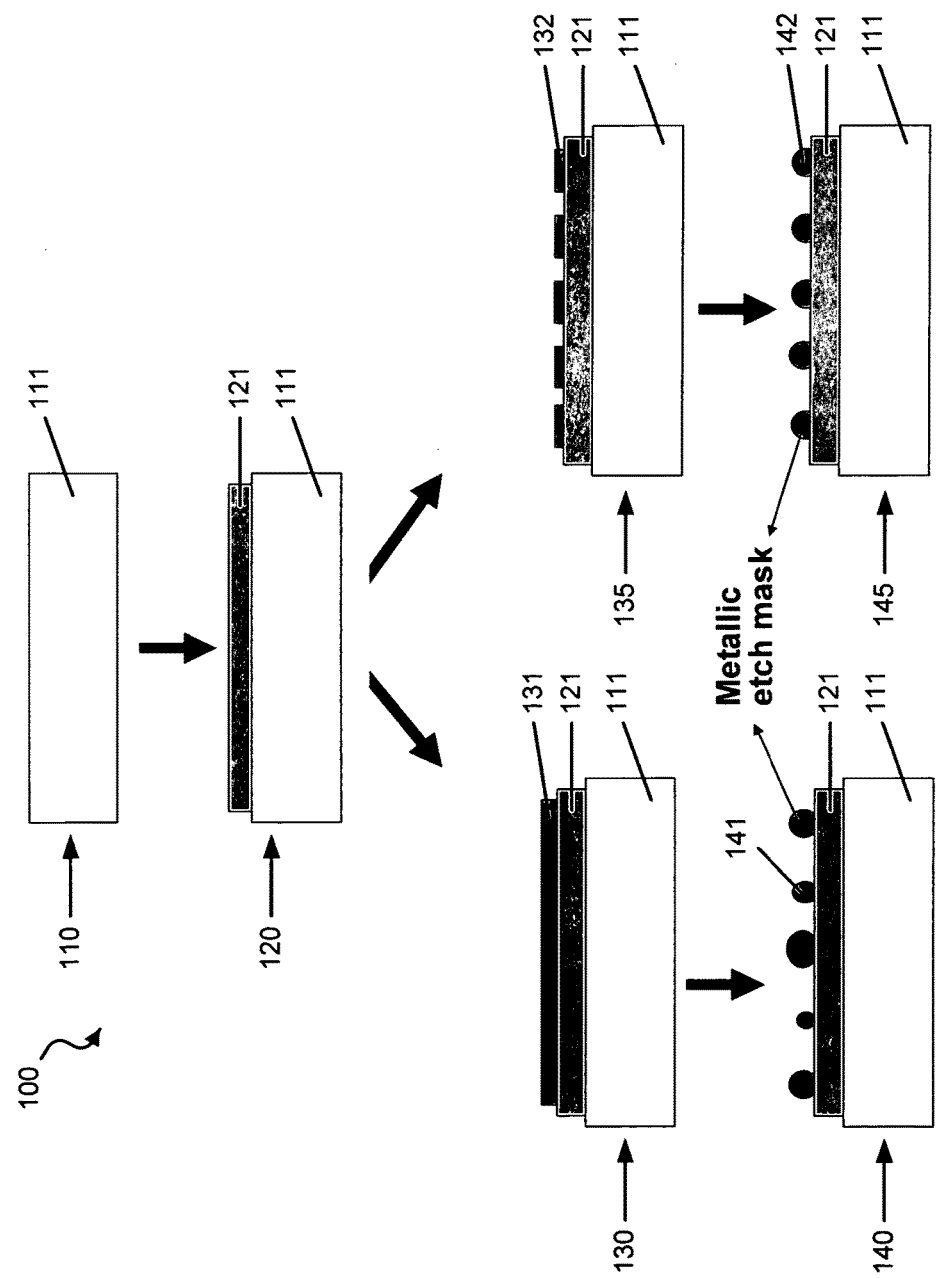
FIG. 1 shows an exemplary process to produce metallic etch mask island arrays.

Devices, systems and techniques are described for producing and implementing articles and materials having nanoscale and microscale structures that exhibit superhydrophobic or superomniphobic surface properties and other enhanced properties.

The superhydrophobic or omniphobic articles and materials described in this patent document can be engineered from nanostructures or microstructures on a substrate to enhance its surface properties. For example, the nanostructures or microstructures can be configured as an array of pillar, wires, rods, and/or cone structures on a substrate. The material-type, size, geometry, and/or arrangement on the substrate of the nano- or micro-structures can be configured to repel water and/or oil substances beyond that of the ordinary substrate. For example, the disclosed technology can be implemented to produce a superhydrophobic material from a hydrophilic or hydrophobic material. Additionally, an article or material can be engineered to augment other properties including optical transparency and light absorption, photocatalysis, anti-corrosion, mechanical strength and hardness, and non-fouling and anti-fingerprint, among others. Exemplary articles and materials can cover touch-screen displays to provide a self-cleaning surface for various electronic, photonic and consumer devices.

Several embodiments of the superhydrophobic or omniphobic articles and materials are described herein. In one embodiment of the disclosed technology, nanoscale and microscale structures can be formed on a substrate to form superhydrophobic, non-wettable surfaces. For example, surface nanostructures can be formed by adding a silicon-containing buffer layer onto a substrate, followed by metal film deposition and heating to convert the metal film into balled-up, discrete islands. The metal islands can be used as efficient etch mask for chemical or reactive ion etching of the buffer layer (and optionally the substrate material itself) underneath the metal islands to form arrays of nano-sized pillar (or other geometric structures) on the substrate. The exemplary substrates featuring the nanopillars can provide enhanced self-cleaning or optically improved surfaces, for example, which can be used for various electronic, photonic and consumer devices. The disclosed technology can include silicon-based nanoscale pillar array surfaces that can exhibit unique optical characteristics of light transmission greater than the original transparent substrate, increasing light absorption. Additionally, the exemplary substrates featuring nanopillar array surfaces can minimize sunlight-blocking dirt on the surface due to superhydrophobic or omniphobic properties, which can be used to enhance energy efficiency in photovoltaic solar cells, dye sensitized solar cells, thermoelectric energy conversion devices, sunlight focusing lens devices, waveguides, and other optical devices. A method of fabricating nanoscale or microscale structures having superhydrophobic or omniphobic surfaces that includes using a Si-containing buffer layer is exemplified in FIG. 1 and FIG. 2.

FIG. 1 schematically illustrates an exemplary process (100) to fabricate a metallic etch mask, which can have superhydrophic, non-wettable surface properties. Process (100) can include process (110) to select a substrate (111) to be surface patterned. For example, the substrate (111) can be glass, soda lime window glass, solar cell cover glass, sapphire, silicon (Si), silicon-germanium (Si—Ge), zinc oxide (ZnO), gallium nitride (GaN), gallium arsenide (GaAs), soda lime silicate glass, quartz, alkaline earth boro-aluminosilicate, sodium boro-silicate glass, Pyrex glass, carbon, graphite, nitride, oxide, fluoride, or any metallic, semiconductor, ceramic or some polymer surfaces.

Process (100) can include process (120) to deposit a buffer layer (121) onto the substrate (111). For example, the buffer layer (121) can be a Si-containing buffer layer, e.g., Si, silicon oxide ($SiO_2$) or silicon nitride layer. It is noted that buffer layer (121) can of a non-silicon-containing material, which can be determined based on the substrate material, e.g., for optimal adherence of the buffer layer to the substrate. Process (120) can include the buffer layer being prepared by plasma-enhanced chemical vapor deposition (PECVD), sputter deposition, evaporation deposition, or other methods, with an optional post-deposition heat treatment in air, inert gas, vacuum, or oxygen-containing or nitrogen-containing environment. For example, buffer layer (121) can be configured in process (120) to have a desired thickness of 0.5 nm to 50 µm or fall within this range, e.g., 10-500 nm, 0.02-50 µm, 0.001-1 µm, 0.1-10 µm, or 0.3-3 µm, or be among other thickness ranges or be a specified thickness.

Process (100) can include process (130) to add a metal or alloy film layer (131). For example, the metal film layer (131) can be silver (Ag), gold (Au), copper (Cu), nickel (Ni), 70% Cu—30% Ag, or other related metal or alloy material. Alternatively, non-metal materials such as carbon, oxide or nitride islands may also be used as the film layer in process (130). Metal film layer (131) can be selected from a number of different metals such as Ni, Cu and other transition metals, Ag, Au, Pt, and other novel metals, or other metals, or alloys of these elements. The use of strongly adherent or strongly oxidizing metals such as Al, Cr, Ti, Zr, etc. may be less desirable as the metal film layer as these metals tend to strongly adhere to the substrate as a layer rather than forming the desired, discrete islands on annealing. The metal thin film can be deposited on substrate (111) with the deposited buffer layer (121) in a convenient manner using methods that include, for example, thin film or thick film evaporation, sputtering, chemical deposition, electroless or electrochemical deposition, or other methods. The film layer (e.g., metal thin film (131)) can have a desired thickness in a range of 0.5 nm to 1 µm or fall within this range, e.g., 1-100 nm, 2-20 nm, or be among other thickness ranges or be a specified thickness. Metal thin film (131) can then be transformed into the formation of metal islands on a substrate through the sintering of a thin film. For example, by controlling the thickness of the metal deposition film layer, and controlling the time, temperature and atmosphere of the post-deposition annealing heat treatment (e.g., at 300-500° C. for 10-10,000 min), the geometry and dimension of the metal islands can be adjusted. For example, the annealing temperature can be configured within a range of temperatures, e.g., 200° C. to 1,000° C. Through adjusting the chemical or reactive ion etch conditions, the size, shape, and roughness of nano or microscale protrusions can be altered, for example, cone, straight pillar, or negative tapered side wall pillar shape.

Process (100) can include process (140) to anneal for a balled-up island array to create a metallic etch mask, such as the exemplary metallic etch mask island array (141) shown in FIG. 1. The metallic etch mask island array (141) can be formed as a well-defined, well-adhered, surface-reacted island array of metal in which the balled-up metallic structures are of the material selected in process (130). For example, island array (141) can be produced by annealing at 200-900° C. or at 300-500° C. (below the melting temperature or softening temperature of the substrate to be patterned), for a period of for 10-10,000 min. In the exemplary ball-up annealing process (140), a gas atmosphere such as nitrogen ($N_2$), argon (Ar), or combination of hydrogen ($H_2$) and $N_2$ can be used to prevent the metal layer from oxidization during the ball-up annealing. A vacuum environment may also be used.

The annealing ball-up process from the blanket-deposited metal film deposition tends to produce slightly random metal island size. These slight variations of metal island geometry can be acceptable for creation of desired superhydrophobic or omniphobic surface nanostructures. Process (100) can also include a process (135) to deposit periodic metal patterns, e.g., patterned metal film layer (132). For example, process (135) can include patterning techniques including lithography, nano-imprinting, and/or shadow masking. Process (135) can be a substitute to process (130). Process (100) can also include a process (145) to perform ball-up annealing to create a patterned metallic etch mask, such as the exemplary metallic etch mask patterned island array (142) shown in FIG. 1. Implementation of process (135) and process (145) can result in the metal island etch mask having periodic or substantially identical size, which may produce more consistent self-cleaning properties and enhanced light transmission.

Various degrees of control can be implemented in process (100). For example, by controlling the thickness of the metal deposition film layer and controlling the time, temperature and atmosphere of the post-deposition annealing heat treatment, the geometry and dimension of the metal islands can be adjusted. By controlling the chemical or reactive ion etch conditions, the size, shape, and roughness of nano or microscale protrusions can be altered, for example, cone, straight pillar, or negative tapered side wall pillar shape.

After implementation of process (100), the buffer layer can be used to enhance the formation of island-like or vertical pillar-like structures, which can be on a variety of substrates including silicon, silicon oxide or silicon nitride buffer layer. The formation of the nanostructures can be implemented by PECVD, sputter deposition, evaporation deposition, or any method, with an optional post-deposition heat treatment in air, inert gas, vacuum, or oxygen-containing or nitrogen-containing environment. Additional processes can be included for further modification of exemplary nanopillars (such as silicon dioxide pillar nanostructures) to exhibit omniphobic properties. Also, other materials can also be employed to produce these self cleaning articles and devices, which can also be more optically transmittable in the case of optically transparent materials/devices.

Figure 2:
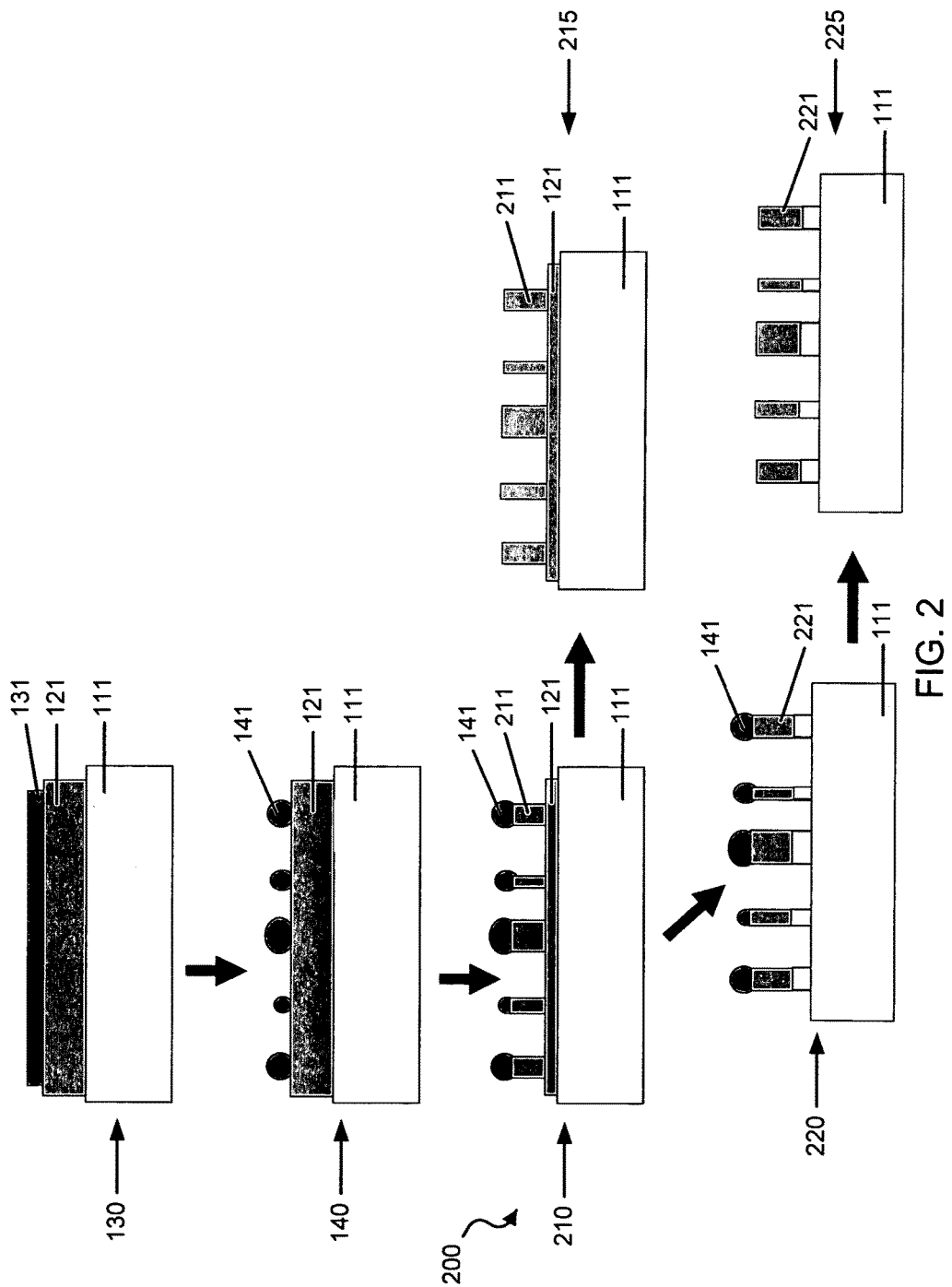
FIG. 2 shows an exemplary process to produce protruding and vertically aligned nanopillar arrays.

Implementation of process (100) can form a stable, well-defined, well-adhered, surface-reacted island array of metallic nano- or micro-structures. The exemplary metal islands can provide an improved etch mask structure that can be used to produce desired superhydrophobic or omniphobic surfaces, e.g., a surface with enhanced light transmission and absorption characteristics during subsequent etching process to define the protruding nanostructure. FIG. 2 schematically illustrates an exemplary process (200) to fabricate a protruding and vertically aligned nanopillar array. Process (200) can be implemented subsequent to the exemplary process (100). For example, process (200) can include process (210) to etch pattern the buffer layer by using reactive ion etching (RIE) and/or chemical etching using the metal islands as the etch mask to produce exemplary protruding and vertically aligned nanopillar arrays of the buffer material. FIG. 2 shows the exemplary process (210) implemented subsequent to process (140) to etch pattern buffer layer (121) using metallic etch mask island array (141) as the etch mask to produce nanopillar arrays or nanopillars (211). The subsequent etching process (210) can be used for selectively engraving the buffer layer underneath the metal islands to create an array of nanoscale pillars, e.g., nanopillars (211). The exemplary nanopillars (211) can be protruding columnar nanostructures that are vertically aligned. Process (210) includes formation of nanopillars (211) underneath the metallic etch mask structures, e.g., metallic etch mask island array (141).

The degree of etching in process (210) can be selected to be partially into the buffer layer, all the way to the bottom of the buffer layer (e.g., extending through the whole thickness of buffer layer (121)), or even extend further than the buffer layer by etching into the substrate. For example, process (210) can be implemented such that a portion or no portion of the buffer layer, e.g., buffer layer (121), remains over the substrate. In addition to or alternatively, process (200) can include process (220) to further etch the substrate underneath the buffer layer to create nanopillars that include material of the buffer layer and the substrate, e.g., nanopillars (221). For example, the exemplary process (220) can be implemented to further increase the aspect ratio of the surface nanostructure. By using the metal islands as etch mask, exemplary vertically aligned and protruding columnar nanostructured surface can be created.

Process (200) can include process (215) subsequent to process (210) to remove the metal islands, e.g. metallic etch mask island array (141), by chemical etching. For example, implementation of process (215) can result in forming a substrate featuring an array of nanopillars (211) with buffer layer (121) between the nanopillar array and the substrate (111). Alternatively, the metal islands may be left as is depending on the specific applications, thereby not implementing process (215). Process (200) can include process (225) subsequent to process (220) to remove the metal islands, e.g. metallic etch mask island array (141), by chemical etching. For example, implementation of process (225) can result in forming a substrate featuring an array of nanopillars (221). Alternatively, the metal islands may be left as is depending on the specific applications, thereby not implementing process (215).

For reactive ion etching in process (200), fluorine-based gas such as trifluoromethane gas ($CHF_3$) and argon (Ar) can be used as etching gases. The shape and length of the nanopillars of the buffer layer material can be adjusted with the time, power, and gas pressure of RIE. The conditions of RIE can be selected based on the kind of metal islands and the thickness of the buffer layer.

For example, for superhydrophobic properties, a coating of the nanostructure surface with a very thin layer of hydrophobic material can be desired. If the metal islands are removed after the patterning etch process, e.g., process (215) or process (225), and substrate (111) is an optically transparent substrate (e.g., like glass), the produced material can exhibit both self-cleaning superhydrophobic characteristics and optically transparent properties. These exemplary properties can be useful in a variety of products and applications, such as a cover glass layer or surface layer for photovoltaic solar cells, dye sensitized solar cells, thermoelectric energy conversion devices, sunlight focusing lens devices, waveguides, and other optical devices.

An example of the hydrophobic coating that can be coated on nanostructures (e.g., nanopillars (211) or nanopillars (221) in FIG. 2) may include, for example, a coating of polytetrafluoroethylene (PTFE or Teflon) by sputtering or by hot filament chemical vapor deposition. Another example can include a related polymer having $CF_3$ terminal groups, e.g., fluoropolymer or fluoroalkysilane, which may also be used as a hydrophobic coating material. Applying a self-assembly monolayer can be an effective method for various substrates, including glass, which can be applied by a vacuum deposition or a solution dip-coating deposition. Other coating methods can be used to make the substrate hydrophobic if it is chemically hydrophilic and may depend on the materials used. However, the coating may not be necessary if the substrate used is intrinsically hydrophobic. Also, a self hydrophobic surface can be obtained on the surface of nanopillar structured $SiO_2$ buffer layer during optimized reactive ion etch using fluorine-containing gas. Thus the exemplary step of adding the hydrophobic layer can be omitted for faster and more economic fabrication of self cleaning surface. The final substrate obtained through these steps can have a superhydrophobic surface with nanoscale or microscale pillars or tubular structures.

In another aspect, omniphobic articles and devices can be produced that include nanoscale or microscale surface pillar structures on any substrate surface, which can yield omniphobic or omniphobic with superhydrophobic surface properties. The exemplary articles and devices can also have enhanced light transmission and absorption characteristics, e.g., when the substrate itself is an optically transparent material.

Figure 3:
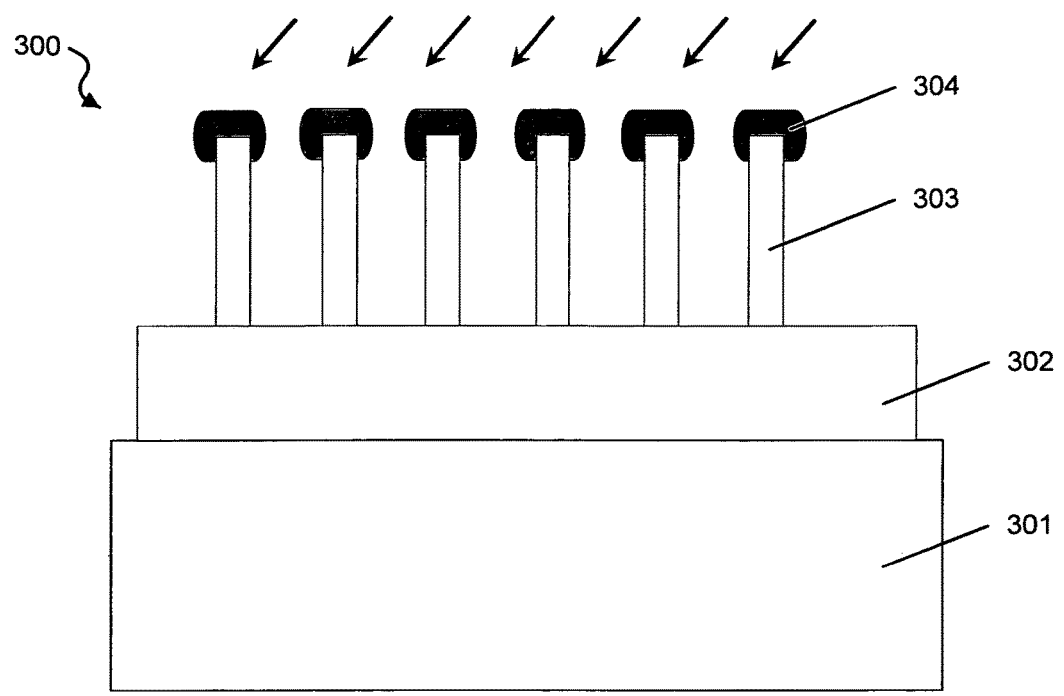
FIG. 3 shows an exemplary schematic diagram for preparation of omniphobic nanosurfaces.

For example, for omniphobic properties to provide self cleaning characteristics against aqueous solution and oily substances, a further modified nanopillar structure can be produced. An example is schematically illustrated in FIG. 3. For example, deposition of a $SiO_2$ material similar to buffer layer (121), sputter deposition of a glass material similar to the glass substrate (111), or a sputter, evaporation or dip-coating deposition of hydrophobic PTFE material itself can be selected to impart the omniphobic surface structure while maintaining the optical transparency. For applications which do not require optical transmission properties, but rather desires enhanced self-cleaning properties or increased surface area for catalyst adsorption/absorption, any metallic, ceramic, polymeric, biological or composite material can be deposited to provide both the omniphobic and enhanced functional properties.

FIG. 3 shows an exemplary schematic diagram of an exemplary omniphobic nanosurface (300), e.g., by creating a mushroom-shaped tip configuration over an array of nanostructures such as nanopillars, nanowires, or nanocones. Omniphobic nanosurface (300) can include a substrate (301), a buffer layer (302), a nanostructure array (303), and a coating material (304). Substrate (301) can be made of glass, soda lime window glass, solar cell cover glass, sapphire, silicon (Si), silicon-germanium (Si—Ge), zinc oxide (ZnO), gallium nitride (GaN), gallium arsenide (GaAs), carbon, graphite, nitride, oxide, fluoride, or any metallic, semiconductor, ceramic or some polymer surfaces, such that it can facilitate the addition of a buffer layer and surface nanopillary array. Buffer layer (302) can be a Si-containing buffer layer, e.g., Si, $SiO_2$ or silicon nitride layer. For example, buffer layer (302) can be deposited by PECVD, sputtered $SiO_2$, or other Si-based deposition+oxidation techniques. Nanostructure array (303) can include an array of Si-based nanostructures of different geometries (e.g., nanopillars, nanowires, and nanocones) and dimensions (e.g., with a 20-200 nm diameter and 50-5000 nm height). Coating material (304) can be deposited at a vertical or oblique incident to form a mushroom-like shape over the nanostructure array (303).

The exemplary omniphobic nanosurface (300) can be incorporated in articles and devices for superhydrophobic, omniphobic, light-absorbing or light-transmitting properties for a variety of applications. For example such articles or devices could be used to attach catalysts, lubricants, enzymes, chemical reactants, drug molecules, biological agents, or other compounds.

Omniphobic nanosurface (300) can be fabricated by implementing exemplary process (100) and process (200) to produce vertically oriented nanopillar arrays. Subsequently, a process that deposits silica or other ceramics, metals, alloys, polymers, Teflon, or other materials by thin film deposition on the vertically oriented nanopillar or nanotube arrays. An exemplary vertical or oblique incident deposition of coating material (304) can be performed, for example, by sputtering, evaporation, or other methods, with an optional rotation of substrate (301) during deposition of coating material (304) to form the mushroom shape tip to exhibit omniphobic properties. The exemplary mushroom shape tip configuration can enable omniphobic properties on the surface of engineered material (300).

Figure 4:
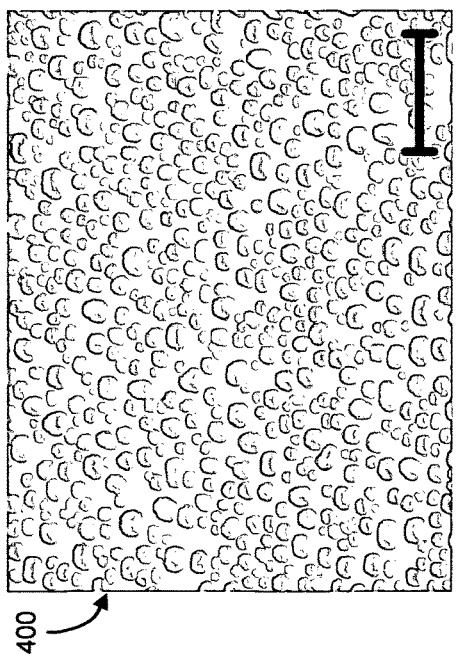
FIG. 4 is an exemplary photomicrograph of a metallic balled-up nanostructure array surface.

Examples of this embodiment of the disclosed technology are presented. For example, FIG. 4 shows an exemplary photomicrograph of a metallic balled-up nanostructure array surface (400) showing a formation of Ni islands on a sapphire substrate with a silicon dioxide buffer layer through annealing of a thin 3 nm Ni film. The scale bar shown represents 1 μm. In this example, a thin film of 3 nm thick nickel was on a sapphire (e.g., a single crystalline aluminum oxide wafer) having ~1 μm thick silicon dioxide buffer layer deposited by PECVD process. The Ni coated substrates were then heat treated at 700° C. for 1 hr. This exemplary ball-up annealing process was able to produce the Ni islands on the silicon dioxide buffer layer with the average island diameter of ~50 nm (as seen in FIG. 4).

Figure 5A:
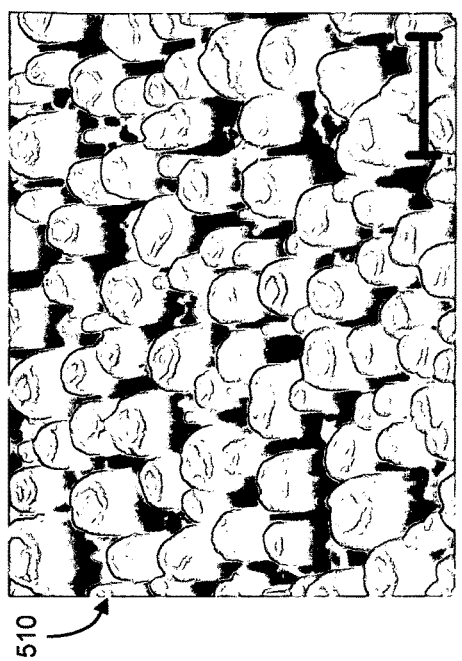
FIGS. 5A and 5B show exemplary scanning electron microscope (SEM) images of $SiO_2$ surface nanostructures on a sapphire substrate.
Figure 5C:
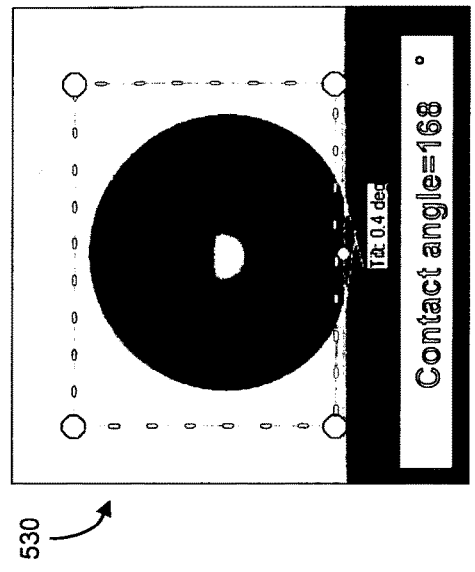
FIG. 5C depicts exemplary water droplet contact angle data showing superhydrophobic characteristics.
Figure 5B:
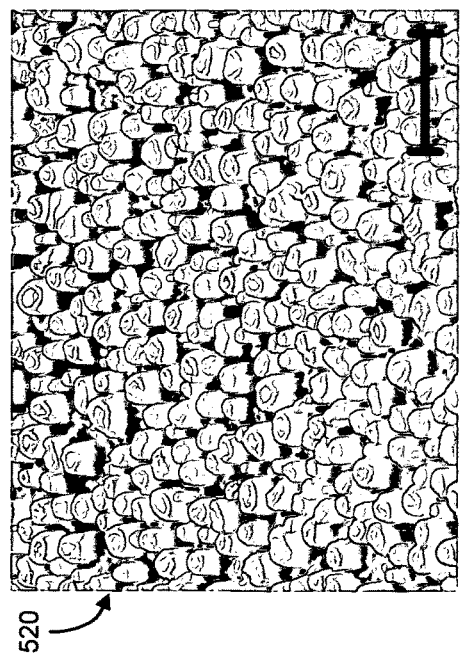

FIGS. 5A and 5B represent exemplary scanning electron microscope (SEM) images of surface nanostructures of $SiO_2$ on sapphire substrate produced by Ni film ball up and RIE etching of the $SiO_2$ buffer layer. The scale bar shown in FIG. 5A represents 500 nm; the scale bar shown in FIG. 5B represents 1 μm. The RIE treatment can be conducted using fluorine-based gases such as $CHF_3$ and Ar gas. For example, when using sapphire substrate to produce superhydrophobic surfaces, hydrophobic polymer coating may be necessary because the sapphire substrate with the silicon dioxide nanoscale pillars can be intrinsically hydrophilic. After removing Ni islands on the surface by the Ni etchant, the surface with nanoscale pillars can be subsequently coated with a hydrophobic self-assembled monolayer by a vacuum vapor deposition with a trichloro(1H, 1H, 2H, 2H-perfluorooctyl)silane. A superhydrophobic surface can be characterized with a contact angle between a drop of water and the substrate greater than 160°. FIG. 5C depicts exemplary water droplet contact angle data showing superhydrophobic characteristics, e.g., at 168°. It is noted, for example, if the Ni metal islands are removed and an optically transparent substrate like window glass is used, the final superhydrophobic substrate can be optically transparent with nanoscale pillars on the surface. The optical transparency of the $SiO_2$ pillar coated sapphire can be slightly better than the sapphire itself.

Figure 6:
FIG. 6 shows an exemplary $SiO_2$ nanostructure array surface on a soda lime glass substrate.

In another example, FIG. 6 shows an exemplary nanostructure array surface (600) of $SiO_2$ nanostructures on a soda lime glass substrate, e.g., created from 20 nm thick Ag film balled-up annealing followed by RIE etching of the $SiO_2$ buffer layer. The scale bar shown represents 500 nm. The exemplary nanostructure array surface (600) is highly superhydrophobic with a contact angle of ~160 degree, and the glass treated this way exhibited increased light transmission as compared to the original glass. In this example, a soda lime silicate glass can be first coated with a 0.5-1 μm thick silicon dioxide buffer layer by PECVD process. A thin film Ag layer of 20 nm thickness can be deposited on the glass by evaporation, and annealed at 500-550° C./2 hrs in a vacuum to form Ag islands. This exemplary annealing temperature used is below the glass transition temperature ($T_g$) of the substrate used. The exemplary annealing below the $T_g$ temperature can produce Ag island arrays on soda lime silicate glass without excessive softening or deforming of the glass. Using the Ag nano-islands as an etching mask, RIE can be performed to form a nano-pillar array structure of the silicon dioxide on the soda lime silicate glass surface (as shown in FIG. 6). Fluorine-based gases (e.g., $CHF_3$) and argon can be used as etching gases, and the shape and length of pillar can be adjusted with the time, power, and gas pressure of RIE.

Soda lime silicate glass may also benefit from hydrophobic coatings for making superhydrophobic surfaces, e.g., as soda lime silicate glass with the silicon dioxide nanoscale pillars may be intrinsically hydrophilic. After removing Ag islands on the pillar top by the Ag etchant, the surface with nanoscale pillars can be then coated with a hydrophobic self-assembled monolayer by a vacuum vapor deposition with a trichloro(1H, 1H, 2H, 2H-perfluorooctyl)silane. A superhydrophobic surface with the water drop contact angle above 160° can result.

If the Ag metal islands are removed and an optically transparent substrate like window glass is used, the final substrate can exhibit superhydrophobic properties with optical transparency actually higher than the original soda lime glass. Exemplary data is shown in FIG. 7, which shows comparative optical transmission data vs. light wavelength.

Figure 7:
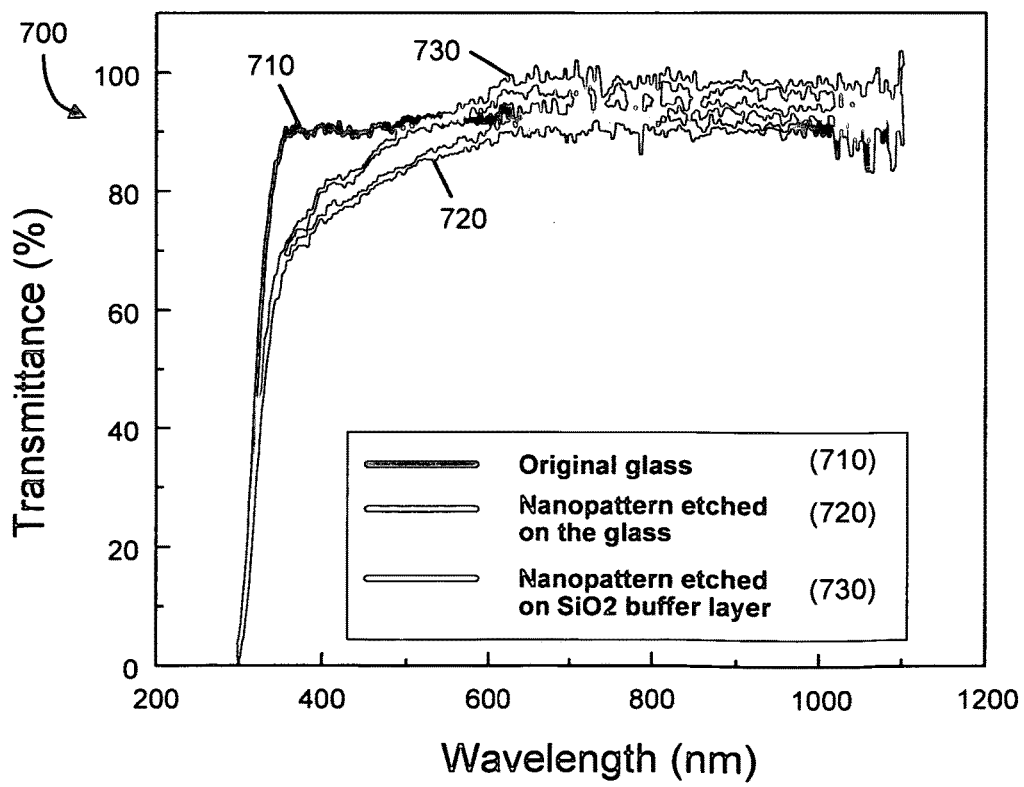
FIG. 7 shows an exemplary plot comparing optical transmission data vs. light wavelength for original glass and surface nanopatterned etched glass with and without a buffer layer.

FIG. 7 shows an exemplary plot (700) representing comparative optical transmission data vs. light wavelength for original glass (710), surface nanopatterned etched glass (720), and surface nanopatterned etched glass with $SiO_2$ buffer layer (730), e.g., ~1 μm thick from a 20 nm thick Ag film and balled-up annealing and RIE processes. As compared with original glass (710) in this exemplary experiment, surface nanopatterned glasses (720) and (730) show increased optical transparency. Surface nanopatterned glass (720) exhibited increased transmission from ~700 nm wavelength and above. Surface nanopatterned glass (730) exhibited even more pronounced optical transparency improvement from ~550 nm wavelength and above.

For example, the addition of $SiO_2$ buffer layer can enhance the aspect ratio of the surface pillar structure after RIE or chemical etching, and hence lead to improved superhydrophobic or superomniphobic properties by at least 10%, and even more preferably, by at least 20% increased contact angle. The degree of improvement can be dependent on the aspect ratio increase due to $SiO_2$ buffer layer allowing easier formation of taller pillars than many substrate materials themselves. For example, the presence of $SiO_2$ surface nanostructure in the buffer layer can also enhance the optical transparency of the substrate material such as glass, sapphire, and other ceramic crystalline or amorphous materials. The optically improved substrate can exhibit increased value of the light transparency by at least 1%, or at least 2%, or even by at least 5%, for example, measured at the wavelength of 700 nm. For example, the improved transparency property (as compared to the original flat surfaced material) can be used advantageously for applications that include enhanced energy efficiency in photovoltaic solar cells, dye sensitized solar cells, thermoelectric energy conversion devices, sunlight focusing lens devices, waveguides, and other optical devices. These exemplary applications can also benefit from the pillar structured surfaces also being self-cleaning, e.g., so that the device top glass panel surface accumulates minimal amount of sunlight-blocking dirt and other contaminants.

The enhanced surface pillar height and aspect ratio produced by the introduction of Si-containing buffer layer including $SiO_2$ layer, can also be useful for creating large surface area to attach or adhere increased amount of catalyst nanoparticles or catalyst layers for enhanced chemical reactions, in creased amount of enzymes for biological reactions, or higher-efficiency photocatalysis reactions such as water splitting, $CO_2$ decomposition, photocatalytic decomposition of waste materials, anti-bacterial photocatalytic treatments, among other examples. The enhanced optical transparency of such a substrate material can aid delivery of sunlight to more regions of two dimensional (2D) or three dimensional (3D) solar energy generating, solar energy converting, or photocatalytic device structures.

The disclosed technology can also be applicable on non-flat surface substrates and devices. For example, the buffer layer (e.g., PECVD $SiO_2$) can be deposited conformally on any curved, round, or irregular surfaces. The metal layer to be balled-up can also be deposited conformally by rotating or tilting the 2D or 3D configured substrate assembly structure.

The vertical pillar structure fabricated by metal island masked etching of $SiO_2$ buffer layer can further be modified by an exemplary dip coating technique using a polymer material, which can produce a mushroom configuration of the nanopillar tips to impart superoleophobic or superomniphobic properties. FIGS. 8A and 8B show exemplary schemes to produce re-entrant (mushroom) geometry nanopillar tips, e.g., which can impart oleophobic or omniphobic surface. FIG. 8A shows an exemplary process (800) for a tip dip-coating method. FIG. 8B shows an exemplary process (850) for a selective sidewall etching method.

In FIG. 8A, exemplary process (800) is shown as a scheme to produce re-entrant geometry nanopillar tips with oleophobic or omniphobic surface properties. For example, process (800) can employ exemplary processes (100) and (200) to produce nanopillar array (802) on substrate (801). Process (800) can include a process (810) to press the exemplary nanopillar array (802) on substrate (801) on a layer (815) over another substrate (816). Layer (815) can include silica precursor (HSQ) or polymer liquid layer spin coated on a glass substrate. Process (810) can result in nanopillar tips (825), e.g., coated polymer balls of the HSQ or polymer layer, covering the end of the nanopillar structures of nanopillar array (802). Process (800) can include a process (820) to lift the exemplary nanopillar array (802) covered by nanopillar tips (825) from layer (815). Process (820) can also include curing the nanopillar tips (825) to produce a re-entrant (mushroom) geometry nanopillar tips.

In FIG. 8B, exemplary process (850) is shown as another scheme to produce re-entrant geometry nanopillar tips with oleophobic or omniphobic surface properties. For example, process (850) can employ exemplary processes (100) and (200) to produce nanopillar array (852) on substrate (851) with metal mask islands (853) on top, e.g., by lithography or oblique incident deposition. Process (850) can include a process (860) to implement exemplary sidewall etching of the nanopillars on the nanopillar array (852), e.g., by RIE etch using a specific gas, such as $SF_6$ (Si etching gas) with reduced or no $C_4F_8$ component (sidewall passivation gas that can prevent sidewall etching). Process (860) can produce mushroom geometry nanopillar tips (863) of the sidewall-etched nanopillars (862) of the nanopillar array on substrate (851).

Figure 9:
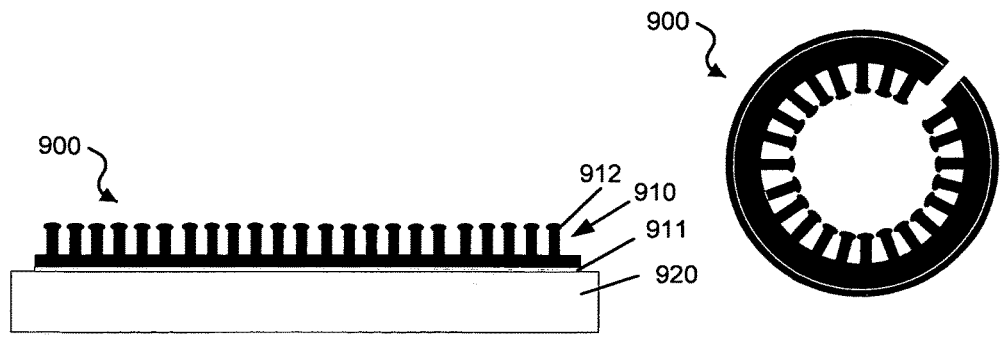
FIG. 9 shows an exemplary illustration of a superomniphobic structure.

The exemplary nanostructure layer formed in processes (800) and (850) can also be rolled up and assembled to form a superomniphobic inner wall of a tube (as shown in FIG. 9). FIG. 9 shows an exemplary superomniphobic structure (900) comprising re-entrant nanopillar arrays (910), e.g., with mushroomed-shaped nanotips (912), and a flexible substrate (911), e.g., which can be a compliant polymer or pre-wire-patterned metal foil. Structure (900) can be configured on a flat substrate (920) or in a variety of bent or curled configurations. Structure (900) can be used in a variety of applications, such as for a durable hearing aid mould.

While RIE etching can provide well controlled anisotropic etching, chemical etching can often be faster and less expensive, and hence may be sometimes preferred. For example, chemical etching can induce isotropic etching (e.g., especially for non-crystalline, amorphous material like glass). Thus, the aspect ratio of nanopillars generated by this etching process can be of the order of ~1.0. For higher aspect ratio nanopillar formation, anisotropic chemical etching can be preferred. Such desirable anisotropic chemical etching can be accomplished using directional jet flow of etchant solution, directional blow of nano- or micro-particles for sand blasting, or a mixture of liquid solution or etchant with nano/microparticles. This exemplary process is schematically illustrated in FIG. 10.

Figure 10:
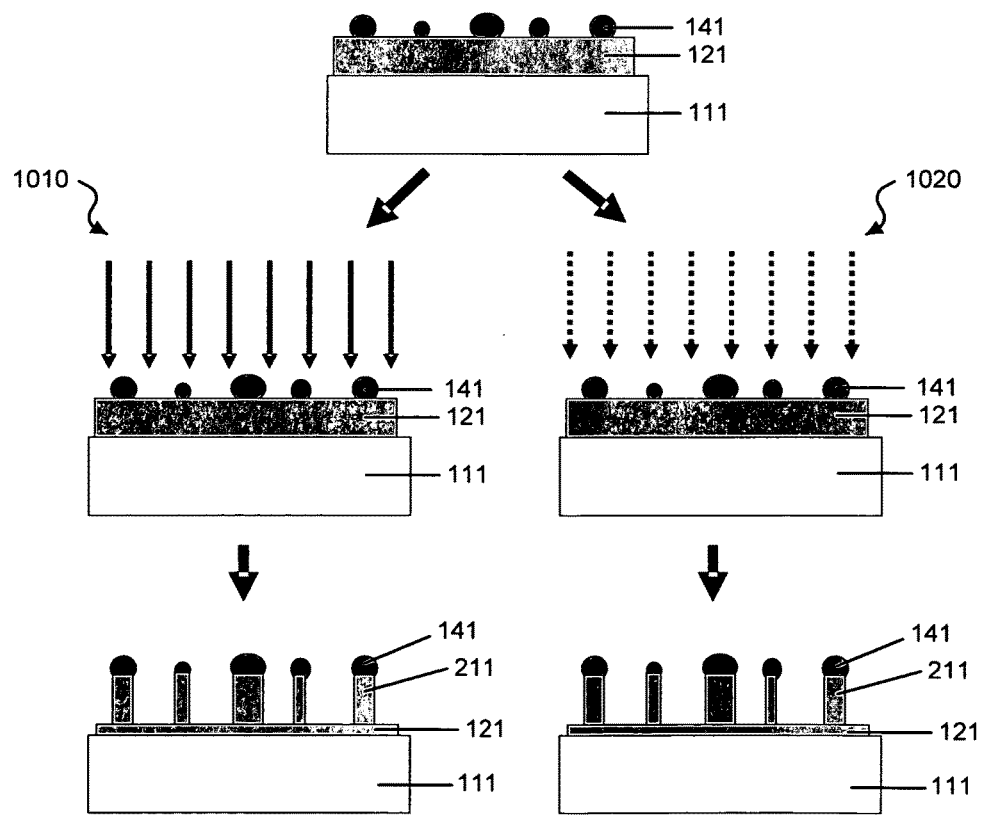
FIG. 10 shows an exemplary method of anisotropic chemical etching.

FIG. 10 shows exemplary methods of anisotropic chemical etching. In one example, process (1010) can be implemented to perform anisotropic chemical etching by directional jet flow of etchant solution. For example, process (1010) can be implemented after process (140) or process (145) previously described and shown in FIG. 1. In another example, process (1020) can be implemented to perform anisotropic chemical etching by directional blow of nano- or micro-particles for sand blasting (dry or wet), which can also include a mixture of liquid solution or etchant with nano/microparticles. For example, process (1020) can be implemented after process (140) or process (145) previously described and shown in FIG. 1. The exemplary process (1010) for directional jet flow of etchant solution may tend to provide more of the fresh etchant solution to the bottom of the etched holes (or more of the nano/micro particle blast erosion to the bottom of the etched holes in the case of process (1020) for sand-blast erosion processing) than the etched hole sidewall region, thus increasing the degree of anisotropic etching.

In another embodiment, the disclosed technology can include non-wettable, self cleaning, corrosion-resistant nano- and micro-scale paint structures.

Other than stainless steels, most metallic surfaces are prone to corrosion in environment. For example, the use of stainless steels may be too costly for many general purpose surfaces, e.g., such as surfaces found on bridge type infrastructures, some transportation pipe structures for oil, gas or water, ship decks, airplanes, automobiles, military armaments such as tanks, artilleries, and missile systems, building exterior and interior structures, etc. Thus, paint type coatings are often utilized. To protect metallic surfaces from degradation by corrosion for many applications, it can be desirable to avoid the transformational process of hydrocarbons (C—H) when exposed to thermal, chemical, biological and electrochemical environment. Therefore, it is often preferred to utilize C—F bonds rather than C—H bonds. However, the hydrophobic properties of C—F bond materials such as Teflon (PTFE) are not particularly good, e.g., with the contact angle being on the order of ~100° for a water droplet. In order to have excellent corrosion resistance, self-cleaning characteristics with a superhydrophobic water droplet contact angle of at least ~150° regime can be highly desirable.

Two different technical approaches for self-cleaning coatings can include hydrophobic and hydrophilic coatings. These two types of coatings may both be capable of self-cleaning through the action of water. However, the underlying mechanisms are different. For example, in the case of a hydrophobic surface, rolling water droplets can take away dirt and dust. In the case of hydrophilic surfaces, sheeting water can carry away dirt.

FIGS. 11A-11C show exemplary illustrations of water drop contact angles on hydrophilic (FIG. 11A), hydrophobic (FIG. 11B), and superhydrophobic surfaces (FIG. 11C). FIG. 11D shows exemplary illustration of surface protruding nanostructures that can induce superhydrophobic characteristics, such as those seen in FIG. 11C.

Hydrophilic coatings, such as a $TiO_2$ type material, can have an additional property of photocatalytic breakdown of adsorbed organic dirt by ultraviolet (UV), e.g., from sunlight illumination in nature, which can then be washed away when it rains. The electrons and holes from the charge separation induced by sunlight can react with oxygen molecules, hydrogen and water to form a superoxide and other radical species. However, in general, hydrophobic coatings are more proactive measures that prevent the accumulation of corrosion-inducing liquid and moisture in the first place.

For example, the self-cleaning action of hydrophobic coatings (commonly known as the "Lotus Effect") can arise from their high water-contact angles. If a contact angle ($\theta_c$) is very high, i.e., $\theta_c$>150°, the surface is referred to as superhydrophobic. In the Cassie-Baxter Model (also referred to as the "air pocket model"), the presence of a two-phased surface is assumed, with one of the phases being air. This can be likened to air trapped below the water drop, with the water drop sitting mostly on air, leading to a superhydrophobic behavior. The Cassie-Baxter Model can be represented by Eq. (1):

$$\cos \theta_c = f_1 \cos \theta_1 + f_2 \cos \theta_2 \quad (1)$$

where $\theta_c$ represents the apparent contact angle of the liquid droplet; $f_1$ and $f_2$ represent the projected area fraction of phase 1 (e.g., water) and phase 2 (e.g., air), respectively; and the angles $\theta_1$ and $\theta_2$ represent the equilibrium contact angle of the droplet on flat surface of the phase 1 and phase 2 material, respectively. Since the water contact angle $\theta_2$ in air is 180° (non-wetting), $\cos \theta_2 = -1$. Together with the relationship of $f_1+f_2=1$, Eq. (1) can be modified to become Eq. (2):

$$\cos \theta_c = f_1(\cos \theta_1 + 1) - 1 \quad (2)$$

If $f_1$ is very small, like a sharp needle array or a nanopillar array a lot of air shall exist under the water droplet, as illustrated in FIG. 11D, and $\cos \theta_c$ can approach -1 with the water droplet contact angle $\theta_c$ becoming close to 180° in the case of superhydrophobic surface. Such surface nanostructure can induce superhydrophobic surfaces with excellent contact angles of greater than ~170° for an exemplary Si nanowire array and $Al_2O_3$ nanowire array.

For example, by utilizing a film of chemically hydrophobic materials such as fluorinated polymers (e.g., PTFE), the contact angle can be made in the range of 90-130°. However, the contact angles of flat polymer layers are not high enough to cause the rolling motion necessary for true self-cleaning. Geometrical surface roughness is essential to impart superhydrophobicity, even for PTFE coated surfaces.

The disclosed technology can include a nano-patterned superhydrophobic coating, which is also referred to as nano-patterned superhydrophobic paint. The exemplary nano-patterned superhydrophobic paint can be used, for example, as a coating with anti-corrosion properties, in which adhesion and corrosive reactions with water can be minimized. For example, the disclosed superhydrophobic paint can be used on large-size structures, e.g., outdoor infrastructures, vehicles, airplanes and ships (military and civilian), as well as building exterior and interior structures.

The exemplary superhydrophobic paint can be applied to such structures by practical and inexpensive means. For example, painting is a well established, low-cost process often used for various structures including bridges and transportation vehicles for protection against corrosion (as well as decorative purposes). In an exemplary approach, a common paint can first be applied on the desired surface (e.g., metallic surface or other surfaces including wooden or ceramic surface that can also be prone to the moisture-induced deterioration), and then a roller-type nano-pattern inducing device can be employed for rapid formation of the superhydrophobic paint on the surface. These exemplary processes and structures are described.

FIG. 12 shows an exemplary process to produce a nano-patterned superhydrophobic surface. Process (1210) can include making a press-imprint on a partially dry common paint (1213) over a surface (1214) with a flat or roller stamp, e.g., imprint mould (1211), having surface nanopillar tips (1212). The surface to be coated, e.g., surface (1214), can include a corrosive metallic surface, or other surfaces including wooden or ceramic surface. Process (1210) can include introducing surface nanostructures on the surface of paint (1213). Process (1220) can include releasing the mould (1211) from the partially dried paint, which can result in an imprinted surface (1224). Process (1230) can include applying a thin coating (1231), e.g., a coating of PTFE, to make the surface superhydrophobic. The thin coating (1231) can be applied after the paint (1213) is dried.

Figure 13:
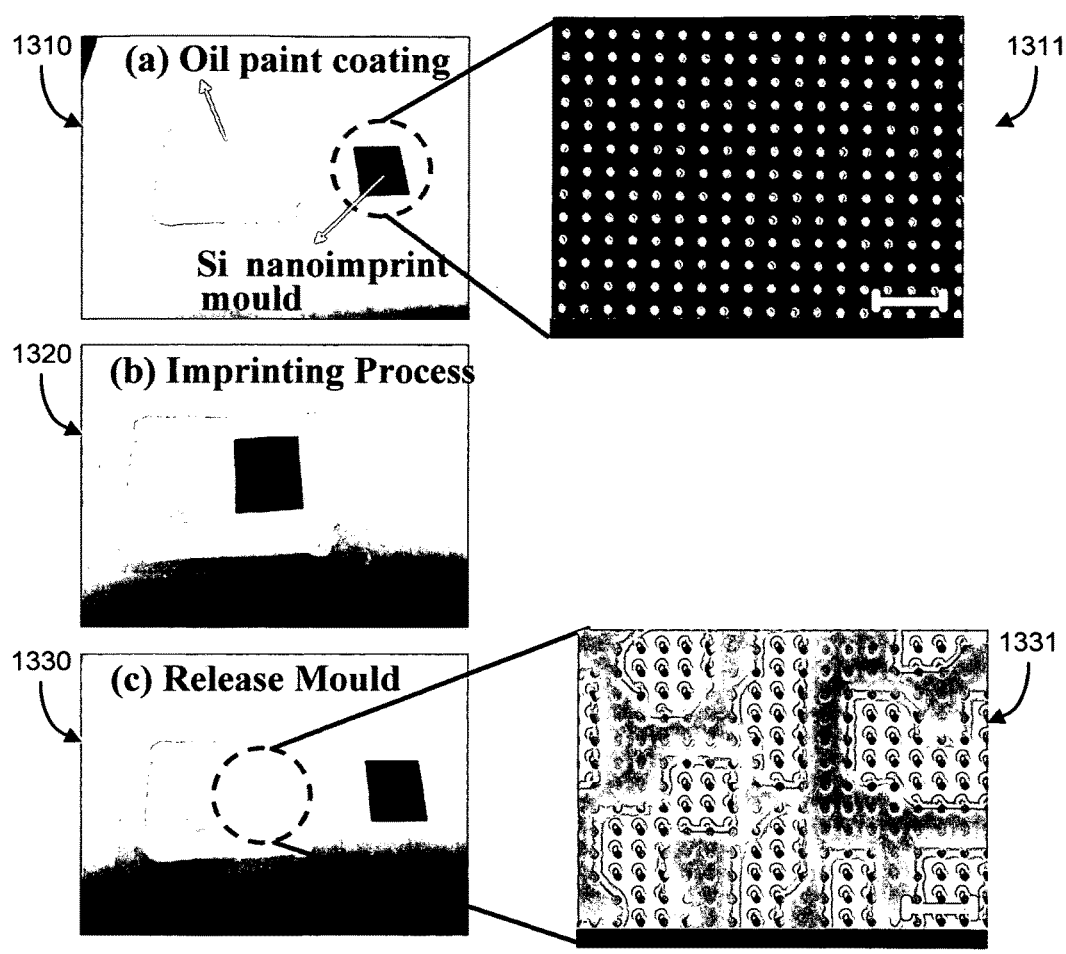
FIG. 13 shows an exemplary demonstration of a process to produce a nano-patterned superhydrophobic surface.

An exemplary demonstration of disclosed technology is described. FIG. 13 shows an exemplary demonstration of processes (1210), (1220) and (1230) in exhibits (1310), (1320), and (1330), respectively. Exhibit (1310) shows an exemplary oil paint on a glass surface applied by common brush painting (acrylic latex based exterior paint with a white color) and an exemplary mould like the nano-patterned imprint stamp (1211) in FIG. 12. Exhibit (1311) shows a high magnification micrograph image of the mould, which includes an array of Teflon coated Si-based nanopillars with 250 nm diameter and 300 nm height. Exhibit (1320) demonstrates process (1220) of pressing the Si nanoimprint mould onto the coated paint before it is completely dried, which was subsequently removed as shown in exhibit (1330). Exhibit (1331) shows a high magnification micrograph image of the oil pant coating after press imprinting. After air drying, the paint surface exhibited an imprinted nanostructure as shown in the SEM micrograph, in which the replicated image of a few hundred nanometer sized nanostructure is shown from the paint surface. Also, the omniphobic surface coating on the Si mould surface (e.g., using PTFE coating) enabled the Si mould to be released cleanly with no trace of the paint remnant on its surface. The scale bar represents 2 μm in exhibits (1311) and (1331).

The disclosed omniphobic surface treatment is highly desirable for paint surface nano-patterning. In addition to the PTFE type coating, other suitable surface coating materials to be applied on the surface of nanostructures, according to the disclosure, include palladium (Pd) and ultra-high-molecular weight polyethylene. Also, in addition to solid (nano-imprint moulds) stamps for the exemplary nano-imprinting process, a mechanically compliant stamp such as made of rubber, e.g., a PDMS-based elastomeric mould with nano-patterns, can be desirable for general imprinting because of the 'real-life' topographic ups and downs of surface roughness. For example, 200 nm nanostructures with a surface roughness in the few hundred nanometer range would not allow a uniform stamping if the mould is solid and flat. Thus, it can be important to employ a flexible elastomeric mould in this exemplary situation. With its mechanically compliant nature, an exemplary flexible elastomeric mould can allow a more reproducible and scalable nano-imprinting on macroscopically non-smooth surfaces.

As aforementioned, the paint does not stick to the exemplary PDMS mould surface after nano-imprinting patterning. As shown in the example in FIG. 13, once the paint is dried, a hydrophobic coating of —C—F— based layer was applied, e.g., ~10-20 nm thick PTFE layer (2% AF1601 liquid Teflon solution (DuPont), after pretreatment with fluorosilane for adhesion enhancement). Other fluorine-containing hydrophobic coating material, such as sputter-deposited Teflon, trichlorosilane, or fluoroalkylsilane (FAS) type coating of trimethoxylsilane in methanol solvent may also be utilized.

Figure 14:
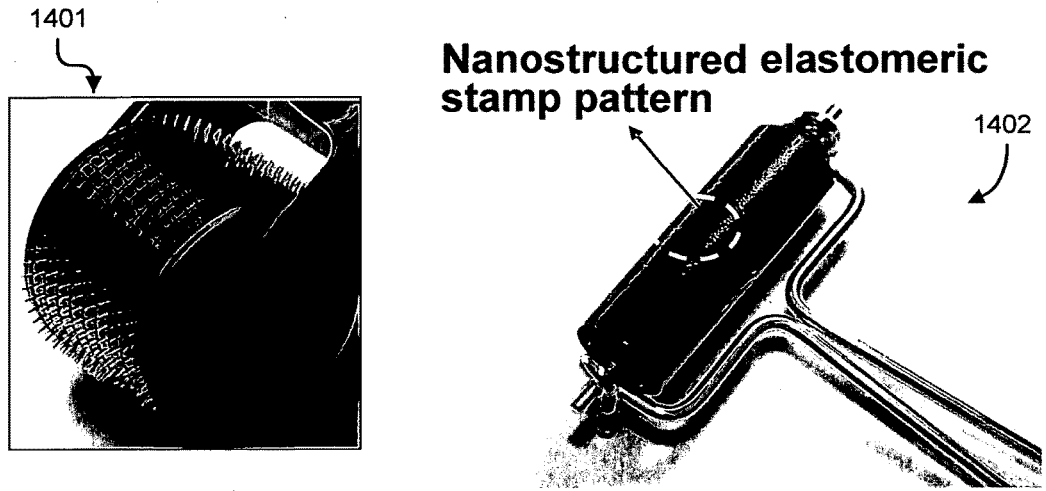
FIG. 14 shows exemplary roller imprinting moulds.

While a flat imprint mould was use for the demonstration in FIG. 13, a roller-type imprinting mould can also be used. FIG. 14 shows examples of roller imprinting moulds that could be used with the disclosed technology to generate rapid nanopatterns. FIG. 14 shows an exemplary roller-type geometry imprinting mould (1401) and another exemplary roller-type geometry imprinting mould (1402) with a different roller shape. The nanostructured elastomeric stamp pattern could be incorporated in mould structure of roller (1401) and roller (1402). Exemplary roller imprinting moulds (1401) and (1402) can increase high throughput of creating the nano-pattern imprint, as described in process (1210). Such processing is likely to be relatively inexpensive. A variety of mould pattern can be utilized. For example, a two-step roller imprinting such as crisscross patterning can also be employed to make the nanostructure sharper than just a line array pattern.

Figure 15:
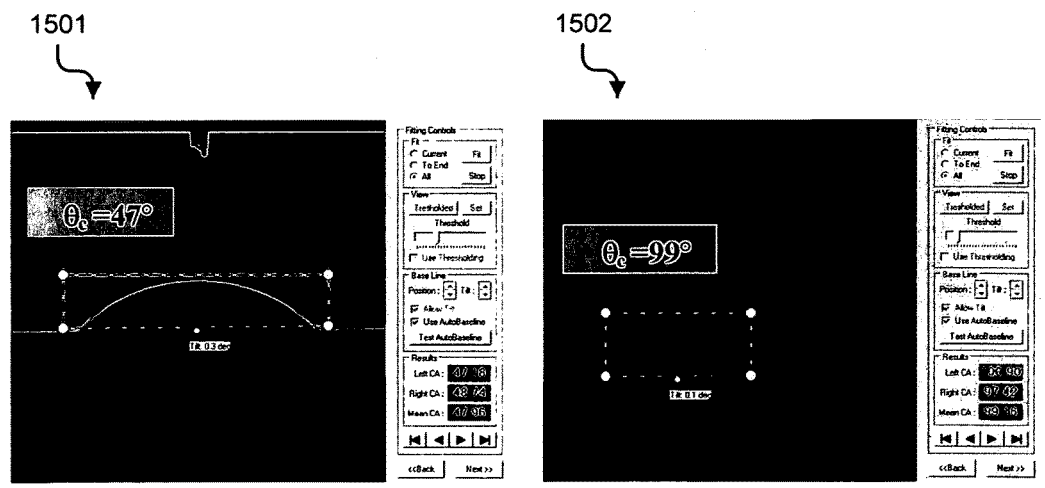
FIG. 15 shows exemplary contact angle evaluations of Si surfaces without and with a Teflon coating.
Figure 16:
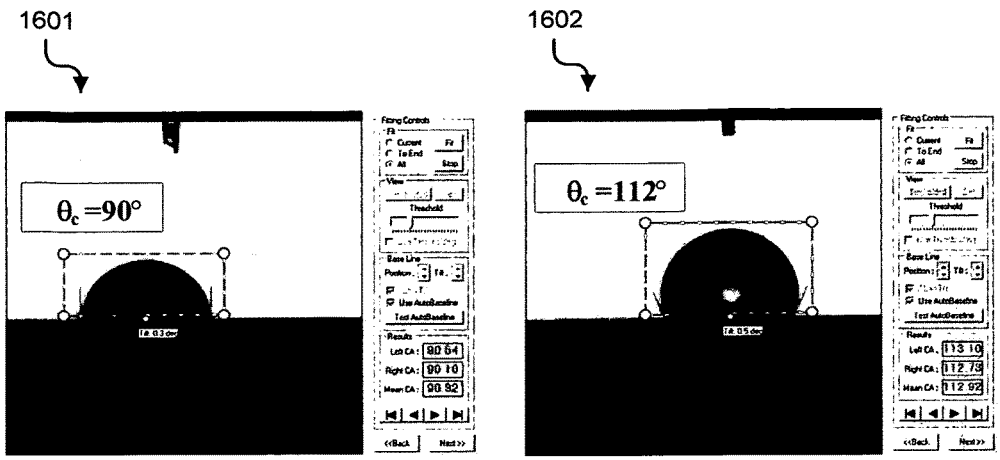
FIG. 16 shows exemplary contact angle evaluations of flat paint surfaces without and with a Teflon coating.

The effect of PTFE coating (e.g., 2% AF1601, DuPont) on water droplet contact angle was evaluated via comparative contact angle measurements. For hydrophobicity angle measurements, a contact-angle goniometer (CAM100, KSV instruments) was used. FIG. 15 shows the water droplet contact angle evaluation of plain Si surface (1501) vs. Teflon-coated Si surface (1502). The exemplary Si surface (1501) exhibited a 47° contact angle, and the exemplary Teflon-coated Si surface (1502) exhibited a 99° contact angle. FIG. 16 shows the water droplet contact angle evaluation of flat paint surface (1601) vs. Teflon coated paint surface (1602). The exemplary flat paint surface (1601) exhibited a 90° contact angle, and the exemplary Teflon coated paint surface (1602) exhibited a 112° contact angle. As indicated by the data in FIGS. 15 and 16, while the contact angle improves with the Teflon coating from ~47° to ~99° on Si surface, and from ~90° to 112° on the paint surface to be hydrophobic, these exemplary surfaces are not superhydrophobic surfaces. Further surface modifications, such as nanostructures and techniques of the disclosed technology, can be employed to make the surface truly superhydrophobic.

Figure 17:
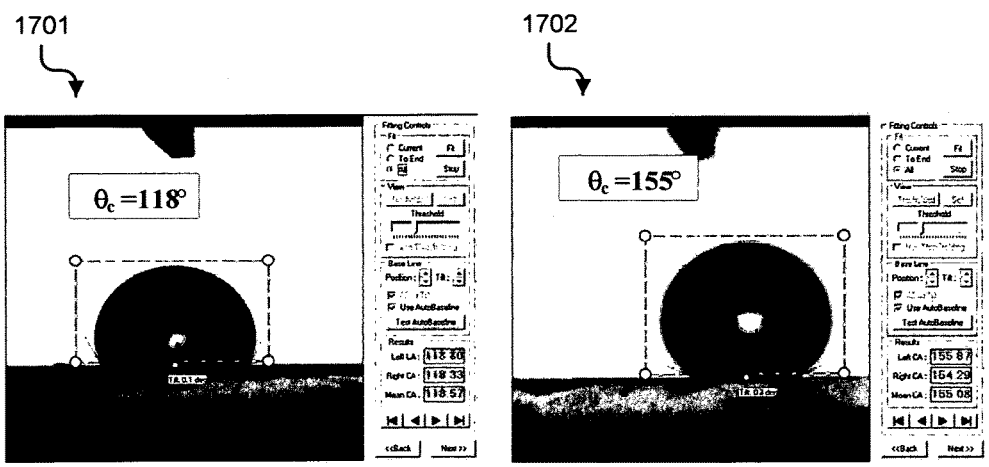
FIG. 17 shows exemplary contact angle evaluations of nano-patterned paint surfaces without a Teflon coating and with a Teflon coating.

For example, the exemplary nano-patterned superhydrophobic paint shown and described in FIGS. 12 and 13, after drying, exhibited an excellent contact angle of 155° (as compared to the relatively poor contact angle of only 112° for the PTFE coated flat paint surface with no nanostructures shown in FIG. 16). The contact angle measurement data for the exemplary nano-patterned paint shown presented in FIG. 17. FIG. 17 shows the water droplet contact angle evaluation of nano-patterned paint without a Teflon coating surface (1701) vs. nano-patterned paint with a Teflon coating surface (1702). The exemplary nano-patterned paint without a Teflon coating surface (1701) exhibited a 118° contact angle (hydrophobic), and the exemplary nano-patterned paint with a Teflon coating surface (1702) exhibited a 155° contact angle (superhydrophobic). The exemplary superhydrophobic paint coating can be applied to bulky surfaces of metallic structures such as infrastructures of bridges and buildings, transportation vehicles such as airplanes and ships, tanks, etc for significantly improved anti-corrosion protection.

Figure 18:
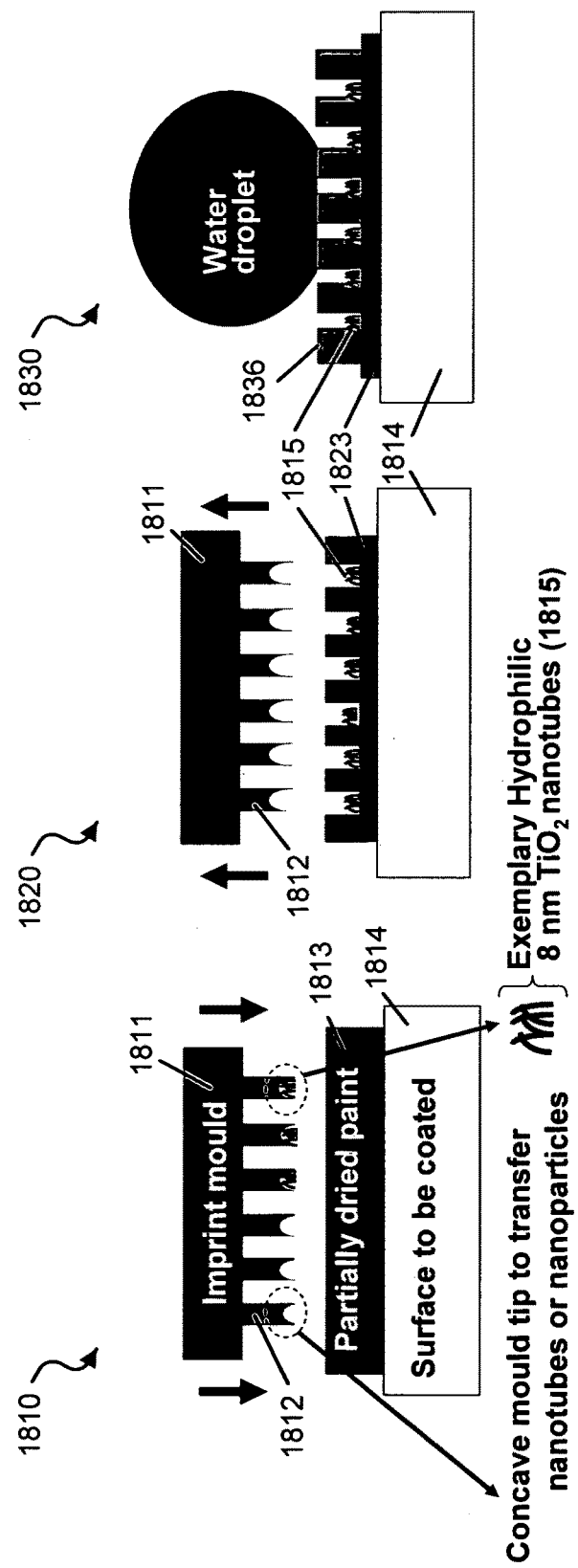
FIG. 18 shows an exemplary process to produce a dual structure nano-patterned superhydrophobic surface with photocatalytic properties.

In another aspect of this embodiment of the disclosed technology, the nano-patterned paint can include the ability to impart an enhanced self-cleaning feature to the applied surface while avoiding its own degradation. For example, the nano-patterned paint can provide an ability to photo-generate very reactive oxygen species from air. Thus, a dual structure of having both superhydrophobic surface properties and photocatalytic characteristics can be selected. For example, $TiO_2$ is a known photocatalyst capable of generating super oxide as well as peroxyl and hydroxyl radicals for decomposition of organic contaminants. The photocatalysis of $TiO_2$ can occur at the near UV region (e.g., 3.2 eV). $WO_3$ and other doping additions can broaden the photocatalysis spectrum range to longer wavelength regions toward visible region (2.5 eV). For imparting photocatalytic properties to the nanopatterned superhydrophobic paint, the disclosed technology can include a unique dual structure of the described superhydrophobic structure (e.g., in the form of the exemplary protruding nanopillar or nanopore configuration) and photocatalytic $TiO_2$ nanoparticles included as a part of the nanostructure. For example, ~10-20 nm diameter $TiO_2$ nanoparticles can be placed in the valley bottom of the nanopatterned paint surface, which can avoid interference with the superhydrophobic water repelling behavior, yet still serve as a photocatalyst. An example is schematically illustrated in FIG. 18. The nano-imprint mould tip can be modified to have concave crater array, which can pick up a paste of $TiO_2$ nanoparticles or nanotubes and deliver to the paint valley regions.

FIG. 18 shows an exemplary process to produce a dual structure nano-patterned superhydrophobic surface with photocatalytic properties. Process (1810) can include making a press-imprint on a partially dry paint (1813) over a surface (1814) to be coated with a flat or roller stamp, e.g., imprint mould (1811), having an array of nano-sized pillars, tubes, or particles (1812). The surface (1814) to be coated can include a corrosive metallic surface, or other surfaces including wooden or ceramic surface. The exemplary nanopillars (1812) can be configured to have concave-shaped tips that can embed nanoparticles, nanotubes, or other nanostructures having photocatalytic properties, e.g., exemplary hydrophilic $TiO_2$ nanotubes (1815), which can be deposited into the imprinted surface. Process (1820) can include releasing the mould (1811) from the partially dried paint (1813), which can result in an imprinted surface (1823). Imprinted surface (1823) can include nano-sized cavities that can receive and contain deposited nanoparticles, nanotubes, or other nanostructures, e.g., nanotubes (1815). Process (1830) can include applying a thin coating (1836), e.g., a coating of PTFE, to make the surface superhydrophobic. For example, the surface can include a superhydrophobic coating on protruding portion of the nano-patterned surface, in which the protruding tip is superhydrophobic while the valleys contain photocatalyst material. Thin coating (1836) can be applied after the paint (1813) is dried.

Another exemplary technique to impart the photocatalytic properties to the superhydrophobic paint surface can include utilizing photocatalytic nanoparticles (e.g., $TiO_2$ nanoparticles) already embedded as a part of a paint (e.g., to provide white color or to control the viscosity). Exemplary superhydrophobic paint structures have been shown in FIGS. 12, 13 and 17. Another exemplary technique can employ a surface removal process to partially expose the bare $TiO_2$ surface, e.g., by laser ablation with scanning laser beam or a mild mechanical abrasion, to partially remove the surface paint molecules. In this example, a portion of the surface is paint-removed and bare $TiO_2$ nanoparticle are exposed, which can serve as photocatalyst, while also $TiO_2$ can be paint-covered with a fluorine-containing hydrophobic coating material (e.g., PTFE) that can serve as water-repelling superhydrophobic surface, thus enabling the dual-function structure.

In another embodiment, the disclosed technology can include self-cleaning solar cell glass structures.

Solar cell panels can include a glass cover (referred to as "solar glass" herein) that can protect the active solar cell semiconductor layer underneath. It is desirable for solar glass to allow sunlight to penetrate with minimal light loss. For this purpose, solar glass should have a minimal reflectivity of sunlight. For example, a porous, yet optically transparent glass or silica structure can have the desirable substantially reduced light reflectivity. However, with continued use of solar cells for many months and years, solar glass tends to get dirty with an accumulation of dirt. The accumulation of dirt and other sunlight-blocking substances can reduce the light transmission, thus requiring cleaning of the surface, which can be time consuming and expensive.

The disclosed technology can provide the capabilities to impart self-cleaning surface characteristics to the solar glass surface. The disclosed technology can include surface structures with superomniphobic surface properties, which includes superhydrophobic and superoleophobic properties. For example, surface nanostructure can be combined with porous glass or silica structures to impart both strong light absorption and optical transparency. For minimal reduction in light transmission and desired transparency of the solar glass, topographic nanofeatures can be introduced that have a dimension well below the wavelength of the light involved. For example, in case of a photovoltaic solar cell, the wavelength can be from approximately UV to approximately IR spectrum. Thus, the exemplary nanostructure that is introduced in this example can have a dimension of ~150 nm or smaller. Disclosed are processes to produce the exemplary superomniphobic surfaces with enhanced light transparency, e.g., on solar glass.

FIG. 19 shows an exemplary structure and method for fabricating self-cleaning solar glass surface nanostructures. The method of fabrication can include applying a nanoparticle paste/slurry coating onto a solar glass substrate, making an imprint using a rigid or elastomeric stamp mould before complete cure of the nanoparticle paste/slurry (or after cure, if the matrix is an imprintable thermoplastic), and completing the curing/drying, followed by surface coating with fluorine-containing hydrophobic layer. Referring to FIG. 19, process (1910) can include coating a solar glass substrate (1912) with a coating layer (1911), which can include a paste/slurry containing transparent glass, silica and/or titania nanoparticles mixed with transparent matrix polymer liquid and some binder, solvent or water as needed for specific polymer material. For example, a transparent polymer can be poly(methylmethacrylate) (PMMA) diluted with acetone or hydrogen silsesquioxane (HSQ) polymer, which is a precursor that can further be converted into almost pure silica by a low temperature baking or plasma treatment. The removal of matrix liquid, such as a solvent or water, can produce additional nanopores if processed relatively rapidly to minimize equilibrating of drying process. The glass, silica or titania nanoparticles can be configured to a desired dimension, e.g., in the range of 2-100 nm average diameter and 0.1-10 μm thickness. Coating layer (1911) can be coated in process (1910) as a uniform layer by using a doctor blade coating, squeeze coating, spin coating, brush coating or spray coating.

Process (1920) can include imprinting a nano-pattern on the coating layer (1911), e.g., by using an imprint mould stamp (1913), which has a nano-pattern array, e.g., of ~150 nm or smaller feature size nanostructures. Process (1920) can be implemented before complete cure of coating layer (1911), e.g., when the paste still contains the solvent or water and is still somewhat wet and compression deformable, or after coating layer (1911) is completely dried/cured, e.g., if the matrix is an imprintable thermoplastic. Imprint mould stamp (1913) can include a rigid or elastomeric stamp mould.

After coating layer (1911) is completely cured/dried, a hydrophobic coating (1933), e.g., fluorine-containing molecules or high-molecular-weight ethylene like molecules, can be added in process (1930). Process (1930) can include adding the hydrophobic coating (1933) by sputtering, evaporation or by using a liquid precursor solution (that can be dried at ambient or at relatively low temperature) to make the nanopatterned solar glass surface superhydrophobic or superomniphobic having self-cleaning properties. For example, hydrophobic coating (1933) can include fluorine-containing hydrophobic coating material include PTFE coating or FAS type coating of trimethoxylsilane in methanol solvent. Process (1930) can also include applying a liquid PTFE coating (e.g., 2% AF1601 from DuPont) followed by drying operation.

FIG. 20 shows another exemplary method to fabricate a superhydrophobic, self-cleaning solar glass surface. For example, self-cleaning solar glass surface nanostructures can be applied by implementing process (2010), which can include making an imprint of a nano-pattern using an imprint mould stamp (2013) on a glass or silica precursor coating layer (2011) that covers the surface of a solar glass substrate (2012). Before process (2010), a solar glass surface (e.g., solar glass substrate (2012)) can be coated with a precursor coating layer (2011), e.g., which can be made of a precursor liquid of HSQ or organisilicate liquid. Imprint mould stamp (2013) can be a rigid or elastomeric mould stamp. Process (2010) can be implemented before complete cure of precursor coating layer (2011), or process (2010) can be implemented after cure of precursor coating layer (2011) if the matrix is an imprintable thermoplastic. Process (2020) can include releasing the imprint mould stamp (2013) from the precursor coating layer (2011) to form a nano-patterned topographic structure (2021). Process (2030) can include drying/curing of the precursor to produce nanoporous, nano-patterned layer (e.g., nano-patterned topographic structure (2021)), which can be followed by applying a surface coating (2033), e.g., a fluorine-containing hydrophobic layer. Process (2030) can include an optional baking step to dry/cure the imprinted precursor coating layer (2021).

Figure 21:
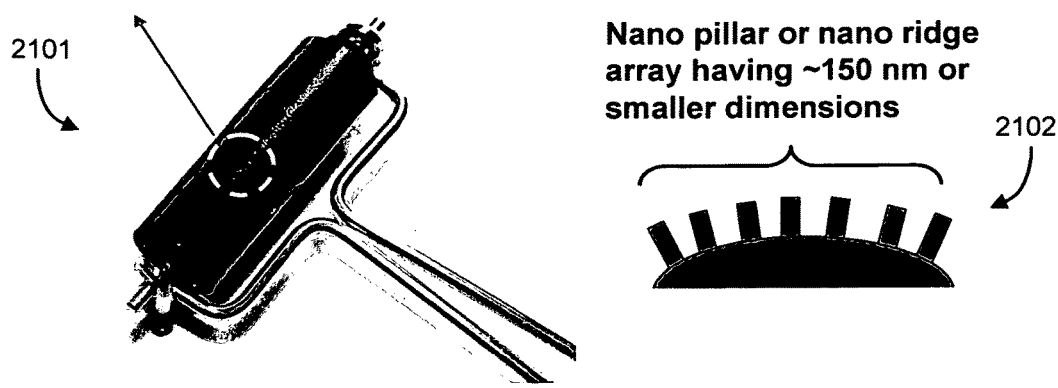
FIG. 21 shows an exemplary roller imprinter geometry.

Exemplary nano imprinting can be performed by either flat rigid stamp mould or an elastomeric compliant mould for the ease of stamping on real-life rough surface. FIG. 21 shows an exemplary roller imprinter geometry (2102) having protruding surface nano needle array for roll imprinting onto semi-dried precursor silica or glass particle-containing liquid layer before complete drying. The exemplary protruding surface nano needle array pattern could be incorporated in a roller (2101). Alternatively, the precursor can be silica or glass nanoparticles in a solidified transparent thermoplastic polymer with glass transition temperature below 200° C. for easy nano-imprinting. The nano pillars or crisscross nano ridges on the roller can be pre-coated with Teflon (or other fluorine-containing material, e.g., trichlorosilane) for non-sticky characteristics. Two step nano imprinting with roller stamp can also be optional, e.g., to generate more complex or sharper pillar-like nanopatterns for improved non-wetting characteristics.

Such transparent, superhydrophobic and mechanically durable inorganic coatings can be implemented for protecting solar cell glasses, e.g., which can include photovoltaic solar cell assembly by self-cleaning properties. The exemplary self-cleaning properties may require no or minimal need for user cleaning to remove dirt and other surface contaminants. For example, the superomniphobic solar cell surface can significantly increase the long-term solarcell efficiency with reduced maintenance expenses.

In another embodiment, the disclosed technology can include high-aspect-ratio and extremely small titania nanotubes to enhance superhydrophobic or omniphobic surface properties.

Figure 22:
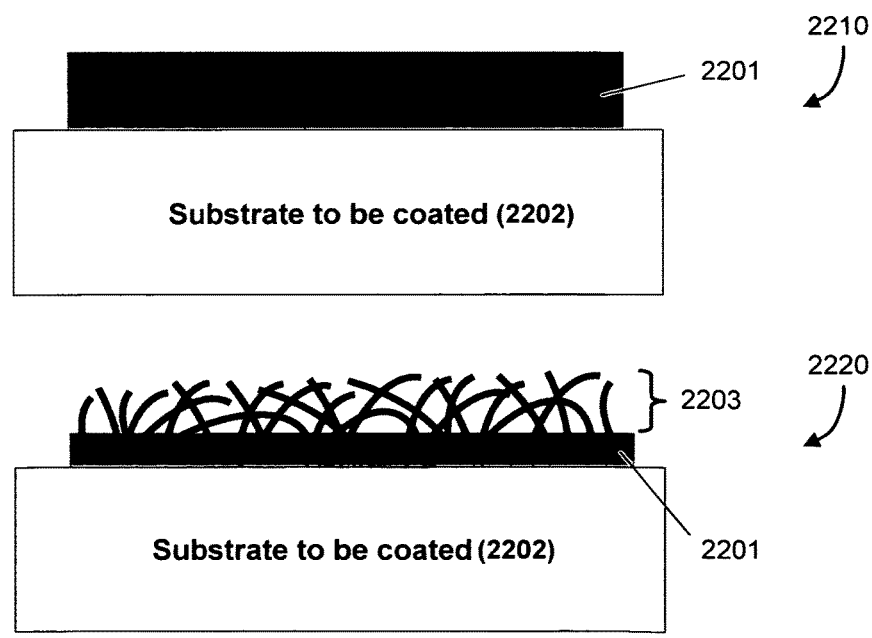
FIG. 22 shows an exemplary process to develop superhydrophobic or omniphobic surfaces using nanotube structures on a substrate.

FIG. 22 shows an exemplary schematic illustration of a process to develop superhydrophobic or omniphobic surfaces using extremely fine diameter (e.g., ~10 nm) nanotube structures on a substrate, e.g., 8 nm diameter $TiO_2$ nanotube formations on Ti metal surface by hydrothermal process. For example, process (2210) can include depositing a Ti metal thin film (2201) onto a substrate (2202). Subsequent to implementing process (2210), process (2220) can be implemented, which can include forming protruding, extremely fine $TiO_2$ nanotube structures (2203) from Ti metal thin film (2201), e.g., by hydrothermal heat treatment at ~100-200° C. Process (2220) can include forming the exemplary protruding $TiO_2$ nanotubes (2203) by directly growing or etch-forming on the Ti metal layer (2201) surface, e.g., by hydrothermal process. An exemplary hydrothermal process to form the exemplary 8 nm diameter $TiO_2$ nanotube structures can include immersing Ti metal surface into 10 M aqueous NaOH solution, heated at 120° C. for 30 min in a PTFE-lined autoclave, and subsequently washing the surface with 0.1 M $HNO_3$ aqueous solution and deionized water. After air drying, the samples can be annealed in air at 500° C. for 1 hr to transform the as-fabricated $TiO_2$ nanotubes to the anatase $TiO_2$ phase.

FIGS. 23A-23C show exemplary scanning electron microscope (SEM) and transmission electron microscope (TEM) images of exemplary $TiO_2$ nanotube structures. FIG. 23A shows a top view SEM image (2310) vertically aligned $TiO_2$ nanotube arrays, and FIG. 23B shows a cross-sectional view SEM image (2320) of vertically aligned $TiO_2$ nanotube arrays. FIG. 23C shows TEM micrograph (2330) showing the multi-wall nature of the exemplary ~8 nm diameter $TiO_2$ nanotubes.

These structures can exhibit very good non-wetting properties when coated with Teflon type fluorine-containing layer. For example, when the nanotube structure is combined with microscale surface roughness, even further improved superhydrophobic and superoleophobic properties can be obtained. FIG. 24 shows an exemplary schematic representation of superhydrophobic/omniphobic flat surface (2410), which can be hydrothermally processed by implementing processes (2210) and (2220) to form ~8 nm diameter $TiO_2$ nanotube structures on a Ti substrate (e.g., foil). FIG. 24 also shows an exemplary schematic representation of superhydrophobic/omniphobic micro-roughness surface (2420), which exhibits a micro-textured surface and is hydrothermally processed to form exemplary protruding nanotube structures.

Figure 25:
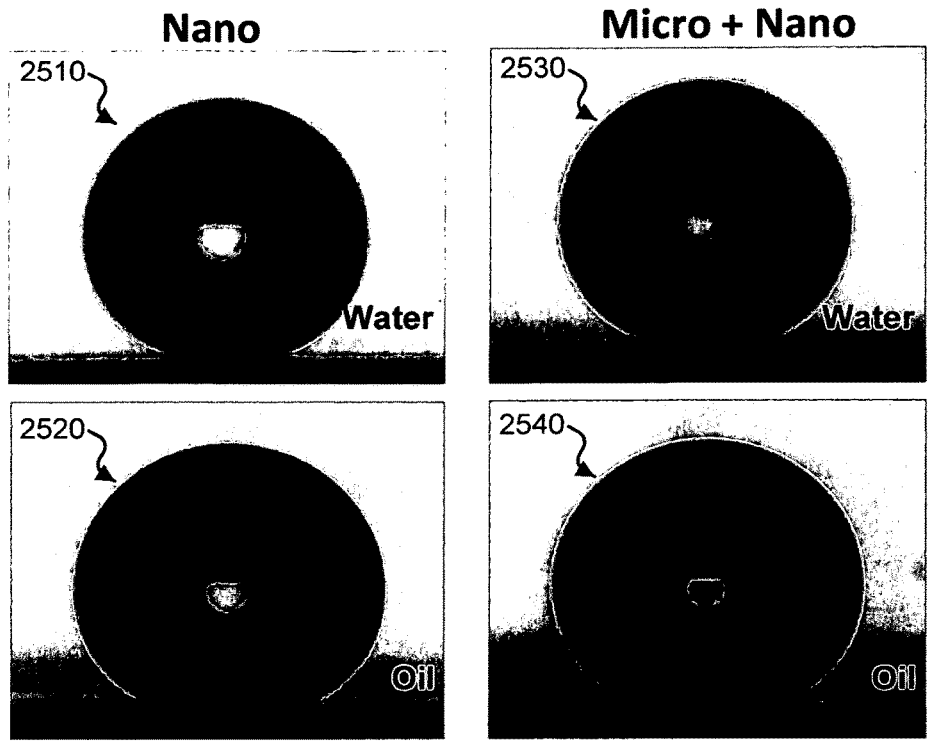
FIG. 25 shows exemplary images featuring water and oil droplets on flat and micro-rough surfaces modified with $TiO_2$ nanotube surface structures.
Figure 26:
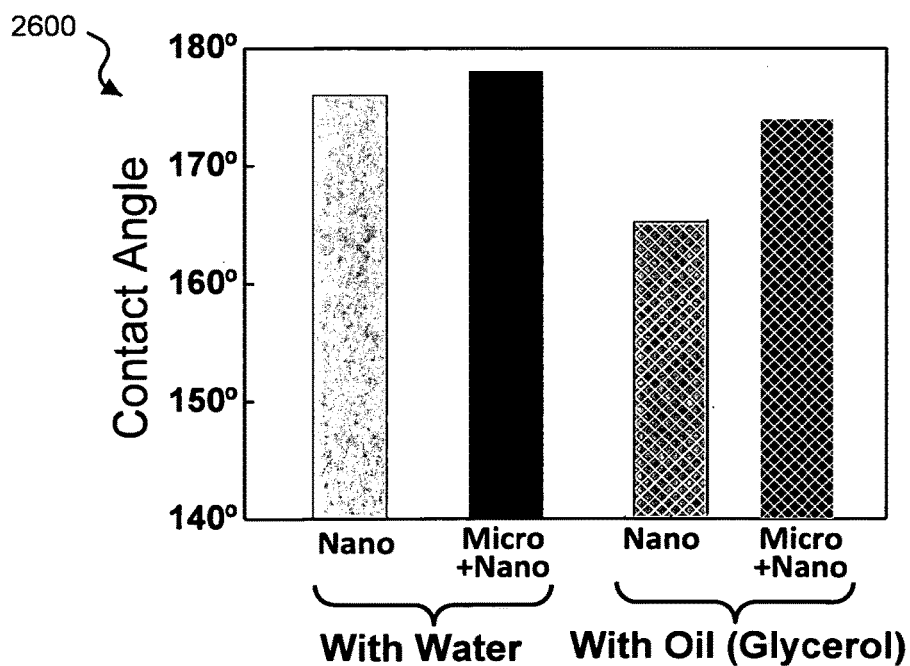
FIG. 26 shows an exemplary graph of contact angle data of flat and micro-rough surfaces modified with $TiO_2$ nanotube surface structures.

Exemplary data of flat surface (2410) and micro-roughness surface (2420) are shown in FIGS. 25 and 26. FIG. 25 shows exemplary cross-sectional images of a water droplet (e.g., image (2510)) and an oil (glycerol) droplet (e.g., image (2520)) on a Ti foil surface with hydrothermally grown $TiO_2$ nanotube structures (after fluorination). FIG. 25 also shows exemplary cross-sectional images of a water droplet (e.g., image (2530)) and an oil (glycerol) droplet (e.g., image (2540)) on a micro-textured and hydrothermally processed Ti foil surface (after fluorination). FIG. 26 shows an exemplary graph (2600) that exhibits the contact angle data results, which demonstrates the excellent superhydrophobic and/or superoleophobic properties of the surfaces featured in images (2510), (2520), (2530), and (2540). For example, the contact angle of the exemplary water droplet on the flat Ti surface with $TiO_2$ nanotube structures after fluorination in image (2510) was measured ~175°. The contact angle of the exemplary oil droplet on the flat Ti surface with $TiO_2$ nanotube structures after fluorination in image (2520) was measured ~165°. The contact angle of the exemplary water droplet on the micro-rough Ti surface with $TiO_2$ nanotube structures after fluorination in image (2530) was measured ~178°. The contact angle of the exemplary oil droplet on the micro-rough Ti surface with $TiO_2$ nanotube structures after fluorination in image (2540) was measured ~172°. It is noted that the surfaces can be coating with very thin (~8 nm range) fluorine-containing material, e.g., with a perfluorosilane coating. This exemplary coating can be applied by using an exemplary process that includes soaking for 8 min in 0.5% 1H,1H,2H,2H-perfluorooctyltrichloro silane in n-hexane, washing with hexane, and drying and treating in a vacuum oven at 100° C. for 1 hr.

Figure 27:
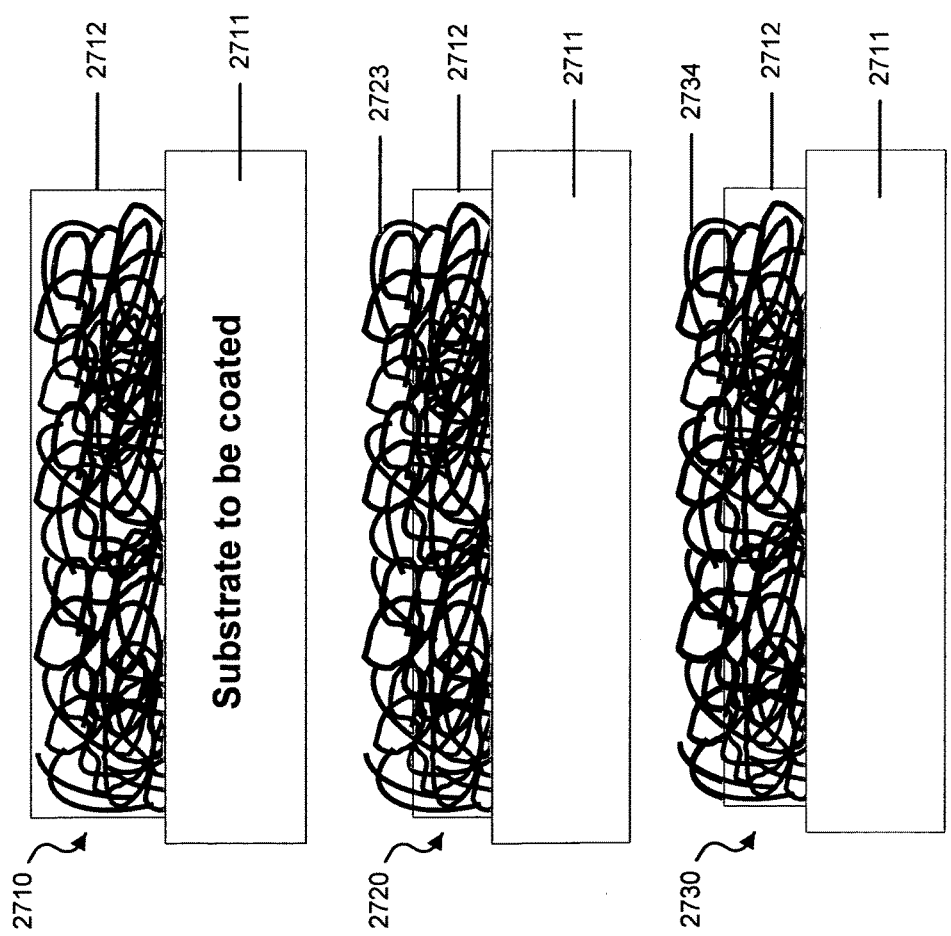
FIG. 27 shows an exemplary paste coating method to obtain superhydrophobic and/or superoleophobic coatings.

Another exemplary hydrothermal processing can include electrochemical anodization or paste processing a composite coating that includes $TiO_2$ nanotubes in a matrix polymer that is transparent or translucent can also be utilized. The exemplary paste coating method to obtain superhydrophobic and/or superoleophobic coatings (e.g., with 8 nm $TiO_2$ nanotubes) is illustrated in FIG. 27. FIG. 27 shows a process (2710) that can include depositing a layer of paste (2712) that contains nanostructures (e.g., the exemplary 8 nm $TiO_2$ nanotubes in a carrier polymer) onto a substrate (2711). Process (2710) can deposit the paste by at least one of matrix doctor blade coating, spin coating, spray coating, screen printing, etc. Process (2720) can include exposing the exemplary nanotubes (2723) embedded in the paste (2712) by partially removing the polymer from the top region. Process (2720) can include adding a thin fluorine-containing material (2733) on the surface, e.g., exemplary nanotubes (2723). For example, the exemplary thin and long titania nanotubes, after additional coating with fluorine-containing or related hydrophobic layer, can produce excellent superhydrophobic or oleophobic properties of water contact angle exceeding ~170°. Such extreme self-cleaning properties can be useful for a variety of technical anti-applications.

In another example, a two-phase surface hybrid structure can be produced, e.g., the small diameter nanotubes or nanowires can be only partially coated with the fluorine-containing hydrophobic layer near the upper regions while not coating the bottom valley regions with the fluorine-containing hydrophobic layer (e.g., Teflon). This can maintain superhydrophobic and/or superoleophobic properties. For example, the upper portion of the nanotubes or nanowires can be in contact with the liquid drops from the environment, while the valley region $TiO_2$ type materials can remain exposed to serve as a solar induced photocatalytic surface, e.g., to UV or visible light exposure. The photocatalytic functionality can include superoxide and other radical type active components capable of decomposing toxic chemicals or anti-bacterial effect for water treatment or environmental clean-up. The exemplary dual structure can have multiple an advantages and functionalities with superhydrophobic, superoleophobic, and/or photocatalytic surface properties.

In another embodiment, the disclosed technology can include ZnO and/or $SiO_2$ nanowire layered surface structures, e.g., for boat speed enhancement.

The disclosed technology can be implemented to produce a surface coating that is mechanically strong and durable while also possessing water-repellent surface properties. For example, the surface properties of the disclosed technology can enable faster movement of boats, yachts and ships in sea water or fresh water. Added speed and/or reduced energy consumption at the same speed can be advantageous properties for speed racing and saving energy to propel and transport sea vessels.

Figure 28:
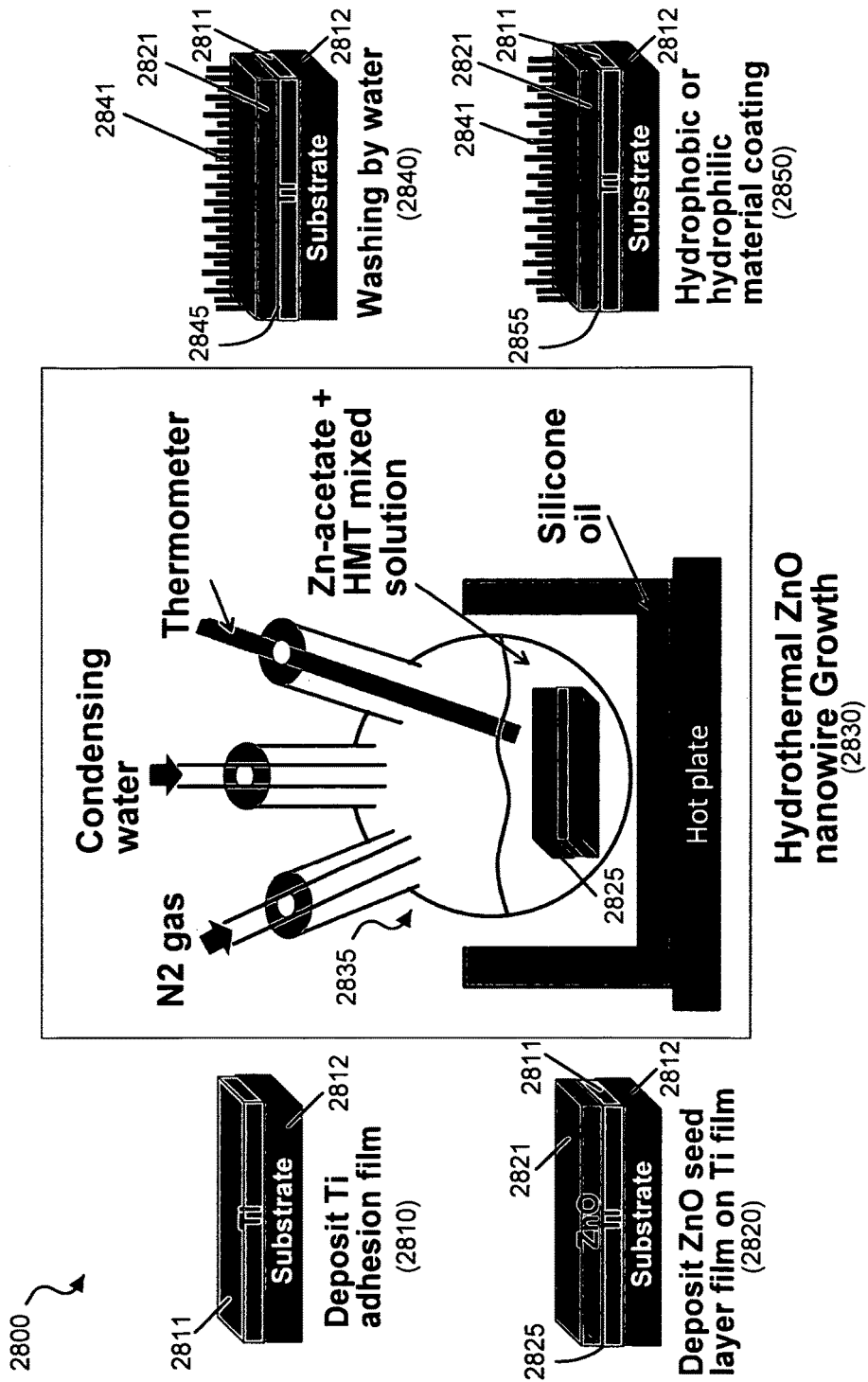
FIG. 28 shows an exemplary process to produce a nanowire layered surface.

The enhanced surface microstructure of the disclosed technology can incorporate a coating of Ti, Cr or other adhesion layer on the substrate, e.g., an ultra-high molecular weight polyethylene substrate. FIG. 28 shows a process (2800) to produce a nanowire layered surface, e.g., with adherent ZnO nanowires. For example, process (2800) can include process (2810) to deposit a Ti adhesion layer (2811) on a substrate (2812). Process (2810) can include depositing the exemplary Ti adhesion film (e.g., 20 nm layer) by sputtering. Process (2800) can include process (2820) to deposit a ZnO seed layer (2821) on the deposited Ti adhesion layer (2811). Process (2820) can include depositing the exemplary ZnO seed layer (e.g., 100 nm layer) by sputtering. Implementation of process (2820) can result in a substrate (2825). Process (2800) can include process (2830) for chemical reaction deposition of ZnO nanowires. For example, process (2830) can include chemical reaction for ZnO nanowire growth in a reaction growth chamber (2835) containing 55 mM Zinc acetate and 35 mM Hexamethylenetetramine (HMT), e.g., at 90° C. for 45 min in a silicone oil over a hot plate. Process (2830) can result in substrate (2845) that includes ZnO nanowires (2841). Process (2800) can include process (2840) for washing the substrate (2845) with DI water. Process (2800) can include process (2850) to coat the surface with fluorine-containing hydrophobic material (e.g., Teflon or trichlorosilane) by sputter coating or liquid precursor spin coating, which can result in a substrate (2855).

FIG. 29 shows an exemplary SEM image of the surface of substrate (2855), which has ZnO nanowires of ~100 nm diameter and ~2 μm height that are predominantly vertically aligned. The exemplary ZnO nanowires produced using process (2800) shown in FIG. 29 were coated with Teflon hydrophobic layer. The resultant material surface exhibited excellent non-wetting properties of 170° and higher with water droplets. For example, the exemplary coating can be produced on a difficult-to-adhere plastic substrate at a low temperature of ~100° C. or below. This can provide an ease of processing without damaging the underlying plastic material. Some exemplary applications of the material produced using process (2800) can include sports articles, devices, and systems such as racing yachts, and can also be useful for energy saving of boats and ships, commercial, military and sports racing related as the energy used for propelling and thrusting of boat in water can be reduced.

Figure 31:
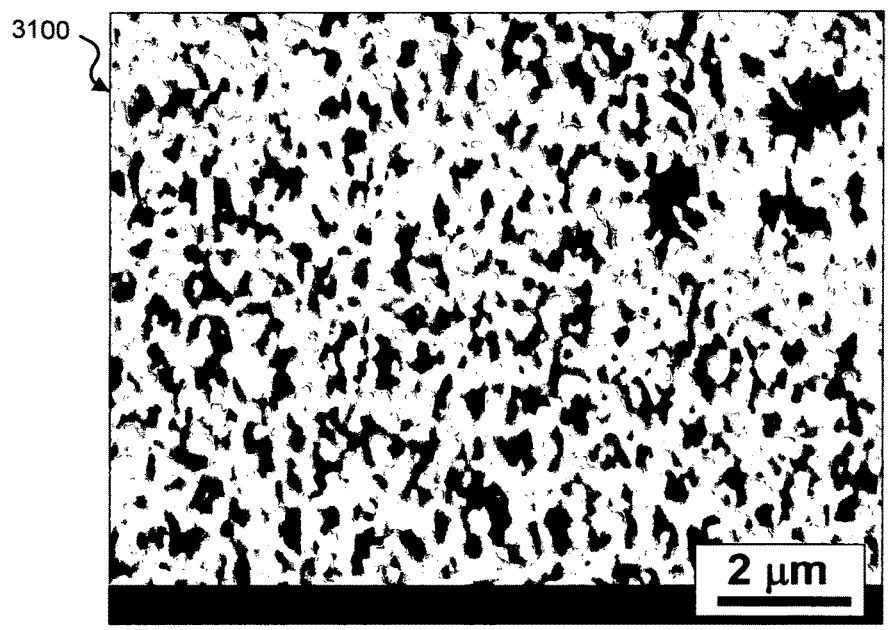
FIG. 31 shows an exemplary SEM image of adherent SiO$_2$ nanowire array.

In another example, $SiO_2$ nanowires can also be produced by similarly advantageous low-temperature processing, e.g., with the processing temperature not exceeding 110° C. FIG. 30 shows an exemplary process (3000) to produce a nanowire layered surface, e.g., with adherent $SiO_2$ nanopillar array from hydrogen silsesquioxane resist (HSQ) precursor layer on an ultra-high molecular weight polyethylene plastic substrate. Process (3000) can include process (3010) to deposit an HSQ layer (3011) on a substrate (3012) such as polyethylene plastic, e.g., by spin coating. For example, substrate (3012) can be spin-coated with a 1 μm (or thicker) layer of HSQ (Dow Corning No. Fox-16). Process (3010) can also include curing the exemplary HSQ layer (3011) to a solid layer form. For example, the sample can then be baked on a hotplate at 110° C. for 180 sec to vaporize the solvent in hydrogen silsesquioxane (HSQ). Process (3000) can include process (3020) to vertically reactive ion etch the $SiO_2$ layer (3021) by $CF_4$ type gas to make a vertically aligned $SiO_2$ nanopillar array. Process (3030) can include rendering the $SiO_2$ nanopillar array (3033) on the $SiO_2$ layer (3021) to form substrate (3035). Process (3000) can include process (3020) to coat substrate (3035) with a fluorine-containing, hydrophobic (or hydrophilic) material for enhanced superhydrophobic surface. For example, the exemplary fluorine-containing hydrophobic material (or hydrophilic material) can be applied onto the $SiO_2$ nanopillars through a vaporization process in vacuum or Teflon coating (sputtering or liquid spin-coating). FIG. 31 shows an SEM image (3100) of a resultant sample after implementing process (3000). The exemplary SEM image (3100) shows the microstructure of the $SiO_2$ nanowire array with the wire diameter of ~100-200 nm. The exemplary sample exhibited excellent superhydrophobicity with a contact angle with water droplet greater than 155°.

In another embodiment, the disclosed technology can include an omniphobic nanostructure that includes an impregnated hydrophobic liquid or hydrophilic liquid.

As previously described, exemplary nanostructured superhydrophobic and/or superoleophobic surfaces can benefit from a very thin coating (e.g., a few to tens of nanometers thick) such as a fluorine-containing surface coating (e.g., Teflon or fluoroalkylsilane (trimethoxylsilane) or related compound material). However, some applications may be susceptible to excessive mechanical rubbing, e.g., touch-sensitive display screens or devices such as computers, laptops, smart phones, tablets, e-readers and other devices and systems. Also, for example, solar cell panel glass layers can be subjected to conditions (e.g., rain, hail, or other type weathers and washing operations) that can cause mechanical shear and/or compressive stresses. Thus, hydrophobic coating layers (e.g., the exemplary layers added onto the nanostructure surface) can be prone to wear. This may result in the exemplary nanostructured superhydrophobic and/or superoleophobic properties becoming partially degraded over time. The disclosed technology can include techniques and articles that preserve the fluorine-containing liquid on a continuous basis for a long time to maintain the superhydrophobic and/or superoleophobic surfaces (and other exemplary hydrophilic liquid layers for superhydrophilic surface applications).

For example, the disclosed technology can include nanostructured surfaces and fabrication methods that incorporate a porous structure with impregnated and trapped, fluorine-containing or related liquid material that renders the surface nearby to continuously become and remain superhydrophobic, superoleophobic or superhydrophilic. The exemplary impregnated structures can continue to function as desired even after mechanical rubbing or erosion, e.g., since an impregnated reservoir can continue to supply the superhydrophobic, superoleophobic or superhydrophilic material through surface diffusion coverage. Thus, the disclosed impregnated structures can continue to have the designed self-cleaning or non-wetting characteristics.

For example, a structure can be optically transparent or opaquing, which can be based on the needs and the type of liquid impregnated. Exemplary transparent structures can be useful for anti-fingerprint coating on glass cover sheets of interactive touch-sensitive display screens on a variety of devices, articles, and systems. Exemplary non-transparent structures can be useful for long-lasting, self cleaning coating for solar glass or anti-corrosion coating, or self cleaning paints for infrastructures, e.g., bridges, buildings, or transportation vehicles such as ships, automobiles, tanks, airplanes, etc.

Figure 32:
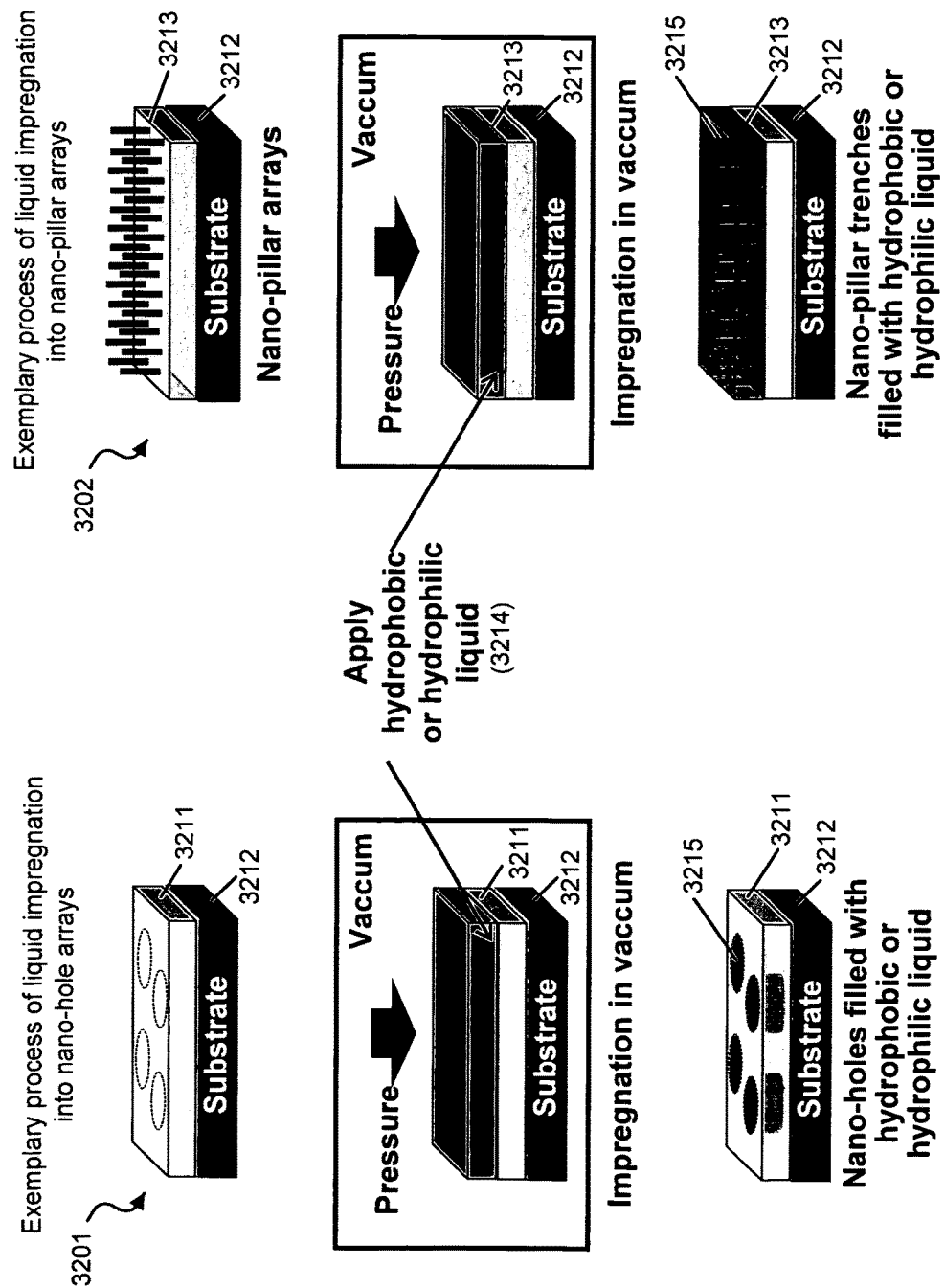
FIG. 32 shows an exemplary process to produce durable superhydrophobic and/or superoleophobic (or superhydrophilic) surfaces.

FIG. 32 shows an exemplary process to implement liquid impregnation of hydrophobic (or hydrophilic) liquid for superhydrophobic, superoleophobic (or superhydrophilic) surface structures. In one example, an exemplary process (3201) can include liquid impregnation into nano-sized pores or holes arranged in an array on a surface. Process (3201) can include preparing an article that includes a layer having an array of nanopores or nanoholes (3211), e.g., anodized $Al_2O_3$ or $TiO_2$, over a substrate (3212). Process (3201) can include applying a hydrophobic (or hydrophilic) liquid layer (3214) over the array of nanopores layer (3211) and impregnating the hydrophobic (or hydrophilic) liquid into the nanopores. Implementing process (3201) can result in the array of nanopores layer (3211) being filled with the hydrophobic (or hydrophilic) liquid (3215).

In another example, an exemplary process (3202) can include liquid impregnation into nanopillar or nanowire trenches on a surface. For example, the nanopillar or nanowire trenches can be vertically aligned $SiO_2$ nanopillars, ZnO nanowires, Si nanowires, carbon nanotubes, or loose or tangled nanowires and nanotubes of Si, $SiO_2$, ZnO, $TiO_2$, e.g., which can be made by electroless etching, lithography, nano-imprinting, reactive ion etch, hydrothermal etching, decomposition, precipitation, or chemical vapor deposition. Process (3202) can include preparing an article that includes a layer having an array of nanopillars or nanowires (3213), e.g., $SiO_2$ nanopillars, nanowires, loose/tangles $TiO_2$ nanowires and nanotubes, over a substrate (3212). Process (3202) can include applying a hydrophobic (or hydrophilic) liquid layer (3214) over the array of nanopillarskianowires layer (3213) and impregnating the hydrophobic (or hydrophilic) liquid in between the trenches of the nanopillars/nanowires. Implementing process (3202) can result in the array of nanopillars/nanowires layer (3213) being filled with the hydrophobic (or hydrophilic) liquid (3215).

For an exemplary experimental demonstration of the impregnation technique, nanohole or nanopillar arrays were made by anodized $TiO_2$ nanotubes (e.g., at 20 volts, 0.5% HF acid electrolyte) or $Al_2O_3$ anodization. A hydrophobic liquid material, e.g., a liquid PTFE coating (2% AF1601 from DuPont), was put into the nanoholes or nanotrenches using vacuum suction process. The substrates were then baked on an oven or hotplate at 110° C. for 30 min, and water droplet contact angle measurements were performed before and after mechanical rubbing of the surface with sandpaper.

Figure 33:
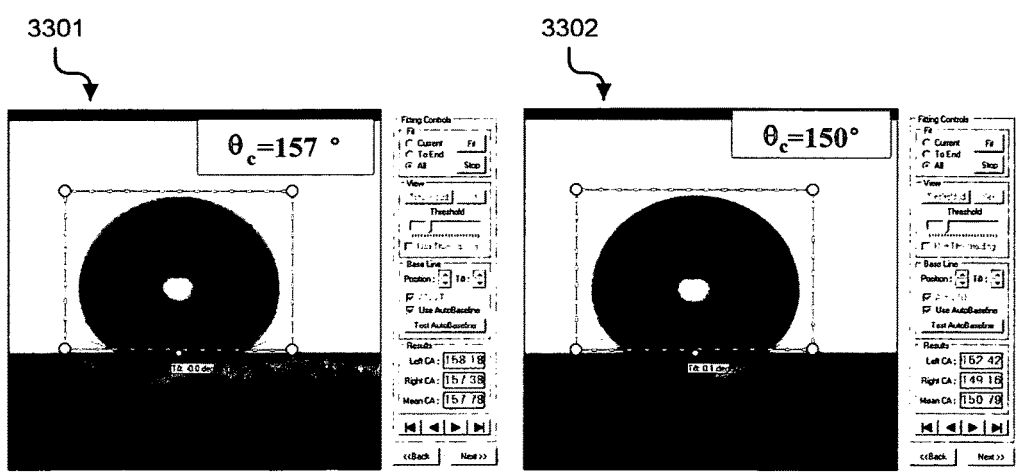
FIG. 33 shows exemplary water droplet contact angle measurements performed on surfaces with TiO$_2$ nanotubes prepared by anodization.

FIG. 33 shows exemplary water droplet contact angle measurements performed on surfaces with $TiO_2$ nanotubes prepared by anodization. For example, exhibit (3301) shows the contact angle equal to 157° of the exemplary surface after impregnating hydrophobic liquid. Exhibit (3302) shows the contact angle equal to 150° of the exemplary surface after the surface was rubbed by sand paper. Thus, the superhydrophobic nature of the $TiO_2$ nanotube structure can be maintained even after sandpaper rubbing and grinding, demonstrating the successful application of the impregnation technology.

In another embodiment, the disclosed technology can include nano-sized and micro-sized capsules for reservoir storage and long-term slow release of hydrophobic (or hydrophilic) liquid. For example, the exemplary microcapsules and nanocapsules can include trapped fluorine-containing or related liquid so that the liquid can be released at a controlled, intentionally slower speed for long lasting effect. For example, the described nanopillar or nanopore structures can be utilized as the basis to trap and secure these added nanocapsules or microcapsules containing the desired liquid.

Figure 34:
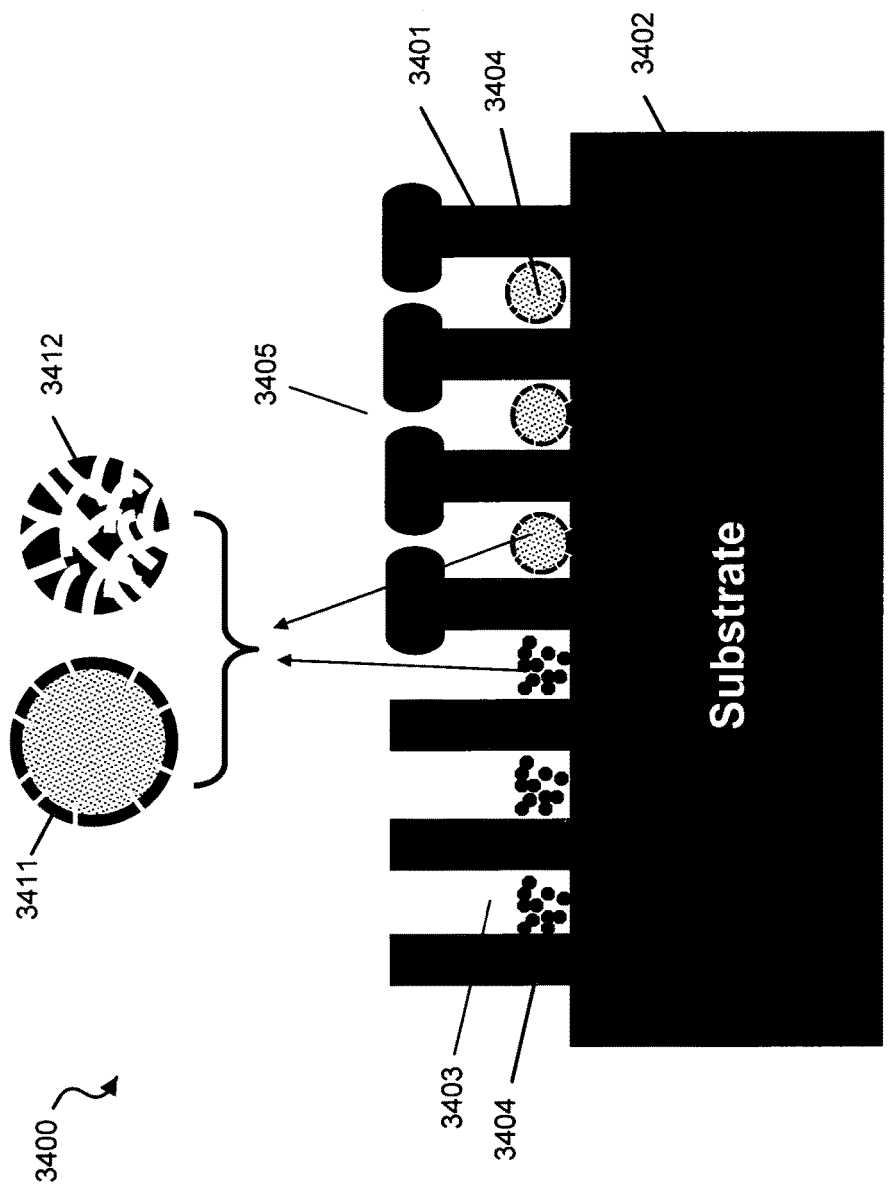
FIG. 34 shows an exemplary superhydrophobic, superoleophobic or superhydrophilic structure that includes micro- and/or nano-sized capsules.

FIG. 34 shows an exemplary structure (3400) for micro- and nano-capsuled superhydrophobic, superoleophobic or superhydrophilic structures. Structure (3400) can be fabricated by any of the aforementioned processes, e.g., to produce an array of nanopillars (3401) over a substrate (3402). The array of nanopillars (3401) can be, for example, plasma RIE etched silica nanowires, electroless etched silicon nanowires oxidized to become silica nanowires, lithographically patterned silica, Si nanowires, and other aforementioned nanostructures. Additionally, structure (3400) can include aligned nanopores (3403), e.g., vertically aligned nanopores, which can be made by anodized aluminum oxide, titanium oxide nanotubes, plasma etched transparent silica nanopores, Structure (3400) can have random nanopores, nanowires and nanotubes that can be used as the bases into which micro-sized and/or nano-sized capsules (3404) can be embedded and secured. For example, micro-/nano-sized capsules (3404) can include hollow type capsules, e.g., hollow capsule (3411), and random pores capsules, e.g., random pores capsule (3412). Structure (3400) can have a bottlenecked entrance (3405) to secure capsules (3411) and (3412) between nanopillars (3401). The capsules can be pre-impregnated with fluorine-containing hydrophobic liquid, or hydrophilic liquid depending on specific requirements for the surface. The capsules themselves have distributed nanopores with their surface pores either remain open or temporarily blocked with slowly degradable or slowly dissolvable polymer coating until a desired time. For some applications, the capsules can be desirably made of silica or other transparent materials for devices and systems with touch-sensitive displays and solar cell-related devices, e.g., solar glass. For other general applications, less transparent materials such as titania, zirconia, alumina, graphite or other ceramic, metal or polymer hollow spheres or highly porous particles can be utilized.

In another embodiment, the disclosed technology can include periodic mushroom-tip-shaped silicon or silicon oxide nanowires.

Figure 35:
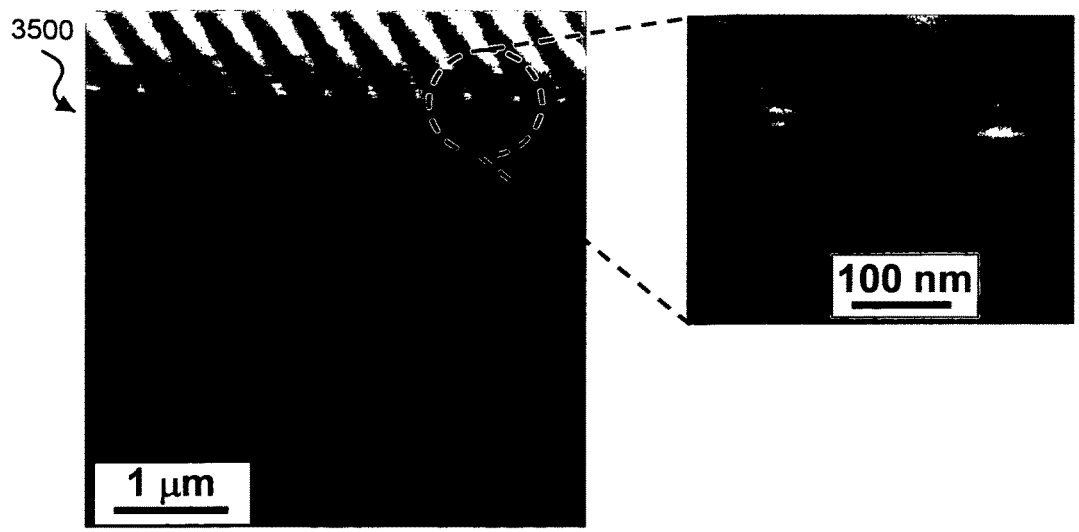
FIG. 35 shows an exemplary SEM image of periodic mushroom-tip shaped nanowires produced by nano-imprinting.

For example, superhydrophobic, superoleophobic or superhydrophilic surface structures can also be produced by making a dense array of tall Si or SiO$_2$ nanowires prepared by nano-imprinting. FIG. 35 shows exemplary an exemplary image (3500) of periodic mushroom-tip shaped nanowires (e.g., Si or silicon oxide) produced by nano-imprinting. For example, a SU-8 or polymethyl methacrylate (PMMA) resist layer can be nano-imprinted using a mould (stamp) into, e.g., having a 200 nm diameter and 200 nm spaced nano-pattern. Subsequently, a Ni mask deposition can be implemented, e.g., by sputtering and lift off process. An Si or SiO$_2$ layer can then be vertically etched to produce an array of tall nanowires (e.g., at least 0.5 μm tall, or at least 2 μm tall as seen in image (3500)). In addition to the vertical etching, the disclosed technology can include etching by using a mixed RIE gas with the SF$_6$ (Si etching etching gas) and C$_4$F$_8$ (sidewall passivation gas), e.g., with the SF$_6$ content at least 30% of the mixed gas volume so that the sidewall can be intentionally etched, which can reduce the diameter while the tip region still protected by metallic etch mask (e.g., Ni in the exemplary case, but other metals such as Co, Cr, Ti, Mo, V, Au, Pt, Pd may also be utilized). The resultant mushroom patterned, structure can exhibit superomniphobic properties in the as-fabricated condition, e.g., with water droplet contact angle measurements of greater than 160° and oil (oleic acid) droplet contact angle measurements of 140°, even with no additional hydrophobic coating.

In another embodiment, the disclosed technology can include superomniphobic surface having structurally mixed superhydrophobic and superhydrophilic regions.

Figure 36:
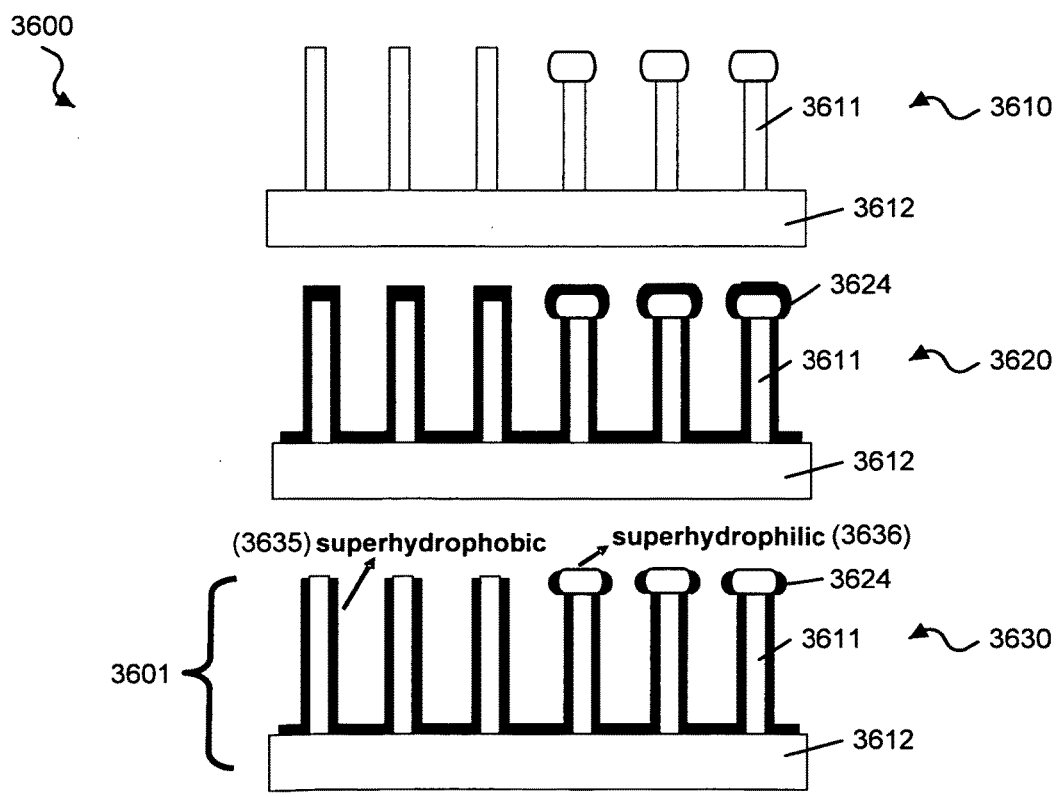
FIG. 36 shows an exemplary process to produce a superomniphobic surface with mixed superhydrophobic and superhydrophilic regions.

FIG. 36 shows an exemplary schematic illustration of a process (3600) to produce a composite material (3601) having structurally mixed superhydrophobic and superhydrophilic regions. For example, composite material (3601) can exhibit superomniphobic characteristics. Composite material (3601) can include nanowires or nanotubes of equi-diameter and/or a re-entrant mushroom shape, e.g., which can be produced by dip coating of tips or lithographical sidewall etching processes, as described earlier. The vertically aligned nanorods, nanopillars, nanotubes of composite material (3601) can be made from metallic, ceramic or polymer materials, such as silicon, silica, alumina, titania, PEEK (polyether ether ketone), ultra-high-strength-polyethylene, e.g., having a desired diameter in a range between 500 nm and 5 μm, and be vertically aligned at a desired angle of 70° or greater.

Process (3600) can include a process (3610) to fabricate vertically aligned nanostructures (3611) (e.g., nanorods, nanopillars, and nanotubes) on a substrate (3612). Nanostructures (3611) can be fabricated such that they exhibit equivalent diameter and/or a re-entrant mushroom shape tip. Process can include fabricating nanostructures (3611) by self assembly, template-assisted method, by lithography on substrate (3612), or by depositing a buffer layer on another substrate made of similar materials as the pillars. Process (3600) can include process (3620) to coat the surface of nanostructures (3611) by a hydrophobic layer (3624), e.g., a fluorine containing material such as PTFE or Teflon-like layer, or trichlorosilane by vapor deposition, liquid precursor filling and drying or baking. Process (3600) can include process (3630) to selectively remove the top of the superhydrophobic coating (3624), e.g., by ion or plasma etch, rapid chemical etch, or light mechanical polishing. Implementation of process (3600) can create a mixture of superhydrophobic trench regions (3635) and superhydrophilic pillar top regions (3636) of the composite material (3601), which becomes superomniphobic. For example, selection of mechanically harder materials such as ceramic or metal nanostructures can provide a structure having wear-resistant properties and superomniphobic surface.

Figure 37:
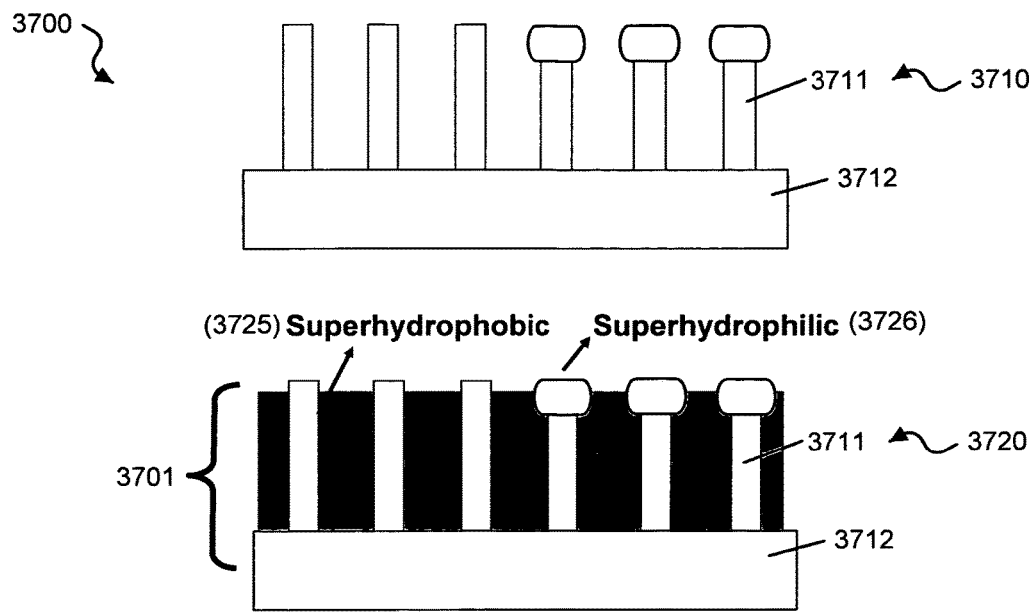
FIG. 37 shows an exemplary process to impregnate superhydrophobic liquids or solids into a material with structurally mixed superhydrophobic and superhydrophilic regions.

Alternatively or in addition to process (3600), a hydrophobic material can be impregnated into the trench regions (e.g., region (3635) of composite material (3601)) of the vertically aligned nanostructures without drying into a solid state. FIG. 37 shows an exemplary process (3700) to impregnate superhydrophobic liquids or solids into a material with structurally mixed superhydrophobic and superhydrophilic regions to impart superomniphobic characteristics in a material (3701). Process (3700) can include a process (3710) to fabricate vertically aligned nanostructures (3711) (e.g., nanorods, nanopillars, and nanotubes) on a substrate (3712). Nanostructures (3711) can be fabricated such that they exhibit equivalent diameter and/or a re-entrant mushroom shape tip. Process can include fabricating nanostructures (3711) by self assembly, template-assisted method, by lithography on a substrate (3712), or by depositing a buffer layer on another substrate made of similar materials as the pillars. Process (3700) can include process (3720) to impregnate a superhydrophobic liquid or solid (3723) into the gaps (e.g., nanotrenches) between the vertical nanostructures (3711). For example, superhydrophobic liquid or solid (3723) can include fluorine containing fillers, e.g., PTFE-like or Teflon-like material, trichlorosilane or hydrophobic polymer, e.g., ultra-high strength polyethylene. Selective removal of pillar top regions (e.g., implementation of process (3630)) can be optionally applied, e.g., by plasma etch or mechanical etch. For example, the hydrophobic liquid (or solid) can continue to supply the superhydrophobic portion in the composite structure of material (3701). For example, when the hydrophobic liquid eventually dries out, the trench area can still remain hydrophobic, thus maintaining the mixed superhydrophobic and superhydrophilic structure state.

Figure 38:
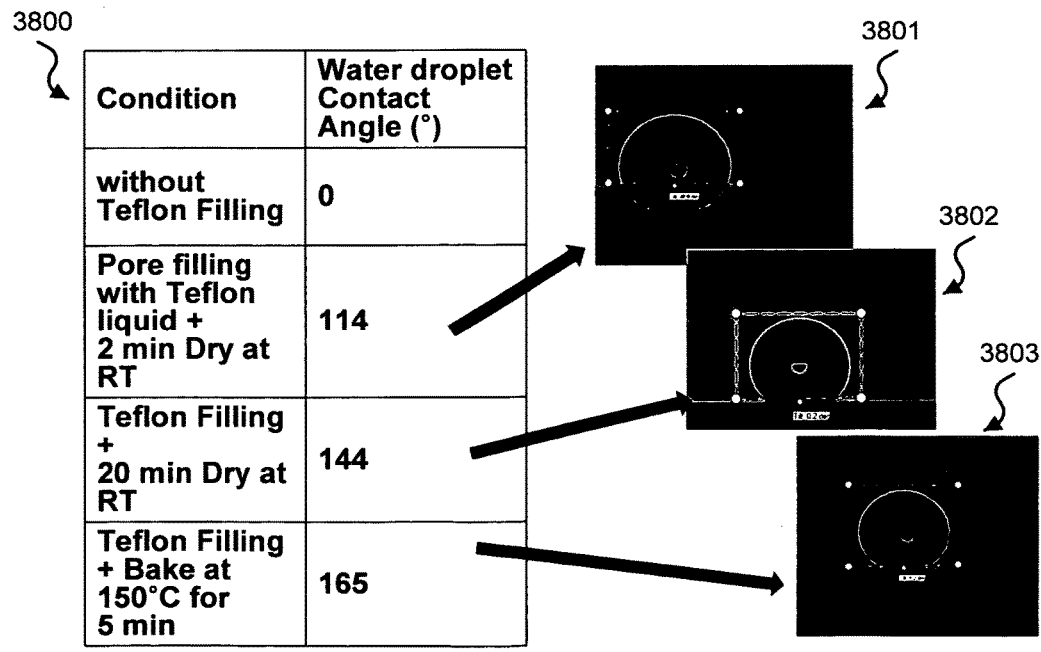
FIG. 38 shows an exemplary table and images of water contact angle measurements on surfaces produced by various fabrication conditions.

As an example, the exemplary composite superhydrophobic and superhydrophilic structure (e.g., material (3701)) was fabricated and characterized using contact angle measurements. For example, vertically aligned TiO$_2$ nanotube arrays were fabricated anodizing at 20 V, in 0.5% HF solution to produce ~100 nm diameter and 0.5-2 μm tall nanotubes. The trenches between the nanotubes can be filled with liquid Teflon, and the contact angle was evaluated as a function of liquid drying process. FIG. 38 shows an exemplary table (3800) of contact angle data of various fabrication conditions. For example, conditions included: a condition without Teflon filling; a pore filling condition with Teflon liquid and 2 min drying at room temperature (RT) (water droplet shown in image (3801)); a pore filling condition with Teflon liquid and 20 min drying at RT (water droplet shown in image (3802)); and a pore filling condition with Teflon liquid and 5 min baking at 150° (water droplet shown in image (3803)). For the exemplary condition without Teflon filling, the contact angle was measured at 0°. For the exemplary pore filling condition with Teflon liquid and 2 min drying at RT, the contact angle was measured at 114°, exhibiting hydrophobic properties. For the exemplary pore filling condition with Teflon liquid and 20 min drying at RT, the contact angle was measured at 144°, exhibiting superhydrophobic properties. For the exemplary pore filling condition with Teflon liquid and 5 min baking at 150°, the contact angle was measured at 165°, exhibiting even greater superhydrophobic properties. The exemplary TiO$_2$ nanotubes without pore filling exhibit superhydrophilic properties, with a water droplet contact angle of typically less than a few degrees. As the liquid Teflon was dried further, the superhydrophobic property improved and the contact angle is increased.

Figure 39:
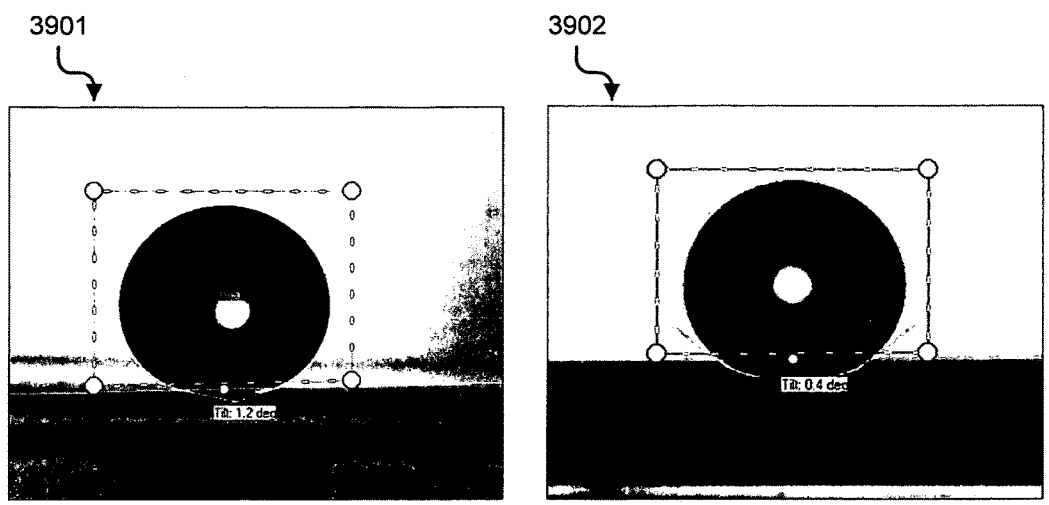
FIG. 39 shows exemplary images of water and oil droplets on a surface exhibiting superomniphobic properties.

As another example, FIG. 39 shows exemplary images of a surface exhibiting super-omniphobic properties, e.g., the surface having structurally mixed superhydrophobic and superhydrophilic regions in arrays of vertical nanostructures made of anodized, 100 nm diameter vertical $TiO_2$ nanotubes filled with Teflon liquid. Image (3901) shows a water droplet with a superhydrophobic contact angle of 165° on the surface, and image (3902) shows an oleic acid oil droplet with a superoleophobic contact angle of 141° on the surface.

Figure 40:
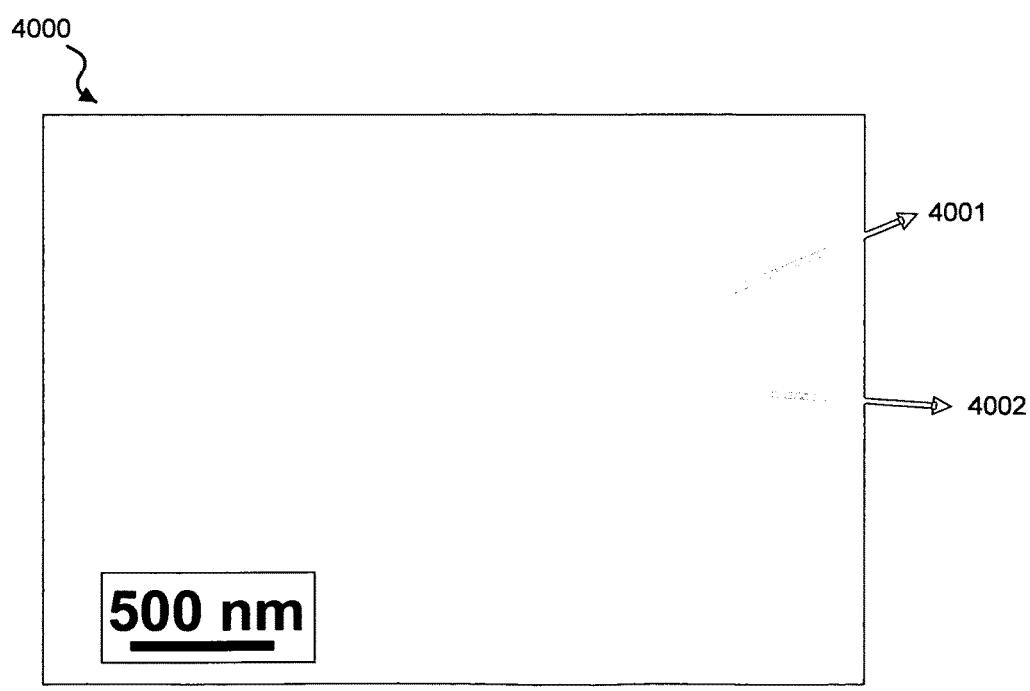
FIG. 40 shows an exemplary image of a surface with structurally mixed superhydrophobic and superhydrophilic regions.

FIG. 40 shows an exemplary image (4000) of a surface with structurally mixed superhydrophobic and superhydrophilic regions formed by an array of vertical $SiO_2$ nanopillar structures (4001) with gap spacing (trench regions) (4002) coated with hydrophobic Teflon. The exemplary surface exhibits superhydrophobicity in trench region (4002), while the nanopillar structures (4001) top regions are superhydrophilic. In this example, the periodic array of $SiO_2$ nanowires (4001) are configured with 200 nm diameter and 2 μm height, made by 1000° C. oxidation of Si nanowires prepared by nano-imprinting patterning using Ni mask islands and RIE etch (previously described). The trench region (4002) between the silica nanowires are filled with liquid Teflon and baked to produce the dual hydrophilic+hydrophobic composite structure. FIG. 41 shows an exemplary table (4100) of contact angle data of water droplet and oleic acid droplet measurements for the exemplary dual hydrophilic+hydrophobic composite structure surface. The measurement showed a water droplet contact angle of 161° (superhydrophobic) and an oil (oleic acid) droplet contact angle of 132° (superoleophobic), thus demonstrating that the structure is superomniphobic. FIG. 41 also shows images featuring the water droplet shown in image (4101) and the oil droplet shown in image (4102) over the superomniphobic structure.

FIG. 42 shows an exemplary plot (4200) of optical transparency across a range of wavelengths of the superomniphobic structure (4202) and a glass substrate (4201), e.g., soda lime glass. In this example, the superomniphobic structure is a composite hydrophobic and hydrophilic material, with structurally mixed superhydrophobic and superhydrophilic regions formed by an array of vertical $SiO_2$ nanopillar structures having the trench region coated with Teflon. The superomniphobic material (4202) exhibited excellent transparency with only ~5-10% average loss compared with the glass substrate (4201). FIG. 43 shows an exemplary photograph of the excellent optical transparency of the superomniphobic composite material (4302) compared with the glass substrate (4301).

In another embodiment, the disclosed technology can include techniques, structures, materials, devices, and systems for implementing transparent and anti-fingerprint coatings on surfaces. For example, the disclosed transparent and anti-fingerprint coated surfaces can include surface nanoscale and/or microscale structures (e.g., nano-/micropillars) on a substrate surface, providing having superhydrophobic or superomniphobic properties. The exemplary transparent and anti-fingerprint coatings can be implemented in touch-screen display devices. Additionally, the disclosed technology can be configured to be optically transparent, mechanically durable and wear-resistant. For example, an exemplary coating can be applied either permanently on the information viewing screen of the touch-screen display devices, or can be added on as a replaceable layer, e.g., as in the form of sticky glass or polymer layer.

Additionally, the disclosed technology can the substrate itself (e.g., a thin and optically transparent glass sheet or a polymer sheet) can be surface patterned in microscale or nanoscale to impart anti-fingerprint characteristics.

Exemplary fabrication methods are described herein. For example, a fabrication method can use a silicon-containing buffer layer (e.g., Si, silicon oxide, silicon nitride, or in general, any transparent oxide, nitride or fluoride layer) for enhanced formation of well-defined, well-adhered, surface island arrays of mask material and wear-resistant structures. Exemplary Si containing buffer layers, e.g., a $SiO_2$ layer deposited by PECVD, can provide a clean, low-metal-content glass layer with enhanced transparency, as well as provide a surface that can be easily patternable to nanopillar or micropillar structures to impart superhydrophobic or omniphobic surfaces. For example, prevention or minimization of fingerprints can be important for consistent clear view of the written text or video information under the screen on display screen devices. For example, wear resistance and anti-friction characteristics can be important for durable use of such touch sensitive display screens and thus incorporated into the disclosed technology. An exemplary Si containing buffer layer, such as a $SiO_2$ layer, can also allow easy formation of a metal island mask by enabling a deposited metal layer to be balled up on subsequent high temperature annealing to produce a metal (or polymer) island mask array for reactive ion etch patterning of the $SiO_2$ layer into vertically aligned pillar structures.

For example, exemplary omniphobic surfaces can be made by wet or dry etching using polymer or metal mask, e.g., nano- or micro-patterned on optically transparent silicon dioxide intermediate layer (buffer layer) deposited on a transparent substrate, for example, by PECVD or other methods. For example, by wet or dry etching conditions, the size and shape of nano or microscale protrusions can be adjusted, e.g., as a mushroom shape. Also, other transparent substrate material or buffer layer materials can be utilized for making omniphobic surfaces, e.g., a commercially available soda lime glass, high-purity glass or other oxide, nitride or fluoride substrates, etc. Also, a transparent polymer substrate or polymer buffer layer such as polycarbonate plate may also be utilized.

Figure 44:
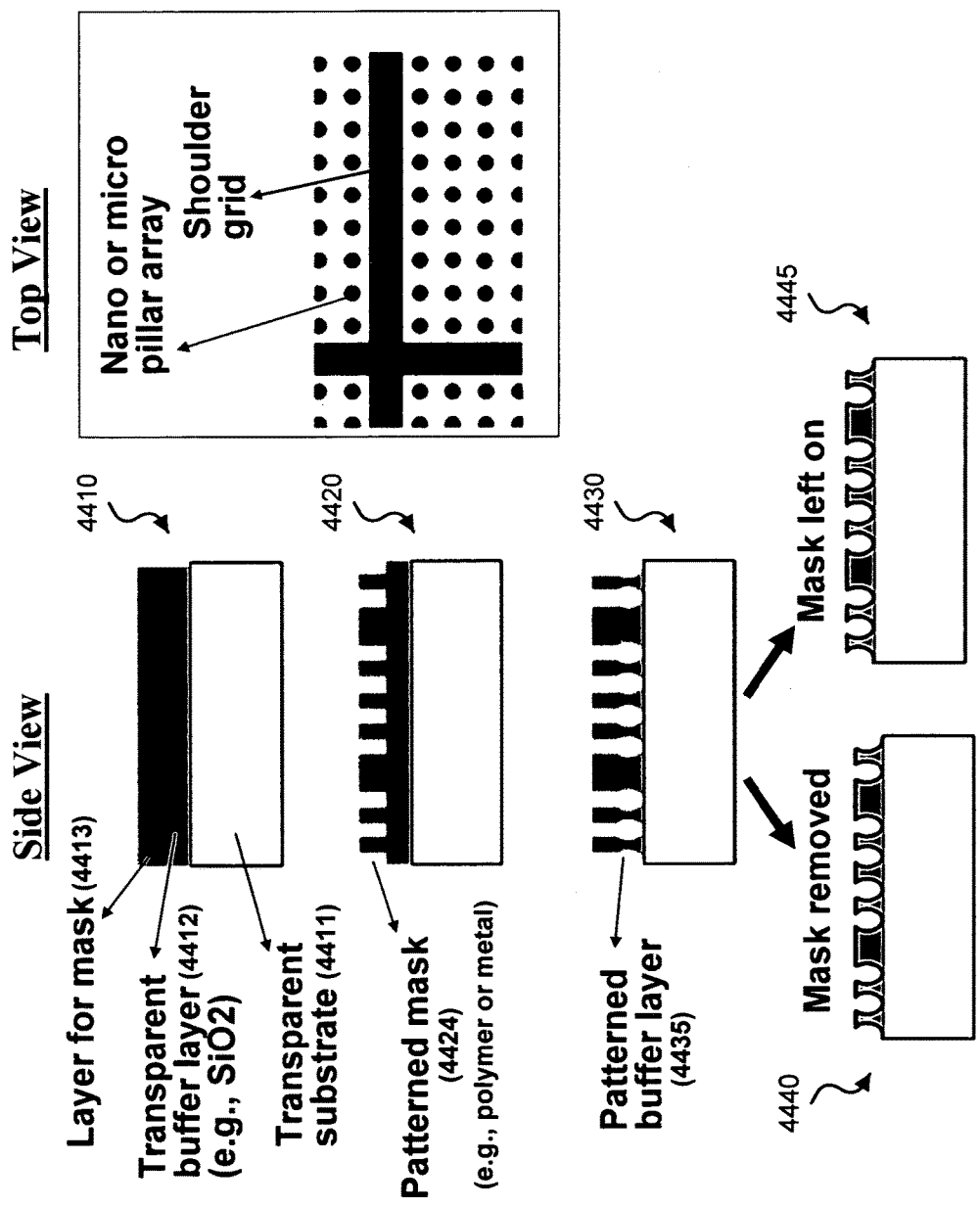
FIG. 44 shows an exemplary schematic diagram for providing an omniphobic surface on a substrate.

FIG. 44 shows an exemplary schematic diagram of a patterning process to produce omniphobic surfaces, e.g., preparation of a superhydrophobic or omniphobic surface on a transparent substrate. As shown in FIG. 44, process (4410) can include making polymer patterns on transparent substrate (4411). To do such, process (4410) can include depositing an intermediate (transparent) buffer layer (4412), e.g., silicon oxide, by PECVD deposition or other methods such as sputter deposition, evaporation, chemical precursor deposition, or sol-gel techniques. The thickness of buffer layer (4412) can be configured in the range of 10 nm to 10 μm, and in this example, preferably in the range of 100 nm to 1 μm. Process (4410) can include depositing a mask layer (4413), which can be a polymer mask layer such as a polymethyl methacrylate (PMMA) resist layer, on the buffer layer (4412), e.g., by spin-coating on the silicon dioxide intermediate layer (4412).

As shown in FIG. 44, process (4420) can include patterning the polymer material used in mask layer (4413) by photolithography (e.g., by UV light), by electron beam lithography, or by nanoimprint lithography (NIL). For example, the thickness of the polymer resist layer can be in the range of 10 nm to 20 μm, and in this example, preferably 100 nm to 2 μm. For example, the dimension of the exemplary polymer mask (4424) on the exemplary silicon dioxide intermediate layer (4412) can depend on the size of the photo-mask patterns for photolithography or e-beam lithography, and on the pattern dimension of the master mould (stamp) for an exemplary NIL process in process (4420). For example, the diameter of patterns on pattern mask (4424) can be in a range less than 10 µm, and in this example, preferably less than 1 µm.

As shown in FIG. 44, process (4430) can include fabricating micro-scale or nano-scale pillars to form a patterned buffer layer (4435) with the wet or dry etching, e.g., using polymer or metal pattern mask (4424) as an etching mask. For example, the diameter of the pillars in patterned buffer layer (4435) can depend on the size of polymer or metal patterns of pattern mask (4424). For example, the depth of the pillars in patterned buffer layer (4435) can be controlled by the thickness of the silicon dioxide layer and the wet or dry etching conditions, e.g., to be between 10 nm to 5 µm. For example, the shape of the pillars in patterned buffer layer (4435) can be adjusted, e.g. as mushroom shape, by changing the wet or dry etching conditions of a substrate. For example, in case of the wet etching, hydrofluoric acid (HF) or buffered oxide etchant (BOE) addition of $NH_4F$ to HF solution can be used as etching solutions, and the shape and length of the pillars in patterned buffer layer (4435) can be adjusted with the time of wet etching and the concentration of chemical solutions. Also, for example, a dry etching method can be used to make mushroom shape. The shape and length of the pillars in patterned buffer layer (4435) can be adjusted with the gas (e.g., $SF_6$ and $Cl_2$), time, power, and pressure of reactive ion etching (RIE). In some cases, the patterned mask (4424) can be removed as in process (4440). In other cases, the patterned mask (4424) can be left on as in process (4445).

The exemplary patterned $SiO_2$ pillars can exhibit hydrophilic properties rather than the hydrophobic properties without the coating. An additional deposition of hydrophobic coating on the patterned vertical nano or micro pillar arrays can be implemented impart the superhydrophobic or omniphobic properties on the exemplary silicon dioxide pillars. An example hydrophobic coating material includes a layer of trichloro(1H, 1H, 2H, 2H-perfluorooctyl) silane, or a layer of polytetrafluoroethylene (PTFE). The hydrophobic coating can range between 1-500 nm thick, or in some cases 10-100 nm thick, and in some examples, more preferably 30-100 nm thick. The PTFE hydrophobic coating can be a thin layer of $C_4F_8$ plasma polymer. The deposition of an exemplary PTFE thin layer by plasma deposition can be a simple and effective method, which is applicable to any substrates, e.g., transparent substrate (4411). Other coating methods can be used to make the substrate hydrophobic. In some examples, an additional coating may not be necessary if the substrate used is intrinsically hydrophobic. The exemplary resultant surface by implementation of these processes can be an omniphobic surface with micro-scale or nano-scale pillars.

An example of implementing process (4410), (4420), (4430), and (4440) is described. In this example, a 2 µm thick PMMA polymer layer can be spin-coated on soda lime silicate glass having a thin the silicon dioxide intermediate layer, e.g., 200 nm to 10 µm. The polymer patterns can be made by NIL process. Using the polymer pattern as an etch mask, soda lime silicate glass surface with the silicon dioxide nanopillars can be fabricated using wet etching. BOE can be used as an etching solution for $SiO_2$, and the shape and length of pillars can be adjusted with the time of wet etching and the concentration of chemical solutions. The exemplary soda lime silicate glass substrate may also need hydrophobic coating for making omniphobic surfaces, e.g., because soda lime silicate glass with the silicon dioxide nanoscale pillars is intrinsically hydrophilic. After removing polymer patterns on the surface (e.g., by acetone), the surface with microscale pillars may then be coated with a hydrophobic layer by a thin layer of $C_4F_8$ plasma polymer. The resultant material can be an omniphobic surface with water and oil contact angles greater than 150°. If an optically transparent substrate, e.g., window glass is used, the final omniphobic material (with or without polymer patterns) can be optically transparent with micro-/nano-scale pillars on the surface.

In another example of implementing processes (4410), (4420), (4430), and (4440) an exemplary polymer layer (e.g., 2 µm thickness) can be spin-coated on soda lime silicate glass substrate with the silicon dioxide intermediate layer. The exemplary metal patterns can be made by photolithography process. Using the metal patterns as an etching mask, soda lime silicate glass surface with the silicon dioxide nanoscale pillars can be fabricated using dry etching. Fluorine-based gas such as sulfur hexafluoride gas ($SF_6$) and chlorine ($Cl_2$) can be used as etching gases, and the shape and length of pillars can be adjusted with the time, power, and gas pressure of RIE. The exemplary soda lime silicate glass substrate may also need hydrophobic coating for making omniphobic surfaces, e.g., because soda lime silicate glass with the silicon dioxide nanoscale pillars is intrinsically hydrophilic. After removing polymer patterns on the surface (e.g., by acetone), the surface with microscale pillars can then be coated with a hydrophobic monolayer by a plasma system with thin layer of $C_4F_8$ plasma polymer. The resultant material can be an omniphobic surface with water and oil contact angles greater than 150°.

The resultant material can exhibit superomniphobic characteristics that include wear resistance, and anti-fingerprint adherence on the surface. For example, the superomniphobic characteristics can be further improved by introducing an exemplary protective grid shoulder array to guard against compressive or shear stresses. The disclosed technology can incorporate the exemplary protective grid shoulders on superhydrophobic surfaces (e.g., using an array of vertically aligned nanostructures like nanorods, nanowires, nanopillars, and nanocones) and superomniphobic surfaces (e.g., using an array of vertically aligned nanostructures configured with mushroom-shaped tips) to be more wear-resistant and prevent fingerprint adsorption. For example, FIG. 45 shows exemplary schematic illustrations of superhydrophobic materials (4510) and (4520) and superomniphobic material (4530) that include a substrate (4503) with patterned nanostructure arrays (4501) and protective spacer grid array (4502) to guard against compressive or shear stresses and make the materials more wear-resistant.

Figure 46A:
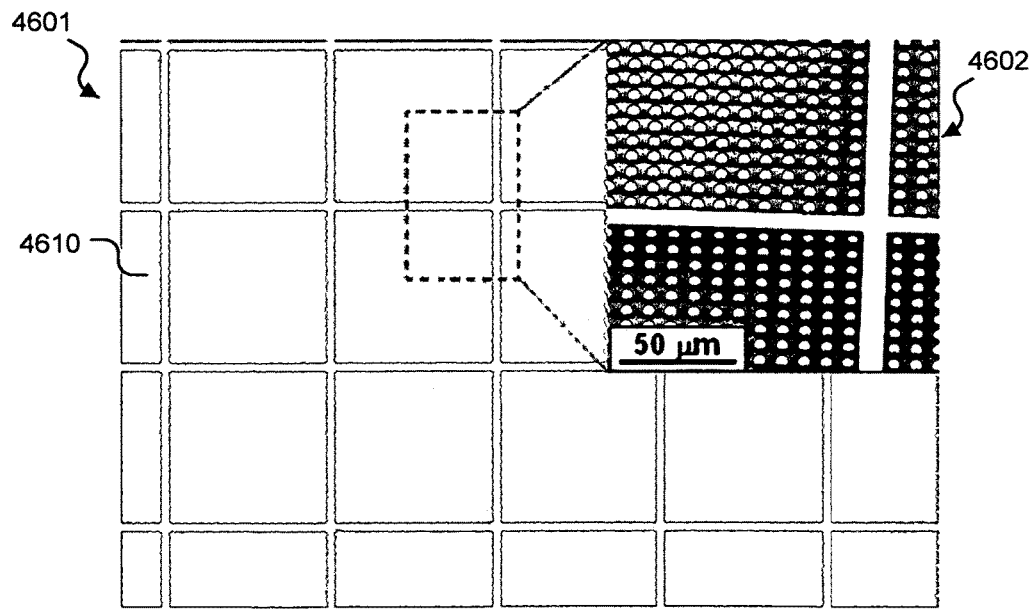
FIG. 46A shows an optical micrograph image of an exemplary material with an anti-fingerprint coating having superhydrophobic or omniphobic surface characteristics.

FIG. 46A shows an optical micrograph image (4601) of an exemplary material (4610) with an anti-fingerprint coating having superhydrophobic or omniphobic surface characteristics, as well as improved wear-resistance. In this example, the structure of patterned $SiO_2$ buffer layer was made by photolithography patterning of 4 µm thick PECVD deposited $SiO_2$ and etching. Image (4601) also shows the shoulder grid structure having a ~10 µm width and crisscross pattern every ~200 µm. Each grid square includes 20×20 pillar arrays. FIG. 46A also includes a high magnification SEM image (4602) of the patterned array of vertical pillars of $SiO_2$ buffer layer, e.g., with pillar dimension of ~5 µm diameter and ~5 µm spaced apart. The height of the exemplary micropillars is ~10 µm.

FIG. 46B shows an SEM image (4650) of an exemplary material with an omniphobic coating made of patterned buffer layer of $SiO_2$ having a mushroom-shaped tip configuration. For example, this can be achieved by a slight modification of the etch process to produce the exemplary mushroom geometry. The mushroom geometry can be advantageous for obtaining further improved omniphobic properties. For example, when a wet etching is applied to a polymer or metal mask covered micro or nano pillars (e.g., as shown in FIG. 44), the top of the pillars can be protected by photoresist or metal mask and hence the sidewall of the $SiO_2$ pillars may be preferentially etched, thus producing the mushroom geometry. BOE (buffered oxide etchant) can be applied for 3 min to produce the mushroom geometry shown in FIG. 46B. For the exemplary case of RIE etching to get the mushroom configuration, a metal mask such as patterned circular Ni islands can be used as an etching mask for $SiO_2$ buffer layer underneath. Because of the RIE-etch-resistant Ni, the sidewall of the $SiO_2$ pillars (e.g., the regions near the top of the $SiO_2$ pillars) may become etched away more than the bottom region of the $SiO_2$ pillar, thus producing a mushroom configuration.

Figure 45:
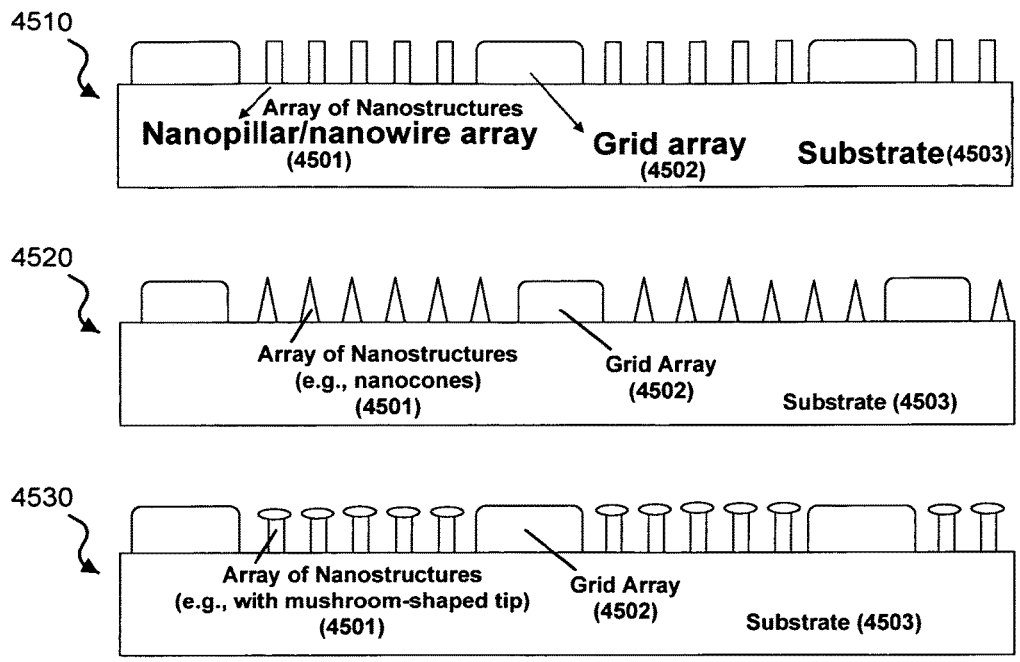
FIG. 45 shows exemplary schematic illustrations of superhydrophobic materials and a superomniphobic material to guard against compressive or shear stresses and make the materials more wear-resistant.

FIG. 47 shows exemplary images and contact angle measurement data for anti-fingerprint structures (e.g., like materials (4510), (4520), and (4530) illustrated in FIG. 45). For example, image (4710) shows water droplet on the surface of material (4610) with contact angle measured at 153°, which exemplifies superhydrophobic characteristics of the surface. Also for example, image (4720) shows an oil droplet (glycerol) on the surface of material (4610) with contact angle measured at 137°, which exemplifies strong non-wetting properties against oil.

Figure 48:
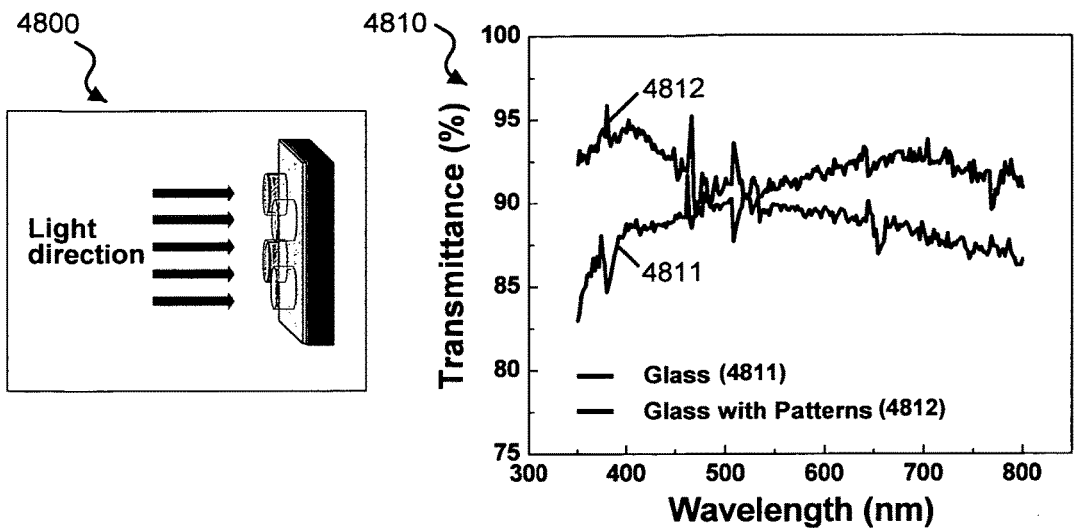
FIG. 48 shows an exemplary illustration of transparent, anti-fingerprint glass and a plot of exemplary optical transparency measurement data for top incident light.

The exemplary anti-fingerprint glass can be configured to be optical transparency, thereby useful as a display screen in a variety of devices and systems. FIG. 48 shows an exemplary illustration (4800) of transparent, anti-fingerprint glass and a plot (4810) of optical transparency measurement data (for top incident light) of the patterned anti-fingerprint coating of $SiO_2$ layer together with the soda lime glass underneath. The exemplary data of the patterned anti-fingerprint coating over glass substrate material is represented by the red waveform (4812), and the exemplary data of the plain glass is represented by the black waveform (4811). The light transmittance values are plotted against the optical wavelength used in this exemplary measurement. The exemplary $SiO_2$ pattern has a 5 μm diameter×5 μm spacing with a 10 μm height. The shoulder grid structure is ~10 μm wide and is crisscross patterned at every ~200 μm. Each grid square includes 20×20 pillar arrays, e.g., similar to the structure of material (4610) in FIG. 46A with a PTFE coating added. As shown in plot (4810), the transmittance was shown to be very good, with an average of ~92% for the top incident light over the visible spectrum range studied, which was shown to be better than the soda lime glass transmittance.

Figure 49:
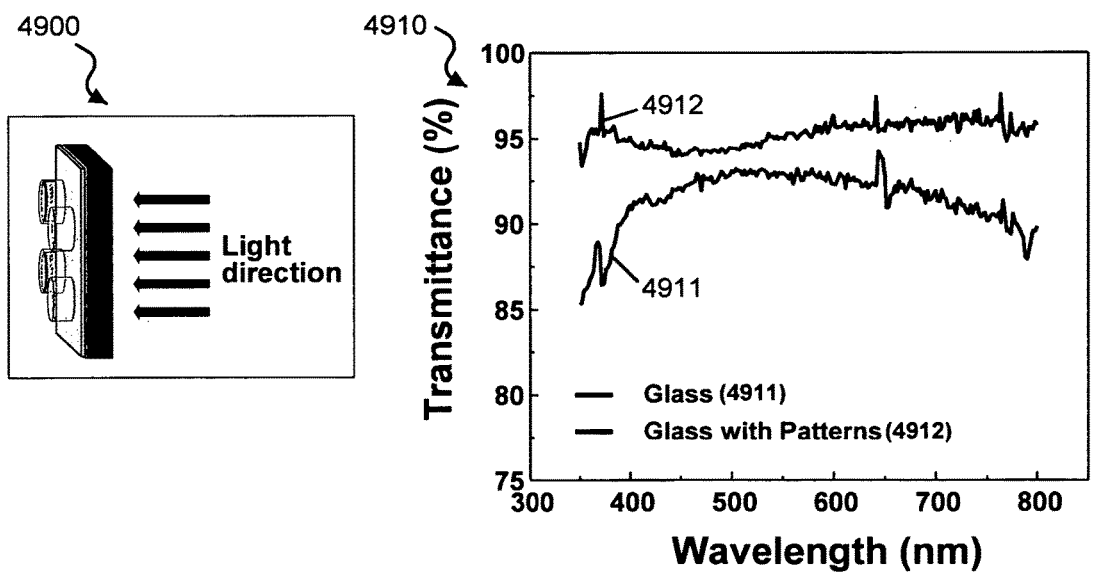
FIG. 49 shows an exemplary illustration of transparent, anti-fingerprint glass and a plot of exemplary optical transparency measurement data for bottom incident light.

FIG. 49 shows an exemplary illustration (4900) of transparent, anti-fingerprint glass and a plot (4910) of optical transparency measurement data (for bottom incident light) of the patterned anti-fingerprint coating of $SiO_2$ layer together with the soda lime glass underneath. For example, bottom incident light may be more representative of the touch-screen display devices and applications. The exemplary data of the patterned anti-fingerprint coating over glass substrate material is represented by the red waveform (4912), and the exemplary data of the plain glass is represented by the black waveform (4911). As shown in plot (4910), the patterned $SiO_2$ layer was shown to provide a better transmittance of ~95% average over the visible spectrum range studied.

Figure 50:
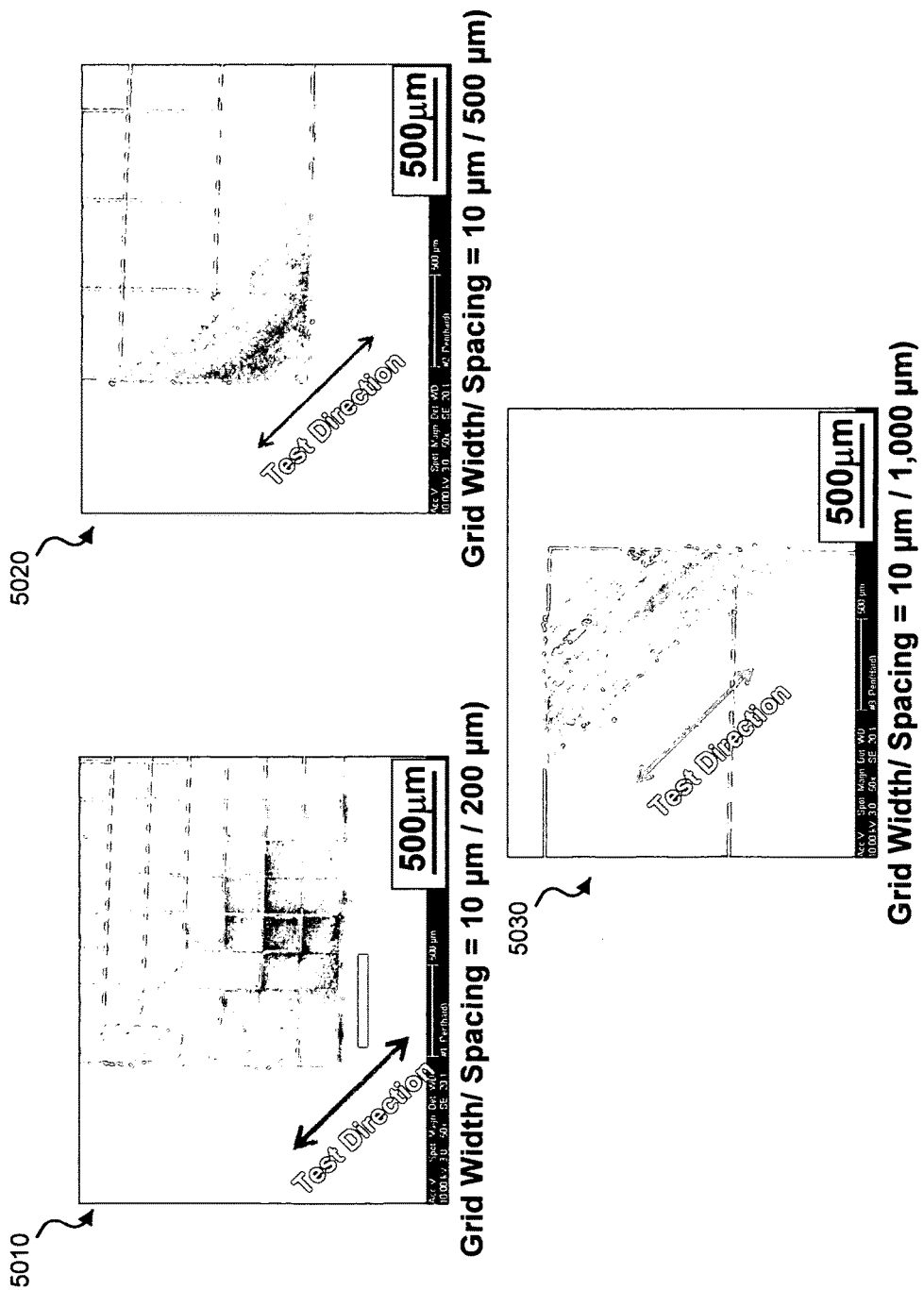
FIG. 50 shows low magnification images of three exemplary grid patterns for anti-fingerprint materials.
Figure 51:
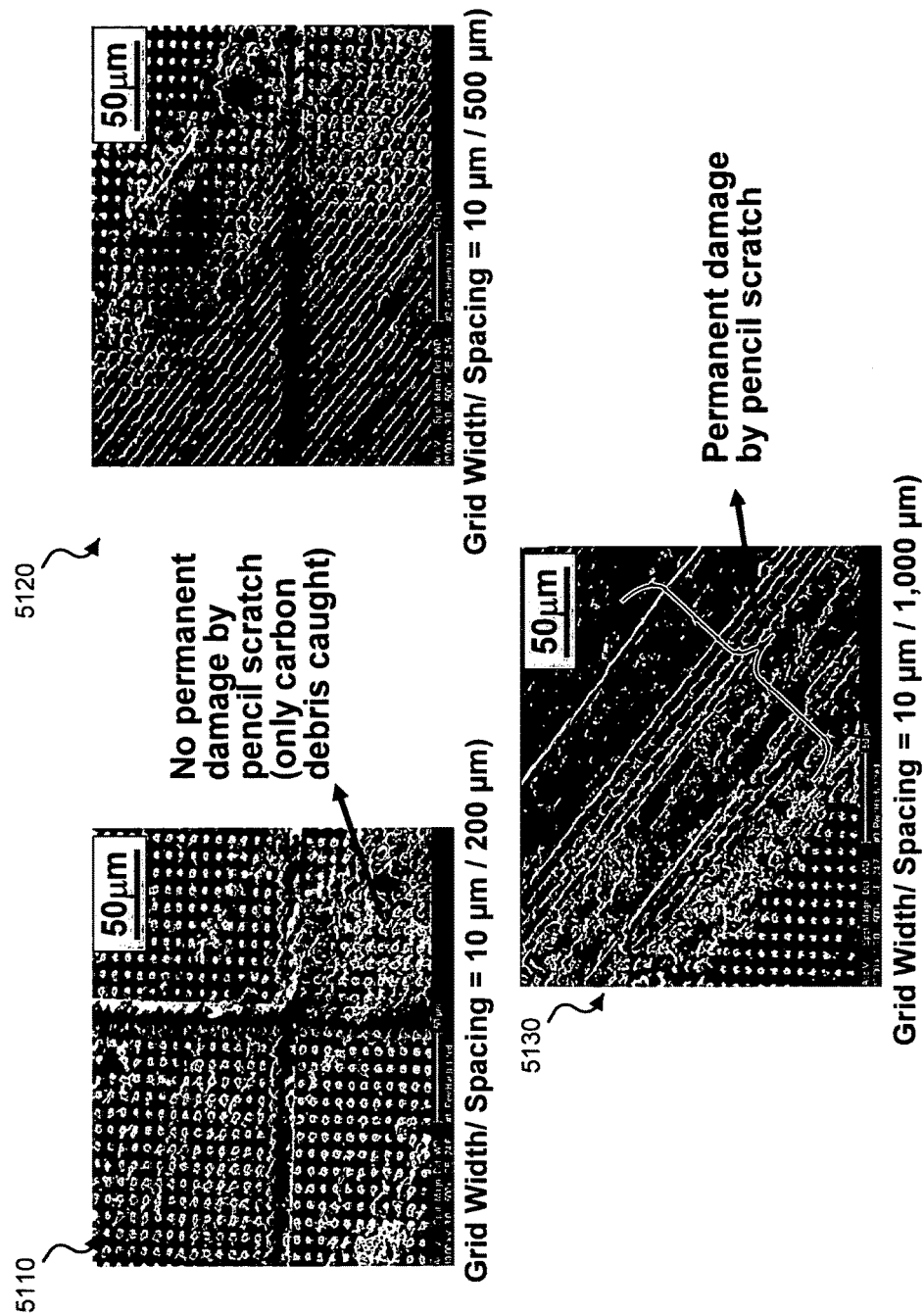
FIG. 51 shows high magnification images of three exemplary grid patterns for anti-fingerprint materials.

Wear resistance can also be considered as an important property for the anti-fingerprint coating. FIG. 50 shows three exemplary grid patterns for the anti-fingerprint coating $SiO_2$ structures and the wear-resistance (scratch resistance) after evaluating its resistance, e.g., by using a $H_2$ pencil to horizontally scratch the patterned surface. Low magnification micrographs are shown in FIG. 50 and high magnification micrographs are shown in FIG. 51, which clearly show the relative wear resistance of the patterned structures by pencil scratch wear testing on the exemplary anti-fingerprint $SiO_2$ patterns. Grid (5010) included a grid width 10 μm and spacing of 200 μm (~10% area fraction). Grid (5020) included a grid width 10 μm and spacing of 500 μm (~4% area fraction). Grid (5030) included a grid width 10 μm and spacing of 1000 μm (~2% area fraction). Of the three exemplary different grid shoulder designs tested, grid (5010) and grid (5020) were shown to be resistant to scratching (e.g., lateral pencil scratching). The less densely spaced sample grid (5030), for the given design and micropillar structure geometry, was shown to be severely scratched with a permanent damage. Therefore, the density of the grid shoulders was shown to be an important consideration for a given geometry (e.g., wider than 10 μm line width and grid density of 500 μm apart or smaller).

For example, to provide adequate protection against mechanical wear while at the same time maximizing optical transparency, a desired area fraction of the shoulder grid array structure (e.g., without the nano- or micro-patterning) can be considered within the range of 0.5-30% area fraction, and in some cases 1-20% or even 2-10%. For example, to provide adequate protection against mechanical force, the shoulder grid can be configured to have a micro-structural width dimension of at least 1/100 of the radius of curvature of pointed object, e.g. a pencil tip, stylus tip, finger tip, fingernail tip, etc. that can touch a viewing screen (either intentionally for display manipulations or inadvertently during handling and carrying). It is noted that a pencil typically has a radius of curvature of ~50-200 μm, so in this case, an exemplary grid line width can be configured to at least ~0.5-2 μm.

For an exemplary metallic mask, the patterning of metal layer can be accomplished by lithography or a combination of lithography and annealing induced ball-up process, as described previously (e.g., shown in FIG. 1 and FIG. 2). The use of a metal mask may be more convenient for nanoscale mask fabrication, e.g., in the diameter regime of 10-500 nm diameter. An exemplary process can include depositing a 5-20 nm thick layer of silver (Ag), gold (Au), nickel (Ni), copper (Cu) or alloys containing these metals, e.g., by at least 50% in weight. The deposited metal layer (e.g., deposited by sputtering, evaporation, electrochemical deposition or electroless deposition) can then be heated to 300-600° C. for 5-5000 min so that the film layer is broken up to form isolated metal nanoparticles to serve as mask for dry etching such as RIE or wet chemical etching.

Figure 8:
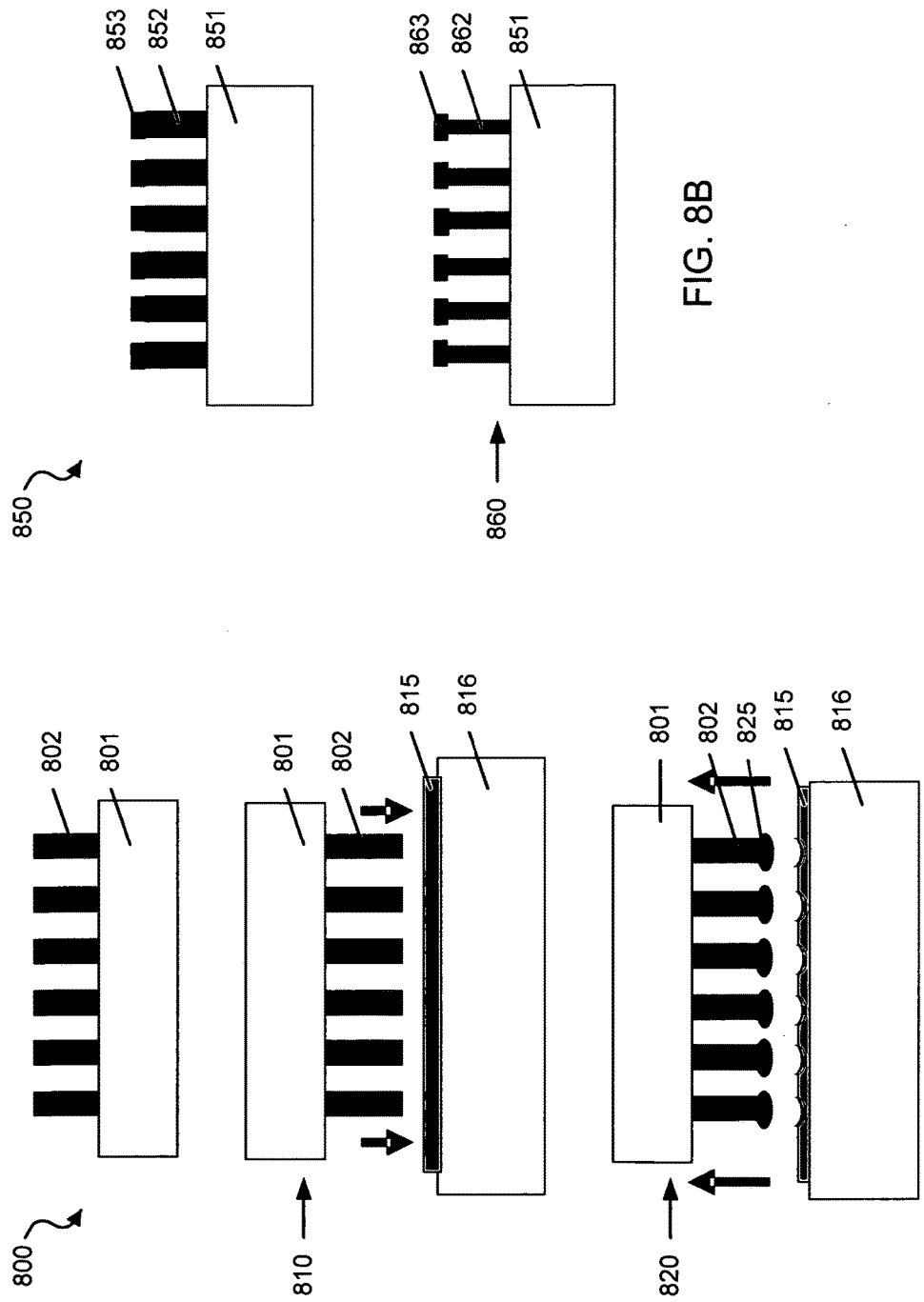
FIGS. 8A and 8B show exemplary schemes to produce mushroom geometry nanopillar tips.

In another aspect, vertical pillar structures can be fabricated by metal island masked etching and a $SiO_2$ buffer layer can further be modified by dip coating with a polymer material or glass precursor material (shown previously in FIG. 8) so that the nanopillar tips have a mushroom configuration to impart superoleophobic or superomniphobic properties. An additional annealing process may optionally used to produce higher purity glass or polymer with desirable crystal structures or amorphous structures with minimized binder and solvent contents. For example, FIG. 8 schematically illustrates a dip-coating method of forming a mushroom shaped nanopillar tip to impart oleophobic and omniphobic properties. In this example, the resultant material can be transparent and exhibit the super oleophobic and omniphobic properties. For example, a precursor of glass or silica (e.g., HSQ) can be used to add material to the nanopillar tip or nanotube tip, followed by baking for mushroom structure and omniphobic properties. Exemplary re-entrant tip geometry can be obtained by tip masking with metal islands and sidewall etching of nanopillars by using RIE, e.g., using a specific gas such as $SF_6$ (Si etching gas) with reduced or no $C_4F_8$ component (sidewall passivation gas that can prevent sidewall etching) in Si RIE etching process.

For special display devices, such as curved cell phones, tablets, laptops, gaming consoles and a variety of other devices and systems having touch-capable, curved viewing screens that need to be touch sensitive, the disclosed technology can include curved anti-fingerprint coatings, e.g., as illustrated in FIG. 9. The figure shows a super-omniphobic structure (900) that can include of curved display screen that is made of mechanically compliant yet optically transparent materials such as thin glass, polymer sheet, or elastomer (PDMS) sheet needs. The re-entrant nanopillar arrays (e.g., tip-mushroomed shape) can be formed by various embodiments described above, such as oblique incident deposition on nanopillars, dip-coating of precursor glass or polymer, or etch mask covered nano/micro pillars chemically etched to reduce the sidewall thickness. Such a compliant display screen having omniphobic surface structures and anti-fingerprint properties can then be peeled off the substrate, bent to a desired curvature to produce a curved display screen.

Figure 52:
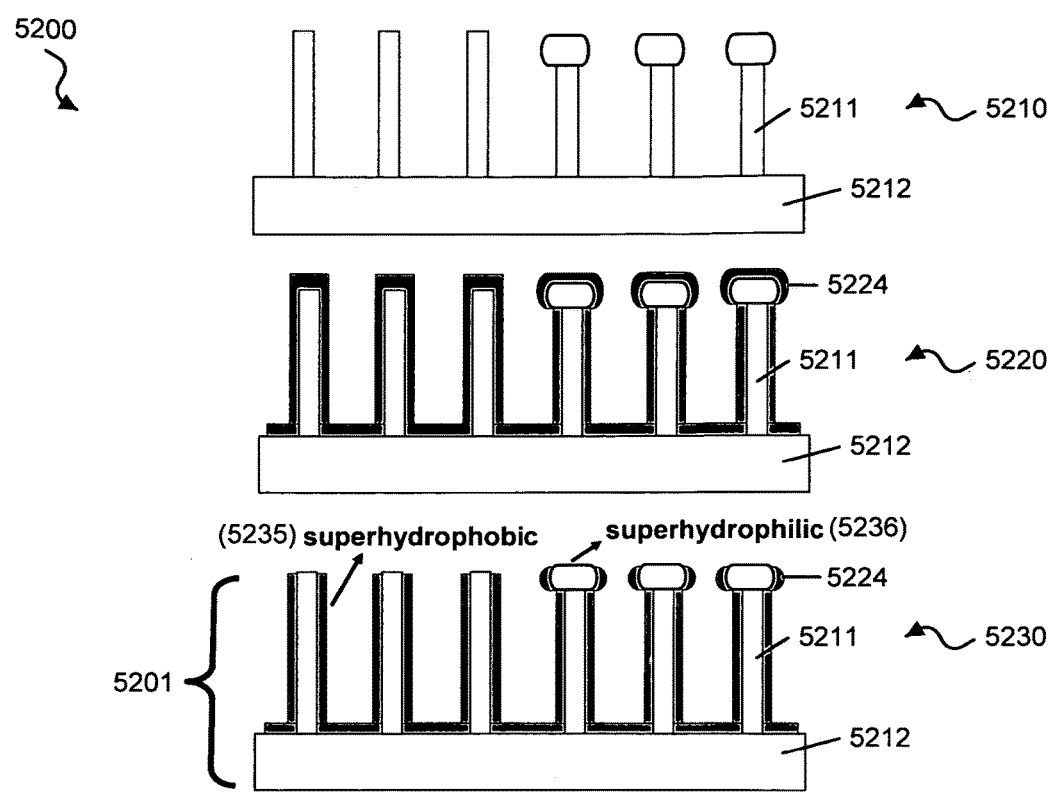
FIG. 52 shows an exemplary process to fabricate an optically transparent superomniphobic structure.

FIG. 52 shows an exemplary schematic illustration of process (5200) to fabricate an optically transparent super-omniphobic material (5201) that includes structurally mixed superhydrophobic+superhydrophilic regions to impart superomniphobic characteristics. For example, material (5201) can include nanowires or nanotubes of equi-diameter and/or have re-entrant mushroom shaped tips (e.g., by dip coating or lithographical sidewall etching). Using transparent nanostructured ceramics (e.g., silica, quartz or sapphire), mechanically wear-resistant, optically transparent and superomniphobic surfaces can be created. The vertically aligned nanorods, nanopillars, nanotubes of material (5201) can be made from transparent material such as silica, glass, sapphire having diameter that can be configured in the range of less than 100 nm to greater than 5 μm, and be vertically aligned at a desired angle of 70° or greater.

Process (5200) can include a process (5210) to fabricate vertically aligned nanostructures (5211) (e.g., nanorods, nanopillars, and nanotubes) on a substrate (5212), e.g., a transparent substrate or a transparent buffer layer deposited on transparent substrate such as glass or silica. Nanostructures (5211) can be fabricated such that they exhibit equivalent diameter and/or a re-entrant mushroom shape tip. Process can include fabricating nanostructures (5211) by self assembly, template-assisted method, by lithography on transparent substrate (5212), or by depositing a transparent buffer layer on another transparent substrate made of similar materials as the pillars. Process (5200) can include process (5220) to coat the surface of nanostructures (5211) by a hydrophobic layer (5224), e.g., a fluorine containing material such as PTFE or Teflon-like layer, or trichlorosilane by vapor deposition, liquid precursor filling and drying or baking. Process (5200) can include process (5230) to selectively remove the top of the superhydrophobic coating (5224), e.g., by ion or plasma etch, rapid chemical etch, or light mechanical polishing. Implementation of process (5200) can create a mixture of superhydrophobic trench regions (5235) and superhydrophilic pillar top regions (5236) of the material (5201), which becomes superomniphobic. For example, selection of mechanically harder materials such as ceramic or metal nanostructures can provide a structure having both wear-resistant and anti-fingerprint properties and superomniphobic surface.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few implementations and examples are described and other implementations, enhancements and variations can be made based on what is described and illustrated in this patent document.

We claim:

1. A method of fabricating a material with a pillar array surface, comprising:
   depositing a buffer layer of a buffer layer material on a substrate material, wherein the buffer layer material is a silicon-containing material;
   adding a film layer over the buffer layer;
   annealing the film layer to form balled-up structures that are distributed in an array of balled-up islands over the buffer layer to produce an etch mask;
   etching the buffer layer using the etch mask to create an array of pillar structures including the buffer layer material underneath the etch mask, wherein the pillar structures have a shape that includes at least one of a substantially straight cylinder, negatively tapered rod, or cone and are aligned substantially vertically, and wherein the pillar structures include the balled-up structures over the buffer layer material; and
   applying a coating over the array of pillar structures to form an outer hydrophobic layer comprising a hydrophobic material,
   wherein the applying the coating comprises dip coating the array of pillar structures into a thin layer of uncured PTFE, polydimethylsiloxane (PDMS), or poly(methyl methacrylate) (PMMA) to form a mushroom-shaped tip.

2. The method of claim 1, wherein the pillar array surface exhibits superhydrophobic, superoleophobic, or superomniphobic surface properties.

3. The method of claim 1, further comprising etching partially into the substrate material using the etch mask to create the array of pillar structures including the buffer layer material, the balled-up structures, and at least a portion of the substrate material underneath the etch mask.

4. The method of claim 1, wherein the substrate material includes at least one of silicon (Si), silicon-germanium (Si—Ge), zinc oxide (ZnO), gallium nitride (GaN), gallium arsenide (GaAs), sapphire, window glass, solar cell cover glass, soda lime silicate glass, quartz, alkaline earth boro-aluminosilicate, sodium boro-silicate glass, carbon, graphite, nitride, oxide, fluoride, or a metal, semiconductor, ceramic or polymer material, wherein the film layer comprises Ag, Au, Ni, or Cu.

5. A method of fabricating an anti-fingerprint surface coating structure, comprising:
    depositing a transparent buffer layer of a buffer layer material on a transparent substrate material, wherein the transparent buffer layer material is a silicon-containing material;
    adding a mask layer of a mask layer material over the transparent buffer layer, wherein the adding includes patterning the mask layer material to form a patterned mask;
    etching the transparent buffer layer using the patterned mask to create an array of pillar structures of the transparent buffer layer material underneath the patterned mask, wherein the pillar structures have a shape that includes at least one of a substantially straight cylinder, negatively tapered rod, or cone and are aligned substantially vertically; and
    coating the array of pillar structures with a hydrophobic layer including a hydrophobic material to produce a mushroom-shaped tip to the array of pillar structures.

6. The method of claim 1, wherein the etching the buffer layer using the etch mask includes retaining at least a portion of the buffer layer over the substrate.

7. The method of claim 1, wherein the adding the film layer includes depositing the film layer over the buffer layer in periodic patterns.

8. The method of claim 1, wherein the hydrophobic material includes at least one of polytetrafluoroethylene (PTFE), fluoroalkysilane (FAS), or a polymer having a $CF_3$-terminal group.

9. The method of claim 5, wherein the patterned mask includes an array of nano-sized shapes within a plurality of grids of crisscrossed lines of a particular spacing and a particular width.

10. The method of claim 5, wherein the hydrophobic material includes at least one of polytetrafluoroethylene (PTFE), fluoroalkysilane (FAS), or a polymer having a $CF_3$-terminal group.

11. The method of claim 5, wherein the applying the coating comprises dip coating the array of pillar structures into a thin layer of uncured PTFE, polydimethylsiloxane (PDMS), or poly(methyl methacrylate) (PMMA) to produce the mushroom-shaped tip.

* * * * *